(12) United States Patent
Kwong et al.

(10) Patent No.: US 8,470,834 B2
(45) Date of Patent: Jun. 25, 2013

(54) AZO-SUBSTITUTED PYRIDINE AND PYRIMIDINE DERIVATIVES AND THEIR USE IN TREATING VIRAL INFECTIONS

(75) Inventors: Cecil D. Kwong, Birmingham, AL (US); F. George Njoroge, Warren, NJ (US); Subramaniam Ananthan, Birmingham, AL (US); Feng Geng, Piscataway, NJ (US); Hollis S. Kezar, III, Hoover, AL (US); Joseph A. Maddry, Birmingham, AL (US); John J. Piwinski, Lebanon, NJ (US); Robert C. Reynolds, Birmingham, AL (US); John A. Secrist, III, Birmingham, AL (US); Neng-Yang Shih, Lexington, MA (US)

(73) Assignees: Merck Sharp & Dohme Corp., Rahway, NJ (US); Southern Research Institute, Birmingham, AL (US)

( * ) Notice: Subject to any disclaimer, the term of this patent is extended or adjusted under 35 U.S.C. 154(b) by 23 days.

(21) Appl. No.: 13/059,197

(22) PCT Filed: Aug. 19, 2009

(86) PCT No.: PCT/US2009/054269
§ 371 (c)(1),
(2), (4) Date: Aug. 5, 2011

(87) PCT Pub. No.: WO2010/022126
PCT Pub. Date: Feb. 25, 2010

(65) Prior Publication Data
US 2011/0286964 A1  Nov. 24, 2011

Related U.S. Application Data

(60) Provisional application No. 61/090,450, filed on Aug. 20, 2008.

(51) Int. Cl.
*C07D 239/50* (2006.01)
*C07D 213/72* (2006.01)
*C07D 405/02* (2006.01)
*A61K 31/505* (2006.01)
*A61K 31/443* (2006.01)
*A61K 31/497* (2006.01)

(52) U.S. Cl.
USPC .......... 514/256; 514/336; 514/338; 544/322; 544/333; 546/304; 546/283.7

(58) Field of Classification Search
None
See application file for complete search history.

(56) References Cited

U.S. PATENT DOCUMENTS

| 3,573,272 A | * | 3/1971 | Kaupp et al. ............... 534/610 |
| 3,856,772 A | * | 12/1974 | Dunkelmann et al. ........ 534/767 |
| 4,543,255 A | * | 9/1985 | Shealy et al. ............... 514/261.1 |
| 4,634,697 A |   | 1/1987 | Hamashima |
| 4,812,561 A |   | 3/1989 | Hamashima et al. |
| 4,916,224 A | * | 4/1990 | Vince et al. .................... 544/254 |
| 4,933,443 A |   | 6/1990 | Hamashima et al. |
| 4,988,703 A | * | 1/1991 | Norbeck et al. ......... 514/263.37 |
| 5,017,380 A |   | 5/1991 | Hamashima et al. |
| 5,246,931 A | * | 9/1993 | Norbeck et al. .............. 514/242 |
| 5,641,889 A | * | 6/1997 | Daluge et al. ..................... 564/1 |
| 5,747,496 A | * | 5/1998 | Cox et al. .................. 514/261.1 |
| 5,977,061 A | * | 11/1999 | Holy et al. ...................... 514/45 |
| 6,080,746 A | * | 6/2000 | Scheer ..................... 514/263.37 |
| 6,498,163 B1 |  | 12/2002 | Boschelli et al. |
| 6,534,512 B1 | * | 3/2003 | Vince et al. ................ 514/263.1 |

(Continued)

FOREIGN PATENT DOCUMENTS

DE  10212098 A1  10/2003
EP  0215759 A1  3/1987

(Continued)

OTHER PUBLICATIONS

Shealy, Y. et al., "Carbocyclic Analogs of Guanosine and 8-Azaguanosine", Journal of Pharmaceutical Sciences, 62(9), 1432-1434, 1973.*
Sen, D. et al.,"Synthesis of Some 2,4-Diamino-6-(substituted)-amino-5-arylazopyrimidines and their Effect on the Growth of *S. faecalis*", Journal of the Indian Chemical Society, 63, 420-424, 1986.*

(Continued)

*Primary Examiner* — Michael Barker
(74) *Attorney, Agent, or Firm* — Sheldon O. Heber; Raynard Yuro

(57) ABSTRACT

The present invention provides compounds of Formula (I): (Chemical formula should be inserted here as it appears on abstract in paper form) (I) and tautomers, isomers, and esters of said compounds, and pharmaceutically acceptable salts, solvates, and prodrugs of said compounds, wherein each of R, $R^1$, X, Y, Z, $R^2$, $R^3$, $R^4$, $R^5$, $R^6$, $R^7$, $R^8$, $R^9$, $R^{18}$, $R^{19}$, and n is selected independently and as defined herein. Compositions comprising such compounds are also provided. The compounds of the invention are effective as inhibitors of HCV, and are useful, alone and together with other therapeutic agents, in treating or preventing diseases or disorders such as viral infections and virus-related disorders.

(I)

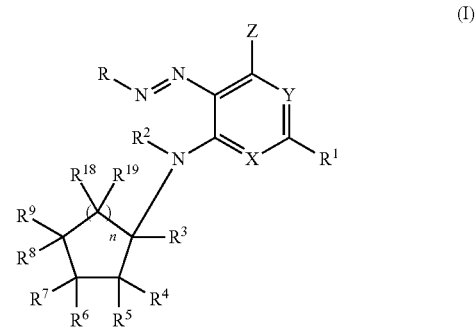

17 Claims, No Drawings

U.S. PATENT DOCUMENTS

| | | | |
|---|---|---|---|
| 6,800,434 B2 | 10/2004 | Saksena et al. | |
| 6,838,475 B2 | 1/2005 | Arasappan et al. | |
| 6,846,802 B2 | 1/2005 | Chen et al. | |
| 6,911,428 B2 | 6/2005 | Zhu et al. | |
| 6,914,122 B2 | 7/2005 | Venkatraman et al. | |
| 7,012,066 B2 | 3/2006 | Saksena et al. | |
| 2002/0058635 A1* | 5/2002 | Averett | 514/43 |
| 2002/0160962 A1 | 10/2002 | Saksena et al. | |
| 2005/0176648 A1 | 8/2005 | Saksena et al. | |
| 2005/0249702 A1 | 11/2005 | Njoroge et al. | |

FOREIGN PATENT DOCUMENTS

| | | |
|---|---|---|
| FR | 2574407 A1 | 6/1986 |
| JP | 49-26295 * | 3/1974 |
| WO | 93/17020 A2 | 9/1993 |
| WO | 98/14181 A1 | 4/1998 |
| WO | 98/17679 A1 | 4/1998 |
| WO | 98/22496 A2 | 5/1998 |
| WO | 99/07734 A2 | 2/1999 |
| WO | 00/07998 A1 | 2/2000 |
| WO | 01/07027 A2 | 2/2001 |
| WO | 02/08205 A1 | 1/2002 |
| WO | 03/084953 A1 | 10/2003 |
| WO | 2004/037166 A2 | 5/2004 |
| WO | 2006/065590 A2 | 6/2006 |
| WO | 2006/136442 A1 | 12/2006 |
| WO | 2007/003596 A1 | 1/2007 |
| WO | 2008/032162 A1 | 3/2008 |
| WO | 2008/040778 A2 | 4/2008 |
| WO | 2008/124161 A1 | 10/2008 |

OTHER PUBLICATIONS

Sen, D. et al., "Synthesis of Some 5-Arylazo-6-(substituted amino) Pyrimidines", Journal of the Indian Chemical Society, 47(4), 1970.*

Sen, D. et al., "2,4-Diamino-5-arylazo-6-(substituted amino) pyrimidines as possible folic acid antagonists", Chemical Abstracts, 99:158360, 1983.*

Bhushan et al., "Synthesis of Conformationally Restricted 2', 3'-exo-Methylene Carbocyclic Nucleosides Built on a Bicyclo[3.1.0]hexane Template", Bioorganic & Medicinal Chemistry, 10, 2325-2333, 2002.*

Borthwick, Alan D. et al., "Fluorocarbocyclic Nucleosides: Synthesis and Antiviral Activity of 2'- and 6'-Fluorocarbocyclic 2'-Deoxy Guanosines", Journal of Medicinal Chemistry, 34, 907-914, 1991.*

Figueira, M. Jose et al., "Synthesis and Antiviral and Cytostatic Activities of Carbocyclic Nucleosides Incorporating a Modified Cyclobutane Ring", Arch. Pharm. Pharm. Med. Chem., 332, 348-352, 1999.*

Gonzalez-Diaz, Humberto et al., "QSAR for anti-RNA-virus activity, synthesis, and assay of anti-RSV carbonucleosides given a unified representation of spectral moments, quadratic, and topologic indices", Bioorganic & Medicinal Chemistry Letters, 15, 1651-1657, 2005.*

Patil, Sharadbala D. et al., "Synthesis and Antiviral Properties of -5'-Noraristeromycin and Related Purine Carbocyclic Nucleosides. A New Lead for Anti-Human Cytomegalovirus Agent Design", Journal of Medicinal Chemistry, 35, 3372-3377, 1992.*

Israel, Mervyn et al., "Pyrimidine Derivatives VIII. 5-Arylazopyrimidines and Their Inhibitory Effects Against Transplantable Mouse Tumors", Journal of Pharmaceutical Sciences, 55(6), 1966.*

Anderson et al., The Practice of Medicinal Chemistry (1996), Academic Press, New York.

Beaulieu et al., "Inhibitors of the HCV NS5B polymerase: New hope for the treatment of hepatitis C infections", Current Opinion in Investigational Drugs, 2004, p. 838-850, vol. 5, No. 8.

S. Berge et al., Journal of Pharmaceutical Sciences (1977) 66 (1), p. 1-19.

A.L. Bingham et al., "Over one hundred solvates of sulfathiazole", Chem. Commun., 603-604 (2001).

BioWorld Today 9(217):4 (Nov. 10, 1998).

Burgess, K.; Ke, Chun-Yen, "Large Scale Syntheses of N-Protected 2,3-Methanomethionine Stereoisomers", Synthesis, 1996, p. 1463-1467.

M. Caira et al., "Preparation and Crystal Characterization of a Polymorph, a Monohydrate, and an Ethyl Acetate Solvate of the Antifungal Fluconazole", Journal of Pharmaceutical Sciences, 2004, p. 601-611, vol. 93, No. 3.

Davey, D.D. et al., "Design, Synthesis, and Activity of 2-Imidazol-1-ylpyrimidine Derived Inducible Nitric Oxide Synthase Dimerization Inhibitors", J. Med. Chem. 2007, p. 1146-1157, vol. 50, No. 6.

Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, p. 7461-7469, vol. 71, No. 10.

Elzouki, et al., "Serine protease inhibitors in patients with chronic viral hepatitis", Journal of Hepatology, 1997, p. 42-48, vol. 27.

Gould, Philip L., "Salt selection for basic drugs", International Journal of Pharmaceutics, 1986, p. 201-217, vol. 33.

T.W. Green et al., Protective Groups in Organic Synthesis (1991), Wiley, New York.

T. Higuchi and V. Stella, Pro-drugs as Novel Delivery Systems (1987) 14 of the A.C.S. Symposium Series.

Holland et al., "Hepatitis C Genotyping by Direct Sequencing of the Product from the Roche Amplicor Test: Methodology and Application to a South Australian Population", Pathology, 1998, p. 192-195, vol. 30.

Ingallinella et al., "Potent Peptide Inhibitors of Human Hepatitis C Virus NS3 Protease Are Obtained by Optimizing the Cleavage Products", Biochemistry, 1998, p. 8906-8914, vol. 37, No. 25.

Koga, M., et al., "C-2 Arylamino Substituted Purine ara-Carbocyclic Nucleosides as Potential Anti-Cytomegalovirus Agents", Journal of Heterocyclic Chemistry, 1992, vol. 29, pp. 1741-1747, No. 7.

Lamballerie et al., "Classification of hepatitis C virus variants in six major types based on analysis of the envelope 1 and nonstructural 5B genome regions and complete polyprotein sequences", Journal of General Virology, 1997, pp. 45-51, vol. 78 (PT1).

Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, p. 9340-9348, vol. 36, No. 31.

Legraverend, et al., "(+)-2-Amino-3,4-dihydro-7-[2,3-dihydroxy-4-(hydroxymethyl)-1-cyclopentyl]-7H-pyrrolo[2,3-d]pyrimidin-4-ones: New Carbocyclic Analogues of 7-Deazaguanosine with Antiviral Activity", J. Med. Chem., 1985, p. 1477-1480, vol. 28, No. 10.

Liu, et al., "Synthesis of Enantiomerically Pure N-tert-Butanesulfinyl Imines (tert-Butanesulfinimines) by the Direct Condensation of tert-Butanesulfinamide with Aldehydes and Ketones", J. Org. Chem., 1999, pp. 1278-1284, vol. 64, No. 4.

Llinas-Brunet et al., "Peptide-Based Inhibitors of the Hepatitis C Virus Serine Protease", Bioorganic & Medicinal Chemistry Letters, 1998, p. 1713-1718, vol. 8.

Malcolm, et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, p. 1013-1020, vol. 50, No. 3.

Martin, F., et al., "Affinity selection of a camelized VH domain antibody inhibitor of hepatitis C virus NS3 protease", Protein Engineering, 1997, p. 607-614, vol. 10, No. 5.

Martin, F., et al., "Design of Selective Eglin Inhibitors of HCV NS3 Proteinase", Biochemistry, 1998, p. 11459-11468, vol. 37, No. 33.

Ni, Z-J., et al., "Progress and development of small molecule HCV antivirals", Current Opinion in Drug Discovery & Development, 2004, p. 446-459, vol. 7, No. 4.

Prakash, et al., "Stereoselective Nucleophilic Trifluoromethylation of N-(tert-Butylsulfinyl)-imines by Using Trimethyl (trifluoromethyl)-silane", Angew. Chem. Int. Ed., 2001, p. 589-590, vol. 40, No. 3.

Roche, E.B., "Bioreversible Carriers in Drug Design", 1987.

Sakamoto, T. et al., "Condensed Heteroaromatic Ring Systems. VII. Synthesis of Thienopyridines, Thienopyrimidines, and Furopyridines from o-Substituted N-Heteroarylacetylenes", Chem. Pharm. Bull., 1986, p. 2719-2724, vol. 34, No. 7.

Simmonds, P., et al., "Classification of hepatitis C virus into six major genotypes and a series of subtypes by phylogenetic analysis of the NS-5 region", Journal of General Virology, 1993, p. 2391-2399, vol. 74.

Simmonds, P., et al., "Identification of genotypes of hepatitis C virus by sequence comparisons in the core, E1 and NS-5 regions", Journal of General Virology, 1994, p. 1053-1061, vol. 75.

Stahl, P., et al., "Handbook of Pharmaceutical Salts. Properties, Selection and Use", 2002, Zurich: Wiley-VCH.

Tan, S-L, et al., "Hepatitis C Therapeutics: Current Status and Emerging Strategies", Nature Reviews, 2002, p. 867-881, vol. 1.

Van Tonder, E.C., et al., "Preparation and Physicochemical Characterization of 5 Niclosamide Solvates and 1 Hemisolvate", AAPS PharmSciTech, 2004, p. 1-10, vol. 5, No. 1, Article 12.

Moriarty, K.J., et al., "The synthesis and SAR of 2-amino-pyrrolo[2,3-d]pyrimidines: A new class of Aurora-A kinase inhibitors", Bioorganic & Medicinal Chemistry Letters, 2006, vol. 16, pp. 5778-5783.

Patil, S., et al., "Synthesis and Antiviral Properties of (±)-5'-Noraristeromycin and Related Purine Carbocyclic Nucleosides. A New Lead for Anti-Human Cytomegalovirus Agent Design", J. Med. Chem., 1992, vol. 35, pp. 3372-3377, No. 18.

Shealy, Y.F., et al., "Carbocyclic Analogs of Guanosine and 8-Azaguanosine", Journal of Pharmaceutical Sciences, 1973, vol. 62, pp. 1432-1434, No. 9.

Shealy, Y.F., et al., "Synthesis and Antiviral Evaluation of Carbocyclic Analogues of 2-Amino-6-substituted-purine 3'-Deoxyribofuranosides", J. Med. Chem., 1987, vol. 30, pp. 1090-1094, No. 6.

Sheldon, J. et al., "Novel protease and polymerase inhibitors for the treatment of hepatitis C virus infection", Expert Opinion Investig. Drugs, 2007, vol. 16, pp. 1171-1181, No. 8.

Toogood, P.L., et al., "Discovery of a Potent and Selective Inhibitor of Cyclin-Dependent Kinase", J. Med. Chem., 2005, vol. 48, pp. 2388-2406, No. 7.

International Search Report for PCT/US2009/054264, mailed Feb. 8, 2010, (4 pages).

Written Opinion of The International Searching Authority for PCT/US2009/054264, (8 pages), Feb. 20, 2011.

International Search Report for PCT/US2009/054268, mailed Feb. 1, 2010, (7 pages).

Written Opinion of The International Searching Authority for PCT/US2009/054268, (5 pages), Feb. 20, 2011.

International Search Report for PCT/US2009/054269, mailed Dec. 15, 2009, (4 pages).

Written Opinion of The International Search Authority for PCT/US2009/054269, (7 pages), Feb. 20, 2011.

International Search Report for PCT/US2009/054271, mailed Jan. 19, 2010, (4 pages).

Written Opinion of the International Search Authority for PCT/US2009/054271, (6 pages), Feb. 20, 2011.

Bhushan, R.G., et al., "Synthesis of Conformationally Restricted 2',3'-exo-Methylene Carbocyclic Nucleosides Built on a Bicyclo[3.1.0]hexane Template", Bioorganic & Medicinal Chemistry, 2002, vol. 10, pp. 2325-2333.

Nishio, M., et al., "Antiviral effect of 6-diazo-5-oxo-L-norleucine, antagonist of γ-glutamyl transpeptidase, on replication of human parainfluenza virus type 2", Journal of General Virology, 1990, vol. 71, pp. 61-67.

* cited by examiner

AZO-SUBSTITUTED PYRIDINE AND PYRIMIDINE DERIVATIVES AND THEIR USE IN TREATING VIRAL INFECTIONS

CROSS-REFERENCE TO RELATED APPLICATION

This application is a 371 of PCT application no. US2009/054269, filed Aug. 19, 2009, which claims benefit of provisional application U.S. Ser. No. 61/090,450, filed Aug. 20, 2008, incorporated by reference.

FIELD OF THE INVENTION

The present invention relates to certain azo-substituted pyridine and pyrimidine derivatives, to compositions comprising them, and to methods for their use as inhibitors of HCV and in treating or preventing viral infections or virus-related disorders.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kd in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: NI-L-C-E1-E2-p7-NS2—NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include a-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase has provided important structural insights that should assist in the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2′,3′-dideoxy-3′-thiacytidine 5′-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

The present invention provides certain azo-substituted pyridine and pyrimidine derivatives (collectively referred to herein as "compounds of the invention"), compositions comprising such compounds, and methods for their use as HCV inhibitors and for treating viral infections and disorders related thereto.

In one embodiment, the compounds of the invention have a general structure shown in Formula (I):

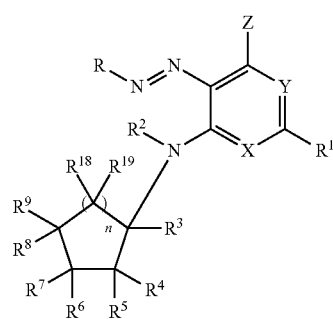

(I)

and include tautomers, isomers, and esters of said compounds, and pharmaceutically acceptable salts, solvates, and prodrugs of said compounds, tautomers, isomers, and esters, wherein each of R, $R^1$, X, Y, Z, $R^2$, $R^3$, $R^4$, $R^5$, $R^6$, $R^7$, $R^8$, $R^9$, $R^{18}$, $R^{19}$ and n are selected independently and wherein:

R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl,
  wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkynyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)NH$_2$, —C(O)NHR$^{10}$, —C(O)NR$^{10}$R$^{11}$, —OC(O)NH$_2$, —CO(O)NHR$^{10}$, —CO(O)NR$^{10}$R$^{11}$, —NH$_2$, —NHR$^{10}$, —NR$^{10}$R$^{11}$, —NO$_2$, —S(O)NHR$^{10}$, —S(O)NR$^{10}$R$^{11}$—S(O)R$^{10}$, —S(O)$_2$NH$_2$, —S(O)$_2$NHR$^{10}$, —S(O)$_2$NR$^{10}$R$^{11}$, —S(O)$_2$R$^{10}$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$, —NHR$^{12}$, and —NR$^{12}$R$^{13}$;

$R^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

$R^2$ (when $R^2$ is not joined with $R^9$) is selected from H and alkyl;

n=0, 1, or 2;

$R^3$ is selected from H, -alkyl, -alkenyl, alkynyl, aryl, heteroaryl, and cycloalkyl,
  wherein each of said -alkyl, said -alkenyl, said alkynyl, said aryl, said heteroaryl, and said cycloalkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

R⁴ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰,
- wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

R⁵ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰,
- wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, -haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;
- or, alternatively, R⁴ and R⁵ are taken together with the carbon atom to which they are shown attached to faint a 3- to 7-membered, saturated or partially unsaturated, spirocycloalkyl ring containing from 0 to 3 spiro ring heteroatoms selected from O, N, and S;

R⁶ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰,
- wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, R⁵ and R⁶ are taken together to form in a double bond;

R⁷ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰,
- wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;
- or, alternatively, R⁶ and R⁷ are taken together with the carbon atom to which they are shown attached to form a 3- to 7-membered, saturated or partially unsaturated, spirocycloalkyl ring containing from 0 to 3 spiro ring heteroatoms selected from O, N, and S;

R⁸ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰,
- wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R¹⁰)R¹¹, —O(C)O—NHR¹¹, —O(C)O—NH₂, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)₂R¹⁰, —SR¹⁰, —S(O)₂NHR¹⁰, —S(O)₂NR¹⁰R¹¹, —CN, —NH₂, —NHR¹⁶, and —NR¹⁶R¹⁷, —N(R¹⁰)S(O)₂R¹⁰, —NHS(O)₂R¹⁰, aryl, heteroaryl, cycloalkyl, cycloalkenyl, heterocycloalkyl, and heterocycloalkenyl;

R⁹ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹(O)NHR¹⁰, S(O)NR¹⁰R¹¹, —S(O)R¹⁰, —S(O)₂NHR¹⁰, —S(O)₂NR¹⁰R¹¹, and —S(O)₂R¹⁰,
- wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R¹⁰)R¹¹, —O(C)O—NHR¹¹, —O(C)O—NH₂, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

or, alternatively, R$^8$ and R$^9$ are taken together with the carbon atom to which they are shown attached to form a 3- to 7-membered, saturated or partially unsaturated, spirocycloalkyl ring containing from 0 to 3 spiro ring heteroatoms selected from O, N, and S;

each R$^{18}$ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each R$^{19}$ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, n is 1 and R$^{18}$ and R$^{19}$ are taken together with the carbon atom to which they are attached to form a 3- to 7-membered, saturated or partially unsaturated, spirocycloalkyl ring containing from 0 to 3 spiro ring heteroatoms selected from O, N, and S;

or, alternatively, R$^4$ and R$^7$, together with the carbon atoms to which they are shown attached, form a moiety (1C):

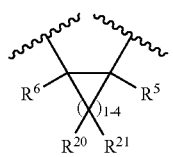

(1C)

wherein R$^{20}$ and R$^{21}$ are each independently selected from H, alkyl, and heteroalkyl and wherein R$^5$ and R$^6$ are defined above, with the proviso that when R$^4$ and R$^7$ form a moiety (1C), then R$^5$ and R$^6$ are not taken together to form a double bond;

or, alternatively, R$^4$ and R$^7$, together with the carbon atoms to which they are shown attached, form a moiety (1D):

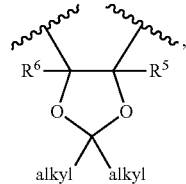

(1D)

wherein R$^5$ and R$^6$ are as defined above;

or, alternatively, R$^4$ and R$^7$, together with the carbon atoms to which they are shown attached, form a moiety (1E):

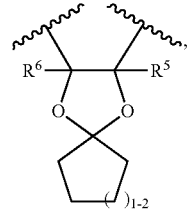

(1E)

wherein R$^5$ and R$^6$ are as defined above;

each R$^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{10}$ and R$^{11}$ are linked together with the nitrogen to which they are attached to form an unsubstituted or substituted 4- or 6-membered heterocycloalkyl;

each R$^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{12}$ and R$^{13}$ are linked together with the nitrogen to which they are attached to form an unsubstituted or substituted 4- to 6-membered heterocycloalkyl;

each R$^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, R$^{14}$ and R$^{15}$ are linked together with the nitrogen to which they are attached to form an unsubstituted or substituted 4- to 6-membered heterocycloalkyl;

each R$^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl; and each R$^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{16}$ and R$^{17}$ are linked together with the nitrogen to which they are attached to form an unsubstituted or substituted 4- or 6-membered heterocycloalkyl.

In another embodiment, the invention provides compositions, including pharmaceutical compositions, comprising one or more compounds of the invention (e.g., one compound of the invention), or a pharmaceutically acceptable salt, solvate, ester, or prodrug thereof, and a pharmaceutically acceptable carrier or diluent. In one embodiment, said compound or compounds of the invention are present in the composition in an amount effective for inhibiting HCV, and/or for treating or preventing a viral infection or a virus-related disorder in a patient in need thereof.

In another embodiment, the invention provides a pharmaceutical composition comprising one or more compounds of the invention, or a pharmaceutically acceptable salt, solvate, ester, or prodrug thereof, together with one or more additional therapeutic agents, optionally further comprising a pharmaceutically effective carrier or diluent. Non-limiting examples of such additional therapeutic agents include one or more of any of the following: HCV polymerase inhibitors, HCV protease inhibitors, HCV replicase inhibitors, nucleosides, Interferon, and/or ribavirin (or Levovirin or Viramidine). Non-limiting examples of interferon include PEG-interferon, PEG interferon alpha conjugate, alpha-interferon, and pegylated interferon. These and other examples are known to those of ordinary skill in the art.

In another embodiment, the present invention provides for the use of one or more compounds of the invention, or a pharmaceutically acceptable salt, solvate, ester, and/or prodrug thereof, alone or in combination with one or more additional therapeutic agents such as those described above, for inhibiting HCV and/or for treating or preventing a viral infection or a virus-related disorder in a patient in need thereof.

In another embodiment, the invention provides a method of inhibiting HCV in vivo, ex vivo, or in vitro, comprising exposing a population of cells comprising HCV to an effective amount of at least one compound of the invention, or a pharmaceutically acceptable salt, solvate, ester, or prodrug thereof, alone or in combination with one or more additional therapeutic agents such as those described above. In one such embodiment, the compound or compounds of the invention are used as the neat chemical. In another such embodiment, the compounds of the invention are used in the form of a pharmaceutically acceptable composition.

In another embodiment, the invention provides a method for treating or preventing a viral infection or a virus-related disorder in a patient, comprising administering to the patient an effective amount of at least one compound of the invention, or a pharmaceutically acceptable salt, solvate, ester, or prodrug thereof, alone or in combination with one or more additional therapeutic agents such as those described above. In one such embodiment, the compound or compounds of the invention are used as the neat chemical. In another such embodiment, the compounds of the invention are used in the form of a pharmaceutically acceptable composition.

The details of the invention are set forth in the accompanying detailed description below. Although any methods and materials similar to those described herein can be used in the practice or testing of the present invention, illustrative methods and materials are described herein. Other features, objects, and advantages of the invention will be apparent from the description and the claims. All patents and publications cited in this specification are incorporated herein by reference.

DETAILED DESCRIPTION OF THE INVENTION

In one embodiment, the compounds of the invention have the structural Formula (A) as described above, and include pharmaceutically acceptable salts, esters, prodrugs, tautomers, and isomers of said compounds.

In one embodiment, the compounds of the invention have a general structure shown in Formula (I) above.

In one embodiment, in Formula (I), each of R$^3$, R$^5$, R$^6$, and R$^8$ is H.

In one embodiment, in Formula (I), n is 1; each of $R^2$, $R^3$, $R^5$, $R^6$, $R^8$, $R^{18}$ and $R^{19}$ is H; $R^4$ and $R^7$ are OH; and $R^9$ is alkyl, wherein said alkyl is unsubstituted or substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —OC(O)-alkyl, —OC(O)-alkenyl, —OC(O)-haloalkyl, —OC(O)-haloalkenyl, —O(C)O—$NHR^{10}$, —O(C)O—$N(R^{10})R^{11}$, —C(O)O-alkyl, —C(O)O-alkenyl, —C(O)O-haloalkyl, —C(O)O-haloalkenyl, —$S(O)_2R^{10}$, —$SR^{10}$, —$S(O)_2NHR^{10}$, —$S(O)_2NR^{10}R^{11}$, —CN, —$NH_2$, —$NHR^{16}$, and —$NR^{16}R^{17}$, —$NHS(O)_2R^{10}$, —$N(R^{10})S(O)_2R^{10}$, aryl, heteroaryl, cycloalkyl, cycloalkenyl, heterocycloalkyl, and heterocycloalkenyl.

In one embodiment, in Formula (I), n is 1; each of $R^2$, $R^3$, $R^5$, $R^6$, $R^8$, $R^{18}$ and $R^{19}$ is H; $R^4$ and $R^7$ are OH; and $R^9$ is alkyl, wherein said alkyl is unsubstituted or substituted with from one to five groups independently selected from —OH, halo, —CN, —$NH_2$, —$NHR^{16}$, —$NR^{16}R^{17}$, —$NHS(O)_2R^{10}$, —$N(R^{10})S(O)_2R^{10}$, —Oalkyl, —Ocycloalkyl, —O-alkyl-cycloalkyl, —OC(O)-alkyl, —O(C)O—$NHR^{10}$, —O(C)O—$N(R^{10})R^{11}$, —C(O)O-alkyl, —$S(O)_2R^{10}$, —$SR^{10}$, —$S(O)_2NHR^{10}$, and —$S(O)_2NR^{10}R^{11}$.

In one embodiment, in Formula (I), n is 1; each $R^2$, $R^3$, $R^5$, $R^6$, $R^8$, $R^{18}$ and $R^{19}$ is H; $R^4$ and $R^7$ are OH; and $R^9$ is methyl, wherein said methyl is unsubstituted or substituted with from one to three groups independently selected from —OH, halo, alkyl, —CN, —$NH_2$, —$NHR^{16}$, —$NR^{16}R^{17}$, —$NHS(O)_2R^{10}$—Oalkyl, —Ocycloalkyl, —O-alkyl-cycloalkyl, —OC(O)-alkyl, —O(C)O—$NHR^{10}$, —O(C)O—$N(R^{10})R^{11}$, —C(O)O-alkyl, —$S(O)_2R^{10}$, —$SR^{10}$, —$S(O)_2NHR^{10}$, and —$S(O)_2NR^{10}R^{11}$.

In some embodiments, $R^9$ is -alkyl-$NHS(O)_2R^{10}$, wherein $R^{10}$ is selected from methyl, ethyl, and cyclopropyl.

In some embodiments, $R^9$ is selected from -alkyl —$N(CH_3)S(O)_2R^{10}$ and -alkyl-$N(CH_2CH_3)S(O)_2R^{10}$, wherein $R^{10}$ is selected from methyl, ethyl, and cyclopropyl.

In some embodiments, $R^9$ is -alkyl-O(C)O—$NHR^{10}$, wherein $R^{10}$ is selected from methyl, ethyl, and cyclopropyl.

In some embodiments, $R^9$ is selected from $R^9$-alkyl-0(C)O—$N(CH_3)R^{10}$ and —O(C)O—$N(CH_2CH_3)R^{10}$, wherein $R^{10}$ is selected from methyl, ethyl, and cyclopropyl.

In one embodiment, in Formula (I), n is 1; each of $R^2$, $R^3$, $R^5$, $R^6$, $R^8$, $R^{18}$ and $R^{19}$ is H; $R^4$ and $R^7$ are OH; and $R^9$ is selected from —$CH_2$—O-alkyl, —$CH_2$—OH, —$CH_3$, H, —$CH_2$—$CH_3$,—$CH_2$—$OC(O)CF_3$, —$CH_2$—$NH_2$, —$CH_2$—$NHR^{16}$, and —$CH_2$—$NR^{16}R^{17}$.

In one embodiment, in Formula (I), each of $R^3$, $R^5$, $R^6$, and $R^8$ is H and each of $R^4$ and $R^7$ is —OH.

In one embodiment, in Formula (I), each of $R^3$, $R^5$, $R^6$, and $R^8$ is H; each of $R^4$ and $R^7$ is —OH; and $R^9$ is —O-alkyl.

In one embodiment, in Formula (I), each of $R^3$, $R^5$, $R^6$, and $R^8$ is H; each of $R^4$ and $R^7$ is —OH; and $R^9$ is —O—$CH_3$.

In one embodiment, in Formula (I), each of $R^3$, $R^5$, $R^6$, and $R^8$ is H; each of $R^4$ and $R^7$ is —OH; $R^9$ is —O—$CH_3$, and n is 1.

In one embodiment, in Formula (I), each of $R^3$, $R^5$, $R^6$, and $R^8$ is H; each of $R^4$ and $R^7$ is —OH; $R^9$ is —O—$CH_3$, and n is 2.

In one embodiment, the compounds of the invention have the structural Formula (I.A):

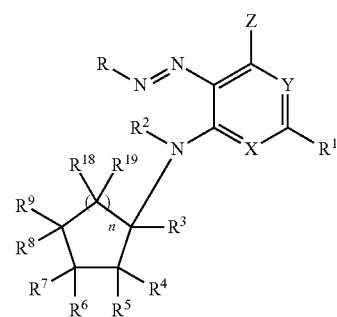

(I.A)

and includes tautomers, isomers, and esters of such compounds, and pharmaceutically acceptable salts, solvates, and prodrugs of said compounds, tautomers, isomers, and esters, wherein each of R, $R^1$, X, Y, Z, $R^2$, $R^3$, $R^4$, $R^5$, $R^6$, $R^7$, $R^8$, $R^9$, $R^{18}$, $R^{19}$ and n are selected independently and wherein:

R, $R^1$, $R^2$, X, Y, Z, and n are as defined in Formula (I);

$R^3$ is selected from H, -alkyl, -alkenyl, alkynyl, aryl, heteroaryl, and cycloalkyl,
wherein each of said -alkyl, said -alkenyl, said alkynyl, said aryl, said heteroaryl, and said cycloalkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^4$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —$NH_2$, —NHalkyl, and —$N(alkyl)_2$,
wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^5$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —$NH_2$, —NHalkyl, and —$N(alkyl)_2$,
wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl, $R^6$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$,
  wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^7$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$,
  wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;
  or, alternatively, $R^6$ and $R^7$ are taken together with the carbon atom to which they are shown attached to form a 3- to 7-membered, saturated or partially unsaturated, spirocycloalkyl ring containing from 0 to 3 spiro ring heteroatoms selected from O, N, and S;

$R^8$ is selected from is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$,
  wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

$R^9$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$,
  wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R$^{10}$R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

each $R^{18}$ (when present) is independently selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$,
  wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each $R^{19}$ (when present) is independently selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$,
  wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each $R^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{10}$ and $R^{11}$ are linked together with the nitrogen to which they are attached to form an unsubstituted or substituted 4- or 6-membered heterocycloalkyl;

each $R^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{12}$ and $R^{13}$ are linked together with the nitrogen to which they are attached to form an unsubstituted or substituted 4- to 6-membered heterocycloalkyl;

each $R^{14}$ is independently selected from alkyl, alkoxy, alkenyl, haloalkyl, heteroalkyl, heterohaloalkyl, alkylamino, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said arylalkyl-, each said heteroaryl, and each said heteroaryl-alkyl-, is unsubstituted or optionally independently substituted with from one to five substituents, which can be the same or different, each substituent being independently selected from halo, —OH, —NH$_2$, —NHalkyl, —N(alkyl)$_2$, alkyl, alkoxy, haloalkyl, haloalkoxy, heteroaryl, heteroalkyl, and heterohaloalkyl;

each $R^{15}$ is independently selected from alkyl, alkoxy, alkenyl, haloalkyl, heteroalkyl, heterohaloalkyl, alkylamino, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said arylalkyl-, each said heteroaryl, and each said heteroaryl-alkyl-, is unsubstituted or optionally independently substituted with from one to five substituents, which can be the same or different, each substituent being independently selected from halo, —OH, —NH$_2$, —NHalkyl, —N(alkyl)$_2$, alkyl, alkoxy, haloalkyl, haloalkoxy, heteroaryl, heteroalkyl, and heterohaloalkyl;

or, alternatively, $R^{14}$ and $R^{15}$ are linked together with the nitrogen to which they are attached to form an unsubstituted or substituted 4- to 6-membered heterocycloalkyl;

each $R^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, cycloalkyl, heterocycloalkyl, heterocycloalkenyl, aryl, and heteroaryl; and each $R^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, cycloalkyl, heterocycloalkyl, heterocycloalkenyl, aryl, and heteroaryl;

or, alternatively, $R^{16}$ and $R^{17}$ are linked together with the nitrogen to which they are attached to form an unsubstituted or substituted 4- or 6-membered heterocycloalkyl.

In one embodiment, the compounds of the invention have the structural Formula (I.a):

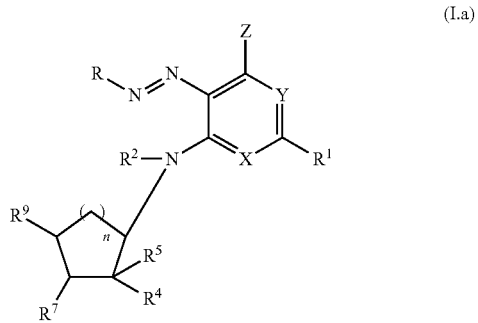

(I.a)

and includes pharmaceutically acceptable salts, esters, prodrugs, or isomers of said compounds, wherein each of R, $R^1$, X, Y, Z, $R^2$, $R^4$, $R^5$, $R^7$, and $R^9$ is selected independently and defined in Formula (I).

In one embodiment, in Formula (I.a), n is 1; $R^2$ is H; $R^4$ and $R^7$ are each independently selected from H and OH; $R^5$ is selected from H, halo, and alkyl; and $R^9$ is selected from H, —COON, —C(O)O-alkyl, —OC(O)-alkyl, —C(O)O-aryl, —OC(O)-aryl, —C(O)O-alkyl-aryl, —OC(O)-alkyl-aryl, —C(O)O-alkyl-heteroaryl, —OC(O)-alkyl-heteroaryl, alkyl, —O-alkyl, heteroalkyl, haloalkyl, heterohaloalkyl, —O-heteroalkyl, —O-haloalkyl, —O-heterohaloalkyl, -alkyl-OH, -alkyl-OC(O)-alkyl, -alkyl-OC(O)-haloalkyl, -alkyl-NH$_2$, -alkyl-NHR$^{16}$, and -alkyl-NR$^{16}$R$^{17}$.

In one embodiment, in Formula (I.a), n is 1; each of $R^2$, $R^3$, $R^5$, $R^6$, $R^8$, $R^{18}$ and $R^{19}$ is H; $R^4$ and $R^7$ are OH; and $R^9$ is alkyl, wherein said alkyl is unsubstituted or substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —OC(O)-alkyl, —OC(O)-alkenyl, —OC(O)-haloalkyl, —OC(O)-haloalkenyl, —O(C)O—NHR$^{10}$, —O(C)O—N(R$^{10}$)R$^{11}$, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —NHS(O)$_2$R$^{10}$, —N(R$^{10}$)S(O)$_2$R$^{10}$, aryl, heteroaryl, cycloalkyl, cycloalkenyl, heterocycloalkyl, and heterocycloalkenyl.

In one embodiment, in Formula (I.a), n is 1; each of $R^2$, $R^3$, $R^5$, $R^6$, $R^8$, $R^{18}$ and $R^{19}$ is H; $R^4$ and $R^7$ are OH; and $R^9$ is alkyl, wherein said alkyl is unsubstituted or substituted with from one to five groups independently selected from —OH, halo, —CN, —NH$_2$, —NHR$^{16}$, —NR$^{16}$R$^{17}$, —NHS(O)$_2$R$^{10}$, —N(R$^{10}$)S(O)$_2$R$^{10}$, —Oalkyl, —Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$.

In one embodiment, in Formula (I.a), n is 1; each $R^2$, $R^3$, $R^5$, $R^6$, $R^8$, $R^{18}$ and $R^{19}$ is H; $R^4$ and $R^7$ are OH; and $R^9$ is methyl, wherein said methyl is unsubstituted or substituted with from one to three groups independently selected from —OH, halo, alkyl, —CN, —NH$_2$, —NHR$^{16}$, —NR$^{16}$R$^{17}$, —NHS(O)$_2$R$^{10}$, —N(R$^{10}$)S(O)$_2$R$^{10}$, -Oalkyl, -Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$.

In some embodiments, $R^9$ is -alkyl-NHS(O)$_2$R$^{10}$, wherein $R^{10}$ is selected from methyl, ethyl, and cyclopropyl.

In some embodiments, $R^9$ is selected from -alkyl—N(CH$_3$)S(O)$_2$R$^{10}$ and -alkyl-N(CH$_2$CH$_3$)S(O)$_2$R$^{10}$, wherein $R^{10}$ is selected from methyl, ethyl, and cyclopropyl.

In some embodiments, $R^9$ is -alkyl-O(C)O—NHR$^{10}$, wherein $R^{10}$ is selected from methyl, ethyl, and cyclopropyl.

In some embodiments, $R^9$ is selected from $R^9$-alkyl-O(C) O—N(CH$_3$)R$^{10}$ and —O(C)O—N(CH$_2$CH$_3$)R$^{10}$, wherein $R^{10}$ is selected from methyl, ethyl, and cyclopropyl.

In one embodiment, in Formula (I.a), n is 1; $R^2$ is H; $R^4$ and $R^7$ are each independently selected from H and OH; $R^5$ is selected from H, halo, and alkyl; and $R^9$ is selected from H, —CH$_3$, —CH$_2$—CH$_3$, —CH$_2$—OH, —CH$_2$—O-alkyl, —CH$_2$—OC(O)-alkyl, —CH$_2$—OC(O)-haloalkyl, —CH$_2$—NH$_2$, —CH$_2$—NHR$^{16}$, and —CH$_2$—NR$^{16}$R$^{17}$.

In one embodiment, in Formula (I.a), n is 1, $R^2$ is H, $R^5$ is —CH$_3$, and $R^9$ is selected from H, —CH$_3$, —CH$_2$—CH$_3$, —CH$_2$—OH, —CH$_2$—O-alkyl, —CH$_2$—OC(O)CF$_3$, —CH$_2$—NH$_2$, —CH$_2$—NHR$^{16}$, and —CH$_2$—NR$^{16}$R$^{17}$.

In one embodiment, in Formula (I.a), n is 1; $R^2$ is H; $R^4$ and $R^7$ are each —OH, $R^5$ is —CH$_3$, and $R^9$ is H.

In one embodiment, in Formula (I.a), n is 1; $R^2$ is H; $R^4$ and $R^7$ are each —OH, is selected from H and —CH$_3$, and $R^9$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$alkyl, —S-alkyl, —CN, —NH$_2$, —NHR$^{16}$, and —N(alkyl)$_2$, aryl, heteroaryl, cycloalkyl, cycloalkenyl, heterocycloalkyl, and heterocycloalkenyl.

In one embodiment, in Formula (I.a), X is N, Y is N, n is 1; $R^2$ is H; $R^4$ and $R^7$ are each —OH, $R^3$ is selected from H and —CH$_3$, and $R^9$ is selected from H , -alkyl, -alkyl-OH, -alkyl-S(O)$_2$alkyl, -alkyl-S-alkyl, haloalkyl, heteroalkyl, -alkyl-CN, -alkyl-NH$_2$, -alkyl-NHR$^{16}$, and -alkyl-N(alkyl)$_2$. In one such embodiment, each said alkyl is selected from straight or branched lower alkyl.

In one embodiment, the compounds of the invention have the structural Formula (I.a.1):

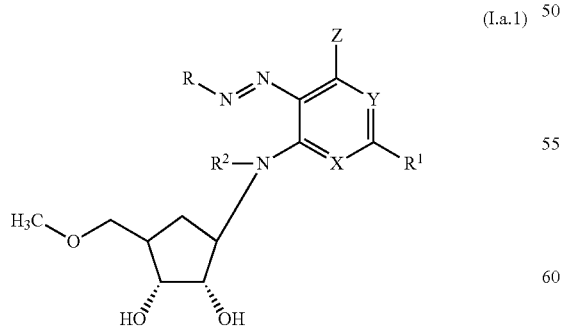

(I.a.1)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.a.1.i):

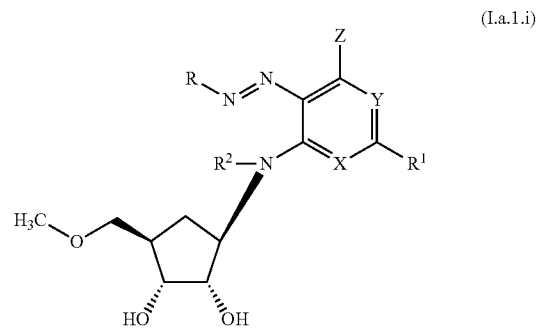

(I.a.1.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.a.2):

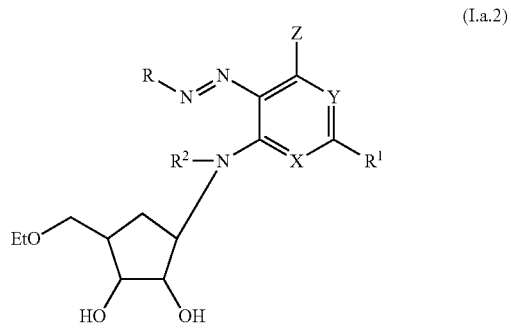

(I.a.2)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.a.2.i):

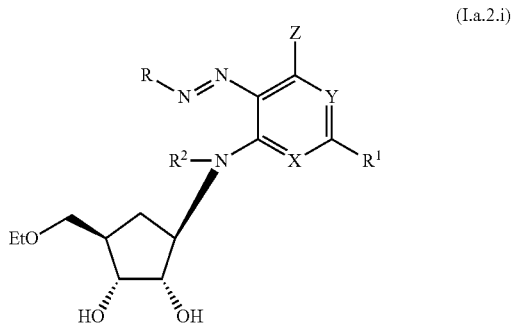

(I.a.2.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.a.3):

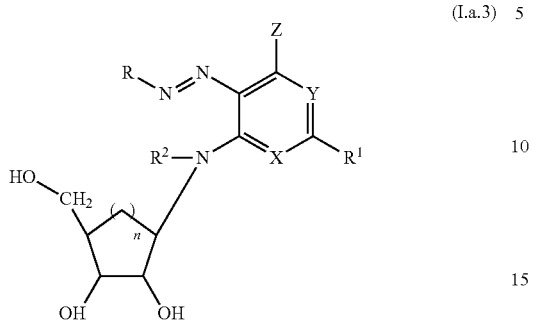
(I.a.3)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.a.3.i)

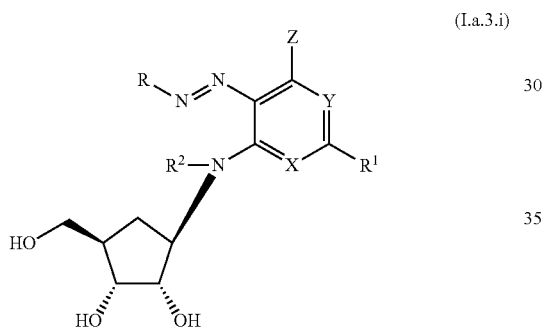
(I.a.3.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (Ia.4):

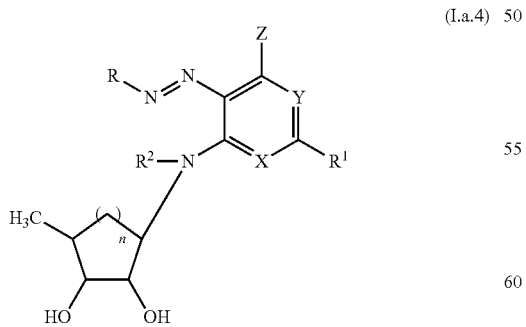
(I.a.4)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.a.4.i):

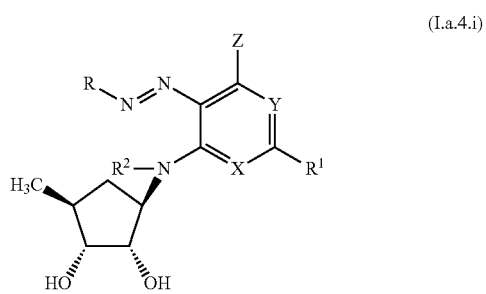
(I.a.4.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.5):

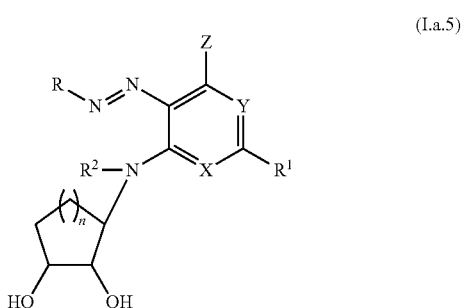
(I.a.5)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.a.5.i):

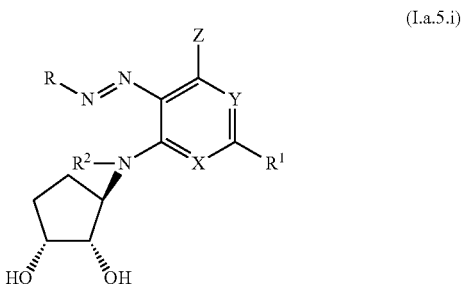
(I.a.5.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.6):

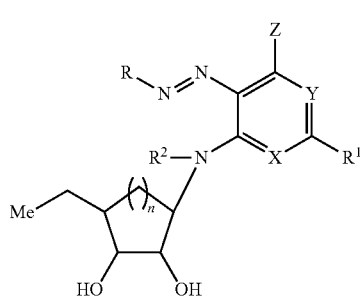

(I.a.6)

and include pharmaceutically acceptable salts, esters, prodrugs, or isomers of said compounds, wherein each of R, $R^1$, X, Y, Z, $R^2$, and n is selected independently defined in Formula (I).

In one embodiment, the compounds of the invention have the structural Formula (Ia.6.i):

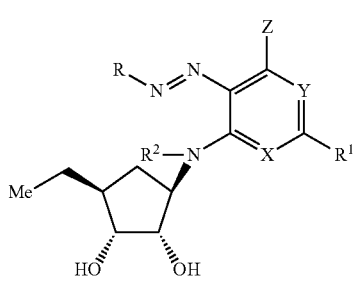

(I.a.6.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.a.7):

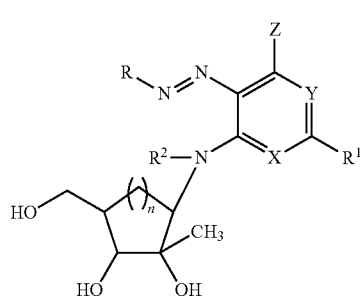

(I.a.7)

and include pharmaceutically acceptable salts, esters, prodrugs, or isomers of said compounds, wherein each of R, $R^1$, X, Y, Z, $R^2$, and n is selected independently and defined in Formula (I).

In one embodiment, the compounds of the invention have the structural Formula (I.a.7.i):

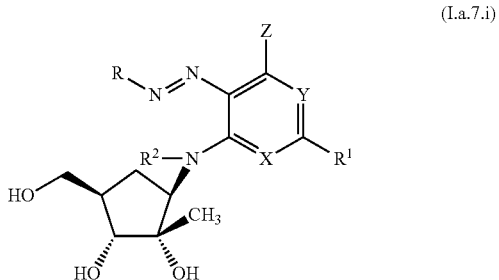

(I.a.7.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.a.8):

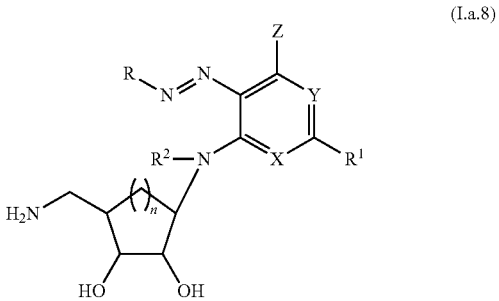

(I.a.8)

and include pharmaceutically acceptable salts, esters, prodrugs, or isomers of said compounds, wherein each of R, $R^1$, X, Y, Z, $R^2$, and n is selected independently defined in Formula (I).

In one embodiment, the compounds of the invention have the structural Formula (I.a.8.i):

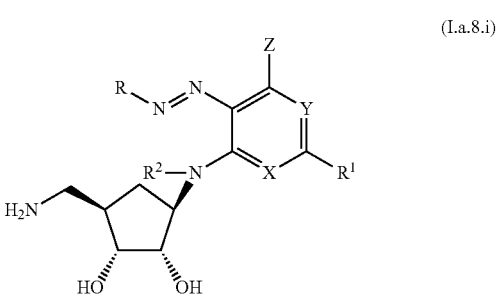

(I.a.8.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.a.9):

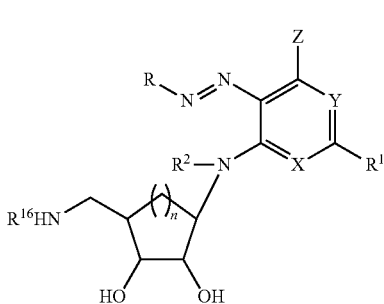
(I.a.9)

and include pharmaceutically acceptable salts, esters, prodrugs, or isomers of said compounds, wherein each of R, R¹, X, Y, Z, R², n, and R¹⁶ is selected independently defined in Formula (I).

In one embodiment, the compounds of the invention have the structural Formula (I.a.9.i):

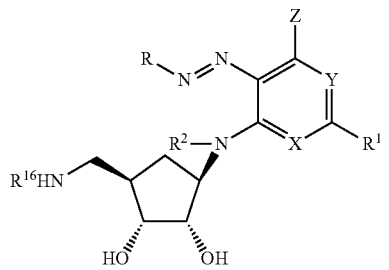
(I.a.9.i)

and include pharmaceutically acceptable salts, esters, prodrugs, or isomers of said compounds, wherein each of R, R¹, X, Y, Z, R², and R¹⁶ is selected independently and defined in Formula (I).

In one embodiment, the compounds of the invention have the structural Formula (I.a.10):

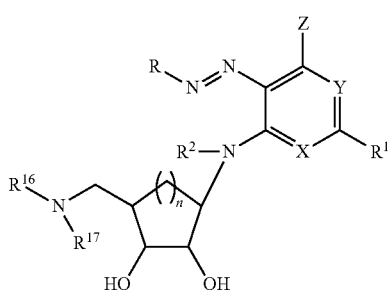
(I.a.10)

and include pharmaceutically acceptable salts, esters, prodrugs, or isomers of said compounds, wherein each of R, R¹, X, Y, Z, R², n, R¹⁶, and R¹⁷ is selected independently and defined in Formula (I).

In one embodiment, the compounds of the invention have the structural Formula (I.a.10.i):

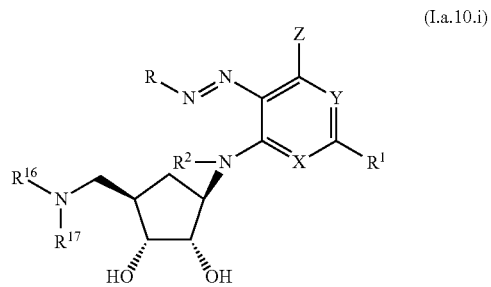
(I.a.10.i)

and include pharmaceutically acceptable salts, esters, prodrugs, or isomers of said compounds, wherein each of R, R¹, X, Y, Z, R², R¹⁶, and R¹⁷ is selected independently and defined in Formula (I).

In one embodiment, the compounds of the invention have the structural Formula (I.a.10.j):

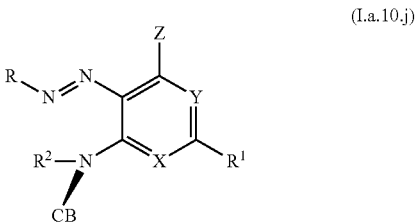
(I.a.10.j)

and include pharmaceutically acceptable salts, esters, prodrugs, or isomers of said compounds, wherein each of R, R¹, X, Y, Z, and is selected independently and defined in Formula (I), and wherein CB is a moiety selected from the group consisting of:

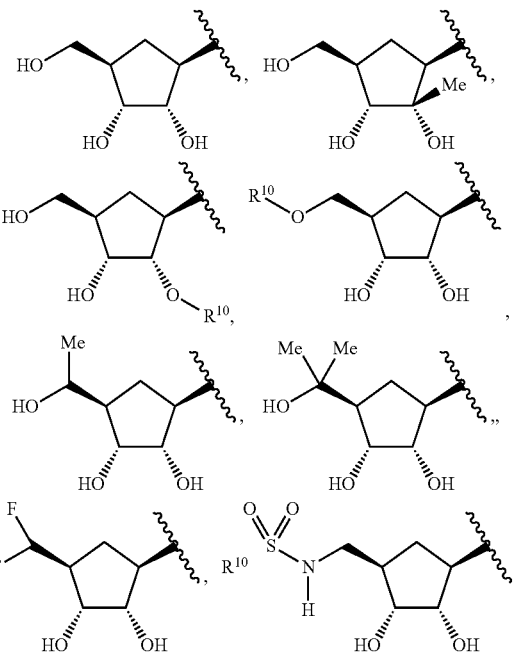

-continued

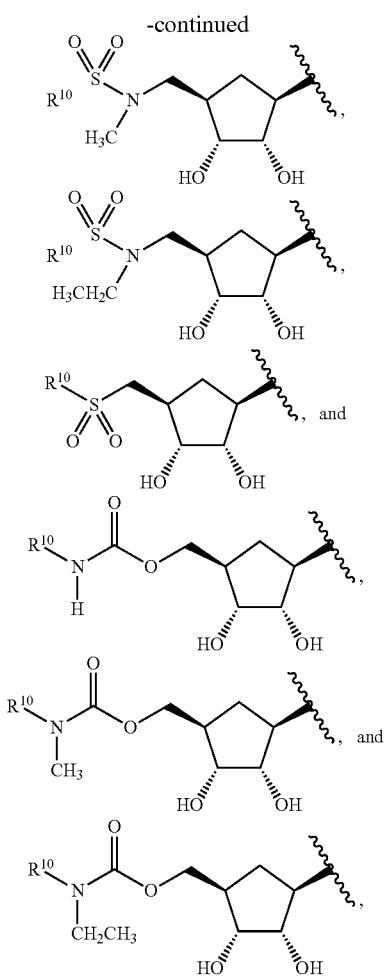

wherein each $R^{10}$ is independently selected from the group consisting of methyl, ethyl, and cyclopropyl.

In one embodiment, in Formula (I.a.10.j):
X is N; Y is N; $R^2$ is H; and Z is selected from the group consisting of H, methyl, and chloro; and R and $R^1$ are each as defined in Formula (I). In other such embodiments, R and $R^1$ are each independently as defined in any of the various emodiments described herein, or in the examples.

In one embodiment, in Formula (I.a.10.j):
X is N; Y is N;
$R^2$ is H;
Z is selected from the group consisting of H, methyl, and chloro;
R is unsubstituted phenyl or phenyl substituted with from 1 to 4 substituents independently selected from the group consisting of alkyl, alkoxy, cycloalkyl, halo, —CN, —NH$_2$, and —NO$_2$; and
$R^1$ is selected from the group consisting of —NH$_2$, —NHR$^{14}$, and —NR$^{14}$R$^{15}$, wherein R$^{14}$ and R$^{15}$ (when present) are each as defined in Formula I.

In one embodiment, in Formula (I.a.10.j):
X is N; Y is N;
$R^2$ is H;
Z is selected from the group consisting of H, methyl, and chloro;
R is unsubstituted phenyl or phenyl substituted with from 1 to 4 substituents independently selected from the group consisting of alkyl, alkoxy, cycloalkyl, halo, —CN, —NH$_2$, and —NO$_2$; and
$R^1$ is —NH$_2$.

In one embodiment, in Formula (I.a.10.j):
X is N; Y is N;
$R^2$ is H;

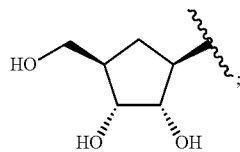

CB is a moiety having a formula:
Z is selected from the group consisting of H, methyl, and chloro;
R is unsubstituted phenyl or phenyl substituted with from 1 to 4 substituents independently selected from the group consisting of alkyl, alkoxy, cycloalkyl, halo, —CN, —NH$_2$, and —NO$_2$; and
$R^1$ is —NH$_2$.

In one embodiment, the compounds of the invention have the structural Formula (I.B):

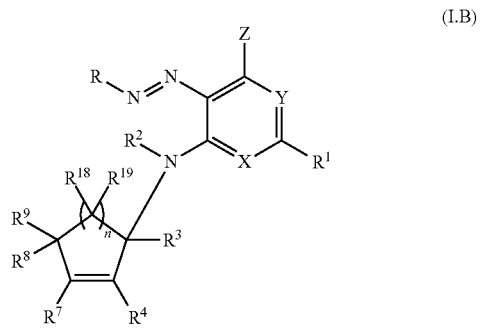

(I.B)

and includes pharmaceutically acceptable salts, esters, prodrugs, or isomers of said compounds, wherein each of R, $R^1$, X, Y, Z, $R^2$, $R^3$, $R^4$, $R^7$, $R^8$, $R^9$, $R^{18}$, $R^{19}$, and n is selected independently and defined in Formula (I).

In one embodiment, the compounds of the invention have the structural Formula (I.b):

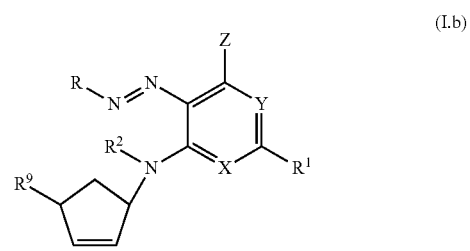

(I.b)

and includes pharmaceutically acceptable salts, esters, prodrugs, or isomers of said compounds, wherein each of R, $R^1$, X, Y, Z, $R^2$, and $R^9$ is selected independently and defined in Formula (I).

In one embodiment, in Formula (I.b), $R^2$ is H, and $R^9$ is selected from H, —CH$_3$, —CH$_2$—O-alkyl, —CH$_2$—OH, —CH$_2$—OC(O)-alkyl, —CH$_2$—OC(O)-haloalkyl, —CH$_2$—CH$_3$, —CH$_2$—NH$_2$, —CH$_2$—NHR$^{16}$, and —CH$_2$—NR$^{16}$R$^{17}$.

In one embodiment, in Formula (I.b), $R^2$ is H, and $R^9$ is selected from —$CH_2$—O-alkyl, and —$CH_2$—OH.

In one embodiment, the compounds of the invention have the structural Formula (I.b.1):

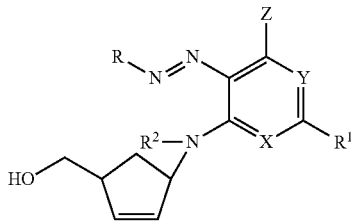

(I.b.1)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.b.1.i):

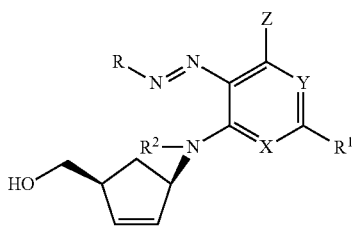

(I.b.1.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.b.2):

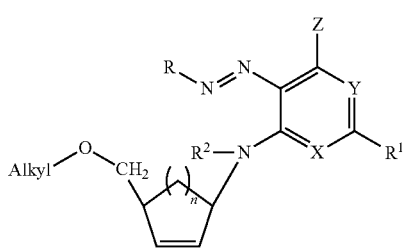

(I.b.2)

and include pharmaceutically acceptable salts, esters, prodrugs, or isomers of said compounds, wherein each of R, $R^1$, X, Y, Z, $R^2$, and n is selected independently and defined in Formula (I).

In one embodiment, the compounds of the invention have the Formula (I.b.2.i):

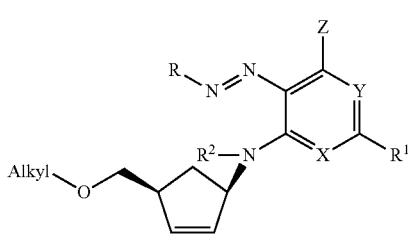

(I.b.2.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.C):

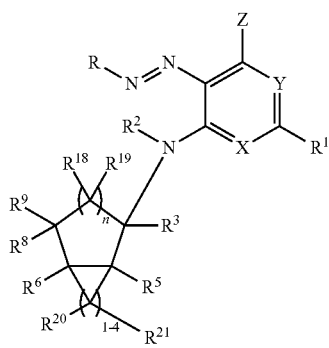

(I.C)

and includes pharmaceutically acceptable salts, esters, prodrugs, or isomers of said compounds, wherein each of R, $R^1$, X, Y, Z, $R^2$, $R^3$, $R^5$, $R^6$, $R^8$, $R^9$, $R^{18}$, $R^{19}$, $R^{20}$, $R^{21}$, and n is selected independently and defined in Formula (I), with the proviso that $R^5$ and $R^6$ are not taken together to form a double bond.

In one embodiment, the compounds of the invention have the structural Formula (I.c):

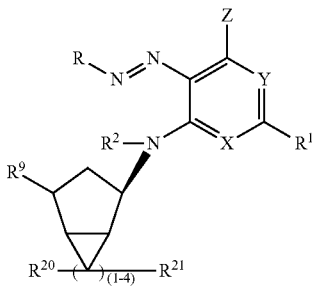

(I.c)

and include pharmaceutically acceptable salts, esters, prodrugs, or isomers of said compounds, wherein each of R, $R^1$, X, Y, Z, $R^2$, $R^9$, $R^{20}$, and $R^{21}$ is selected independently and defined in Formula (I).

In one embodiment, in Formula (I.c), $R^2$ is H; $R^9$ is selected from H, —$CH_3$, —$CH_2$—O-alkyl, —$CH_2$—OH, —$CH_2$—OC(O)-alkyl, —$CH_2$—OC(O)-haloalkyl, —$CH_2$—$CH_3$,—$CH_2$—$NH_2$, —$CH_2$—$NHR^{16}$, and —$CH_2$—$NR^{16}R^{17}$; and each of $R^{20}$ and $R^{21}$ is independently selected from H and —$CH_3$.

In one embodiment, the compounds of the invention have the structural Formula (I.c.1):

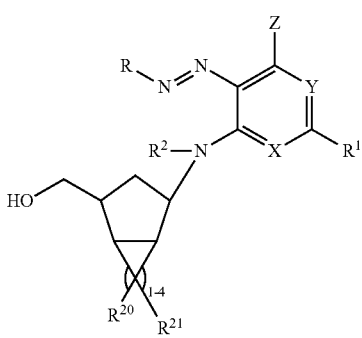

(I.c.1)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.c.1.i):

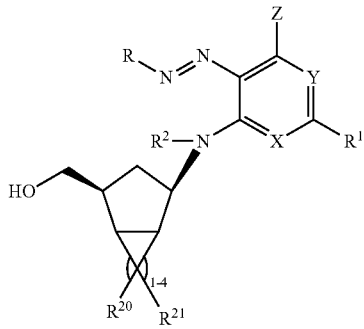

(I.c.1.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.c.2):

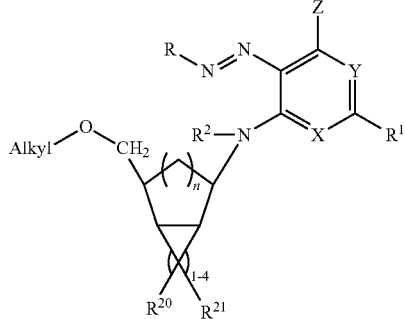

(I.c.2)

and include pharmaceutically acceptable salts, esters, prodrugs, or isomers of said compounds, wherein each of R, $R^1$, X, Y, Z, $R^2$, and n is selected independently and defined in Formula (I).

In one embodiment, the compounds of the invention have the structural Formula (I.c.2.i):

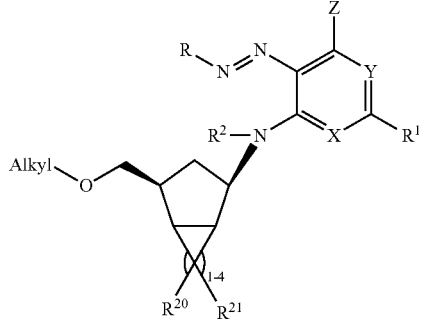

(I.c.2.i)

and include pharmaceutically acceptable salts, esters, prodrugs, or isomers of said compounds, wherein each of R, $R^1$, X, Y, Z, and $R^2$ is selected independently defined in Formula (I).

In one embodiment, the compounds of the invention have the structural Formula (I.D):

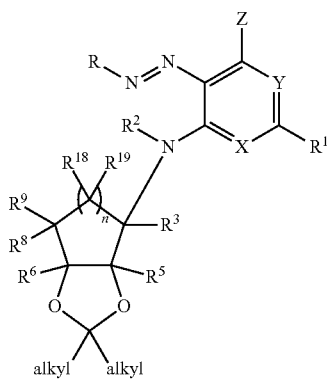

(I.D)

and includes pharmaceutically acceptable salts, esters, prodrugs, or isomers of said compounds, wherein each of R, $R^1$, X, Y, Z, $R^2$, $R^3$, $R^5$, $R^6$, $R^8$, $R^9$, $R^{18}$, and $R^{19}$, and n is selected independently and defined in Formula (I).

In one embodiment, the compounds of the invention have the structural Formula (I.d):

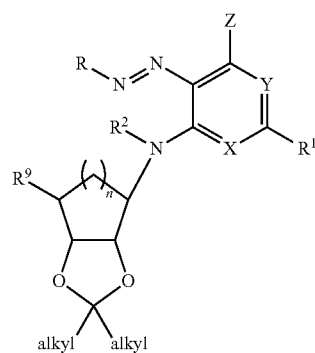

(I.d)

and includes pharmaceutically acceptable salts, esters, prodrugs, or isomers of said compounds, wherein each of R, $R^1$, X, Y, Z, $R^2$, $R^9$, and n is selected independently and defined in Formula (I).

In one embodiment, in Formula (I.d), n is 1 and $R^9$ is selected from H, —$CH_3$, —$CH_2$—O-alkyl, —$CH_2$—OH, —$CH_2$—OC(O)-alkyl, —$CH_2$—OC(O)-haloalkyl, —$CH_2$—$CH_3$, —$CH_2$—$NH_2$, —$CH_2$—$NHR^{16}$, and —$CH_2$—$NR^{16}R^{17}$.

In one embodiment, in Formula (I.d), n is 1 and $R^9$ is selected from —$CH_2$—O-alkyl, and —$CH_2$—OH.

In one embodiment, the compounds of the invention have the structural Formula (I.d.1):

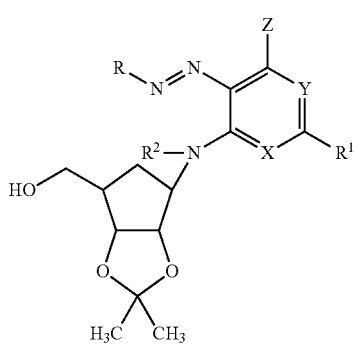

(I.d.1)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.d.1.i):

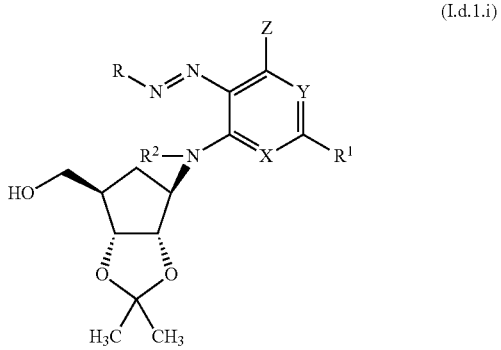
(I.d.1.i)

and include pharmaceutically acceptable salts, esters, prodrugs, or isomers of said compounds, wherein each of R, $R^1$, X, Y, Z, and $R^2$ is selected independently and defined in Formula (I).

In one embodiment, the compounds of the invention have the structural Formula (I.E):

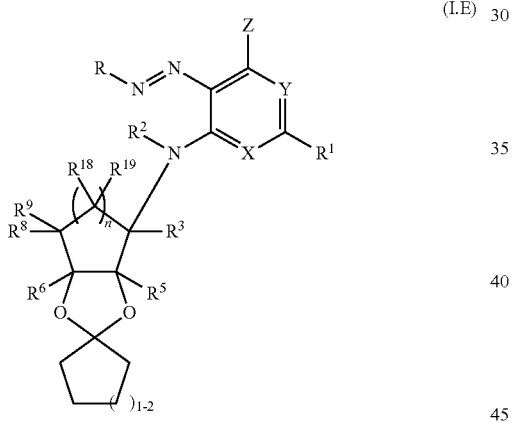
(I.E)

and includes pharmaceutically acceptable salts, esters, prodrugs, or isomers of said compounds, wherein each of R, $R^1$, X, Y, Z, $R^2$, $R^3$, $R^5$, $R^6$, $R^8$, $R^9$, $R^{18}$, and $R^{19}$, and n is selected independently and defined in Formula (I).

In one embodiment, the compounds of the invention have the structural Formula (II):

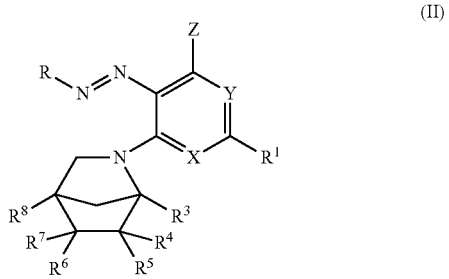
(II)

and include pharmaceutically acceptable salts, esters, prodrugs, or isomers of said compounds, wherein each of R, $R^1$, X, Y, Z, $R^3$, $R^4$, $R^5$, $R^6$, $R^7$, and $R^8$ is selected independently and defined in Formula (I).

In one embodiment, the compounds of the invention have the structural Formula (II):

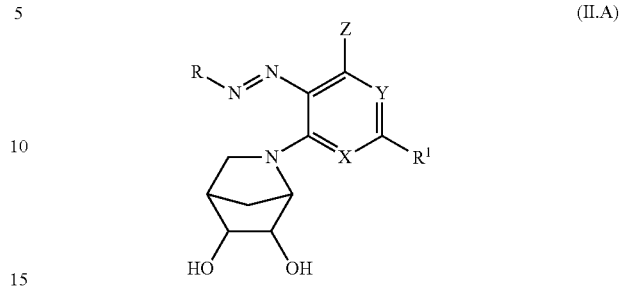
(II.A)

and include pharmaceutically acceptable salts, esters, prodrugs, or isomers of said compounds, wherein each of R, $R^1$, X, Y, and Z is selected independently and wherein R, $R^1$, X, Y, and Z are defined in Formula (I).

In one embodiment, in Formula (I), the compounds of the invention have the structural Formula (II.a.1):

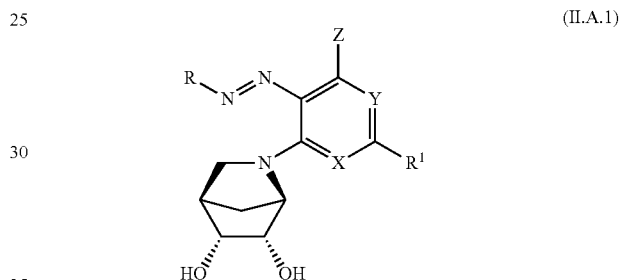
(II.A.1)

and include pharmaceutically acceptable salts, esters, prodrugs, or isomers of said compounds, wherein each of R, $R^1$, X, Y, and Z is selected independently and wherein R, $R^1$, X, Y, and Z are defined in Formula (I).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.2), (I.c.2.i), (I.D), (I.d), (I.d.1), (I.d.1.i), (I.E), (II), (II.A), and (II.A.1), X is N and Y is N.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), X is N and Y is CH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), X is CH and Y is N.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from aryl, heteroaryl, benzo-fused heteroaryl, cycloalkyl, cycloalkenyl, benzo-fused cycloalkyl, benzo-fused cycloalkenyl, heterocycloalkyl, and benzo-fused heterocycloalkyl,
   wherein each of said alkyl, said aryl, said heteroaryl, said benzo-fused heteroaryl, said cycloalkyl, said cycloalkenyl, said heterocycloalkyl, said heterocycloaklenyl, and said benzo-fused heterocycloalkyl is unsubstituted or optionally independently substituted with from one to three substituents, which are the same or different, each substituent being independently selected from halo, —OH, —CN, alkyl, alkenyl, alkynyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from the group consisting of substituted or unsubstituted aryl, substituted or unsubstituted heteroaryl, and substituted or unsubstituted benzo-fused heteroaryl, each of said substituents being independently selected from the group consisting of alkyl and —O-alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from substituted alkynyl, substituted alkynyl, unsubstituted aryl, substituted aryl, unsubstituted cycloalkyl, substituted cycloalkyl, unsubstituted benzo-fused cycloalkyl, substituted benzo-fused cycloalkyl, unsubstituted cycloalkenyl, and substituted cycloalkenyl, which substituents, when present, are as defined in Formula (I).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (I.A), and (II.A.1), R is unsubstituted aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.1), (I.b.2), (I.b.2.i), (I.C), (I.c), (I.c.1), (I.c.1.i), (I.c.2), (I.c.2.1), (I.D), (I.d), (I.d.1), (I.d.1.i), (I.E), (II), (II.A), and (II.A.1), R is unsubstituted benzo-fused cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted benzo-fused cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted cycloalkenyl.

In other embodiments, in each of Formulas (I), (I.A), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted cycloalkenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from unsubstituted heteroaryl, substituted heteroaryl, unsubstituted benzo-fused heteroaryl, substituted benzo-fused heteroaryl, unsubstituted heterocycloalkyl, substituted heterocycloalkyl, unsubstituted benzo-fused heterocycloalkyl, substituted benzo-fused heterocycloalkyl, unsubstituted heterocycloalkenyl, and unsubstituted heterocycloalkenyl, which substituents, when present, are as defined in Formula (I).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1 (I.E), (II), (II.A), and (II.A.1), R is unsubstituted heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted benzo-fused heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted benzo-fused heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c) (I.c.1), (I.c.1.i), (I.c.2), (I.c.2.i), (I.D), (I.d), (I.d.1), (I.d.1.i), (I.E), (II), (II.A), and (II.A.1), R is unsubstituted heterocycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted heterocycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.0, (I.a.10.j), (I.B), (I.b), (I.b.1), (I.b.1.i), (I.b.2), (I.b.2.i), (I.C), (I.c), (I.c.1), (Lei .i), (I.c.2), (I.c.2.i), (I.D), (I.d), (I.d.1), (I.d.1.i), (I.E), (II), (II.A), and (II.A.1), R is unsubstituted benzo-fused heterocycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted benzo-fused heterocycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted heterocycloalkenyl.

In other embodiments, in each of Formulas (I), (I.A), (I.a), (I.a.1), (I.a.1.i), (I.a.2), (I.a.2.i), (I.a.3), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted heterocycloalkenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is an unsubstituted or substituted monocyclic aryl moiety or an unsubstituted or substituted heteroaryl moiety. Non-limiting examples of such unsubstituted or substituted monocyclic aryl moiety or unsubstituted or substituted heteroaryl moiety include:

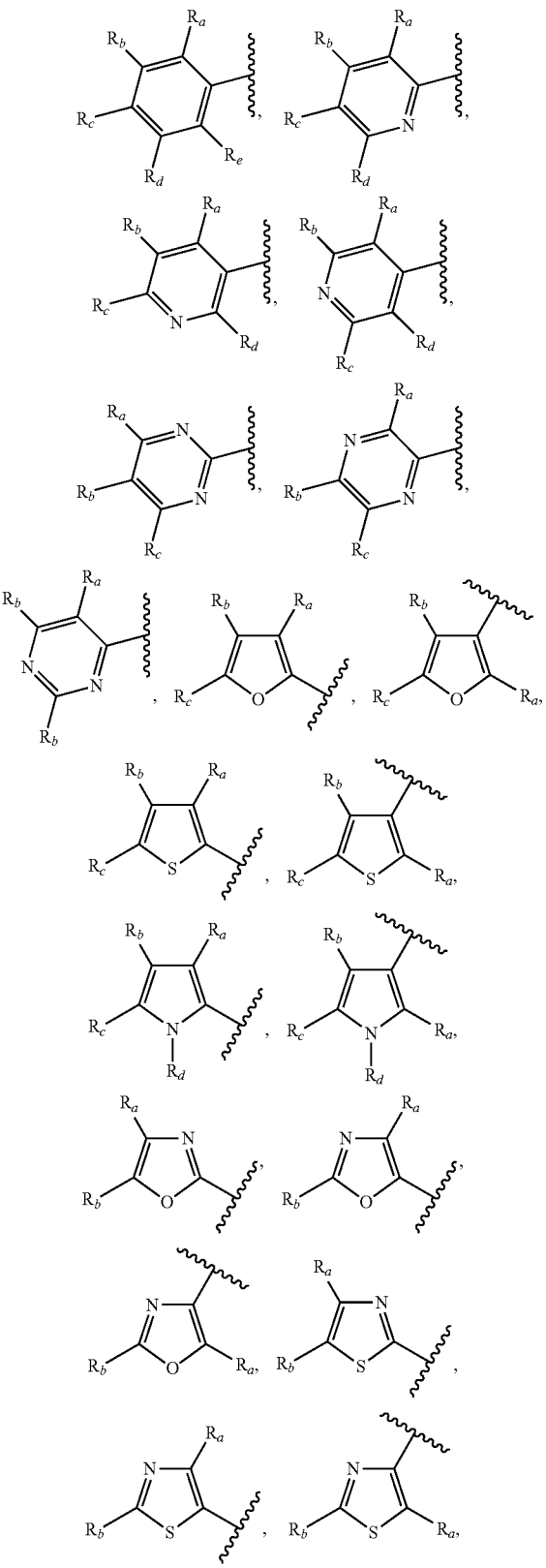

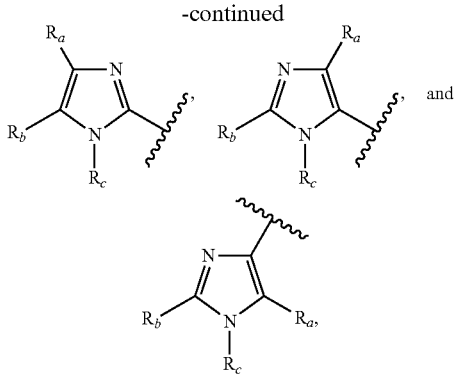

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is an unsubstituted or an substituted bicyclic heteroaryl moiety. Non-limiting examples of such unsubstituted or substituted bicyclic heteroaryl moieties include:

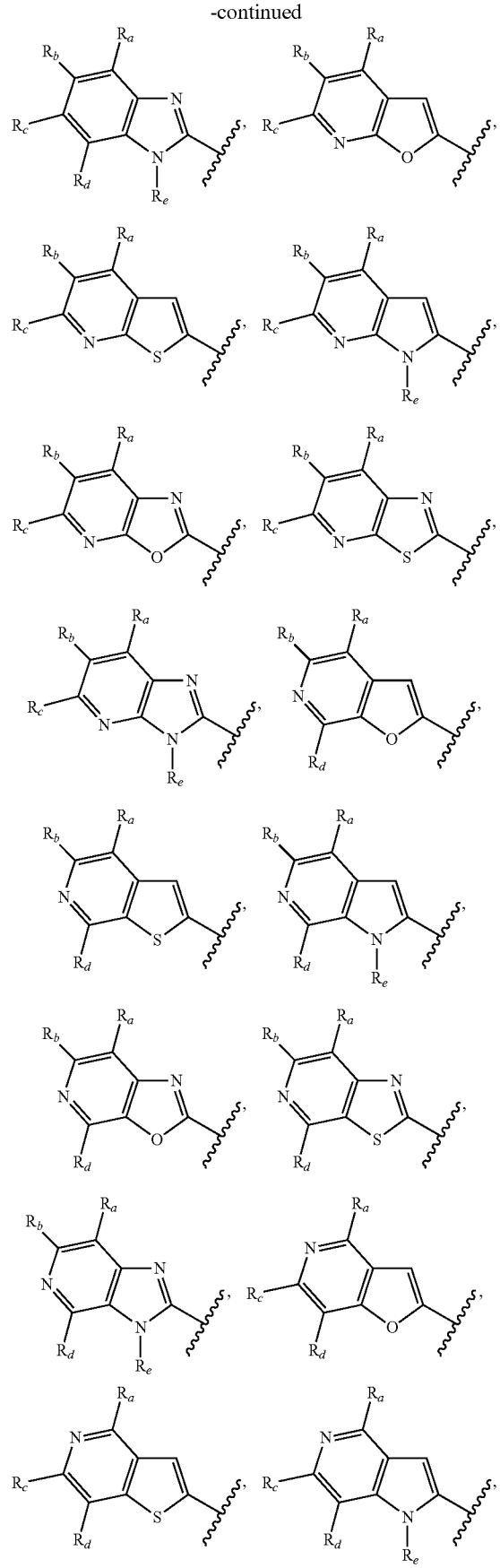

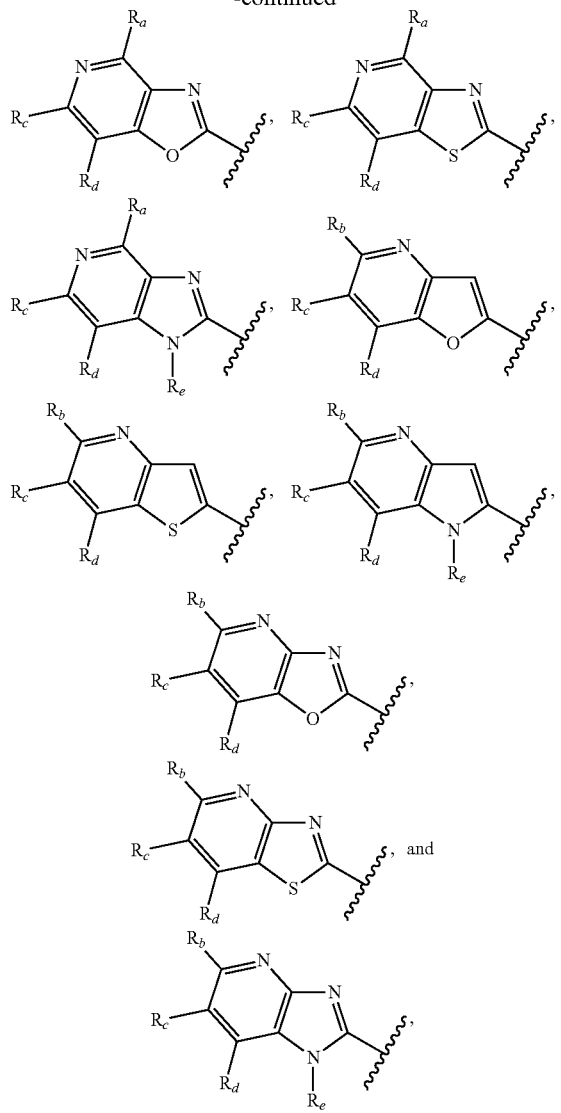

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of halo, alkyl, haloalkyl, cycloalkyl, and —NH$_2$. Non-limiting examples of Z when Z is cycloalkyl include cyclopropyl. Non-limiting examples of Z when Z is haloalkyl include fluoroalkyl (up to perfluoroalkyl).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of halo, alkyl, and cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is H.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is halo.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —Cl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —F.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —OH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —SH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —S alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —S—CH₃.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c) (I.c.1), (I.c.1.i), (I.c.2), (I.c.2.i), (I.D), (I.d), (I.d.1), (I.d.1.i), (I.E), (II), (II.A), and (II.A.1), Z is -alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (IC), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CH₃.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CH₂CH₃.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c) (I.c.1), (I.c.1.i), (I.c.2), (I.c.2.i), (I.D), (I.d), (I.d.1), (I.d.1.i), (I.E), (II), (II.A), and (II.A.1), Z is —OCH₃.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is -haloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CF₃.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CHF₂.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CH₂F.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is cyclopropyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is phenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-thiophenyl.

In other embodiments, in each of Formulas (I), (I.A), (I.a), (I.a.1), (I.a.1.i), (I.a.2), (I.a.2.i), (I.a.3), (I.a.3.1), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 3-thiophenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-thiazolyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-oxazolyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-pyrimidinyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-pyridyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-pyrazinyl.

In other embodiments, in each of Formulas (I), (I.A), (I.a), (I.a.1), (I.a.1.i), (I.a.2), (I.a.2.i), (I.a.3), (I.a.3.i), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-imidazolyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —$NH_2$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —$NHR^{12}$.

In other embodiments, in each of Formulas (I), (I.A), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —$NR^{12}R^{13}$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of Cl and methyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10 j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is selected from the group consisting of —$NH_2$, —$NHR^{14}$, and —$NR^{14}R^{15}$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is selected from the group consisting of —$NH_2$ and —$NHR^{14}$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is H.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10 j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1) (I.d.1.i), (I.E), (II), (II.A), and (II.A.1), $R^1$ is halo.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.E), (II), (II.A), and (II.A.1), $R^1$ is Cl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is F.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —$CH_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —$CH_2CH_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is heteroalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.1), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —OH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-alkyl.

In other embodiments, in each of Formulas (I), (I.A), (I.a), (I.a.1), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10 j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-heteroalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10 j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —SH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10 j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —S-alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.5), (I.a.5.i), (I.a.6), (I.a.6.i), (I.a.7), (I.a.7.i), (I.a.8), (I.a.10), (I.a.10.i), (I.a.10.j), (I.B), (I.b), (I.b.1), (I.b.1.i), (I.b.2), (I.b.2.), (I.C), (I.c), (I.c.1), (I.c.1.i), (I.c.2), (I.c.2.i), (I.D), (I.d), (I.d.1), (I.d.1.1), (I.E), (II), (II.A), and (II.A.1), $R^1$ is —S-aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.1), (I.b.2), (I.b.2.i), (I.C), (I.c), (I.c.1), (I.c.1.i), (I.c.2), (I.c.2.i), (I.D), (I.d), (I.d.1), (I.d.1.1), (I.E), (II), (II.A), and (II.A.1), $R^1$ is —S-heteroalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —S-heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —NH$_2$.

In other embodiments, in each of Formulas (I), (I.A), (I.a), (I.a.1), (I.a.1.i), (I.a.2), (I.a.2.0i), (I.a.3), (I.a.3.i), (I.a.4), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —NHR$^{14}$. Non-limiting examples of $R^1$ when $R^1$ is —NHR$^{14}$ include:

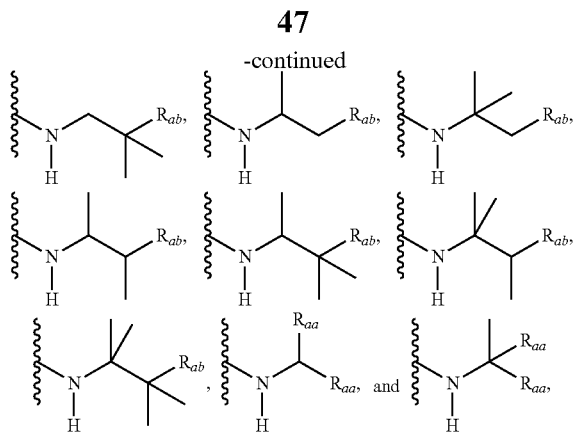

wherein the wavy line represents the point of attachment of $R^1$ to the rest of the molecule, and wherein each $R_{aa}$ is independently selected from haloalkyl (non-limiting examples of which include —$CH_2F$, —$CHF_2$, —$CF_3$, etc.), $R_{ab}$ is selected from OH, OAc, and —O-alkyl (non-limiting examples of which include —O-Me, —O-Et, —O-n-Pr, —O-i-Pr, —O-n-Bu, —O-i-Bu, and —O-t-Bu), —O-haloalkyl (non-limiting examples of which include —O—$CH_2F$, —O—$CHF_2$, and —O—$CF_3$), —$NH_2$, —NHalkyl, and —N(alkyl)$_2$.

Additional non-limiting examples of $R^1$ when $R^1$ is —$NHR^{14}$ include:

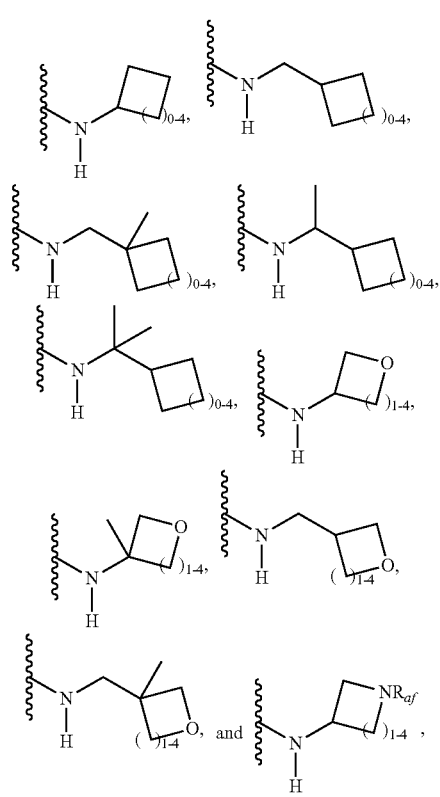

wherein the wavy line represents the point of attachment of $R^1$ to the rest of the molecule, and wherein $R_{af}$ is selected from H and acetyl. It shall be understood that positional isomers of the heteroatoms shown in the moieties above are also contemplated. Such positional isomers include symmetric positional isomers such as

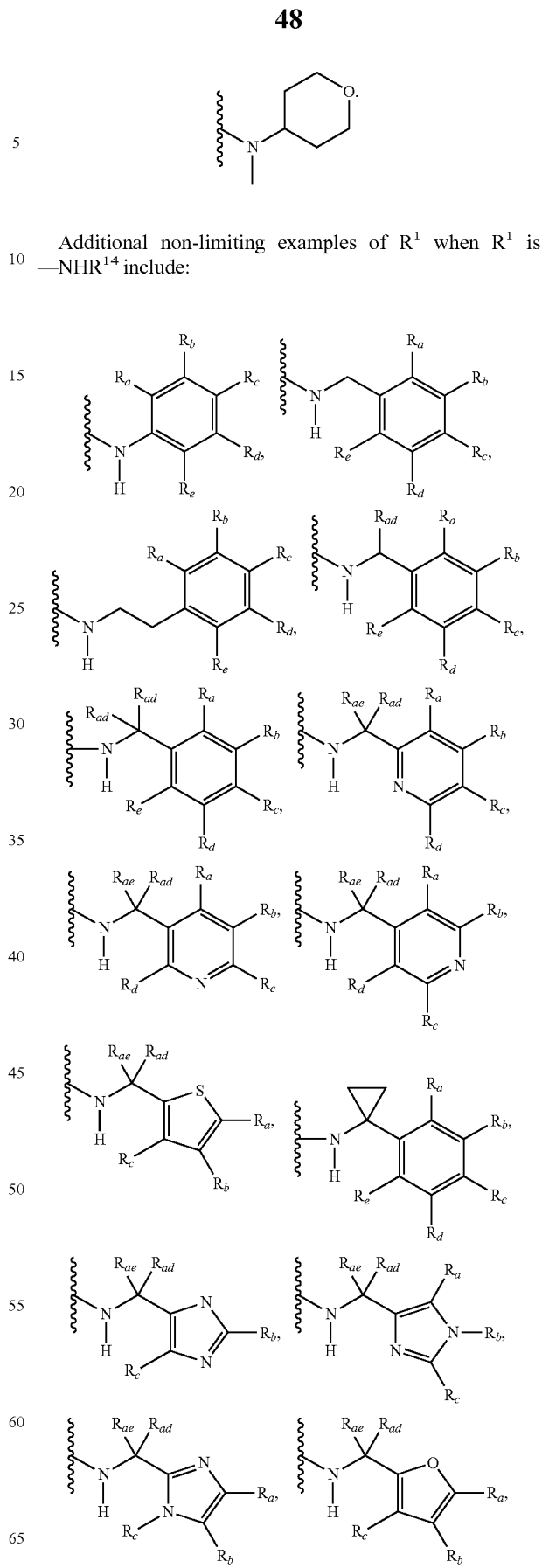

Additional non-limiting examples of $R^1$ when $R^1$ is —$NHR^{14}$ include:

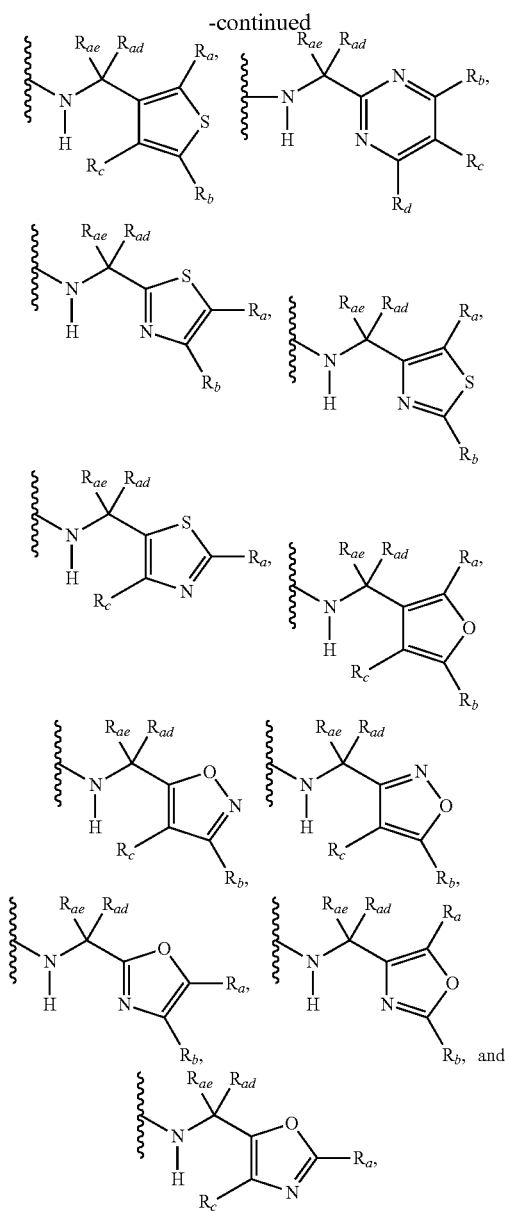

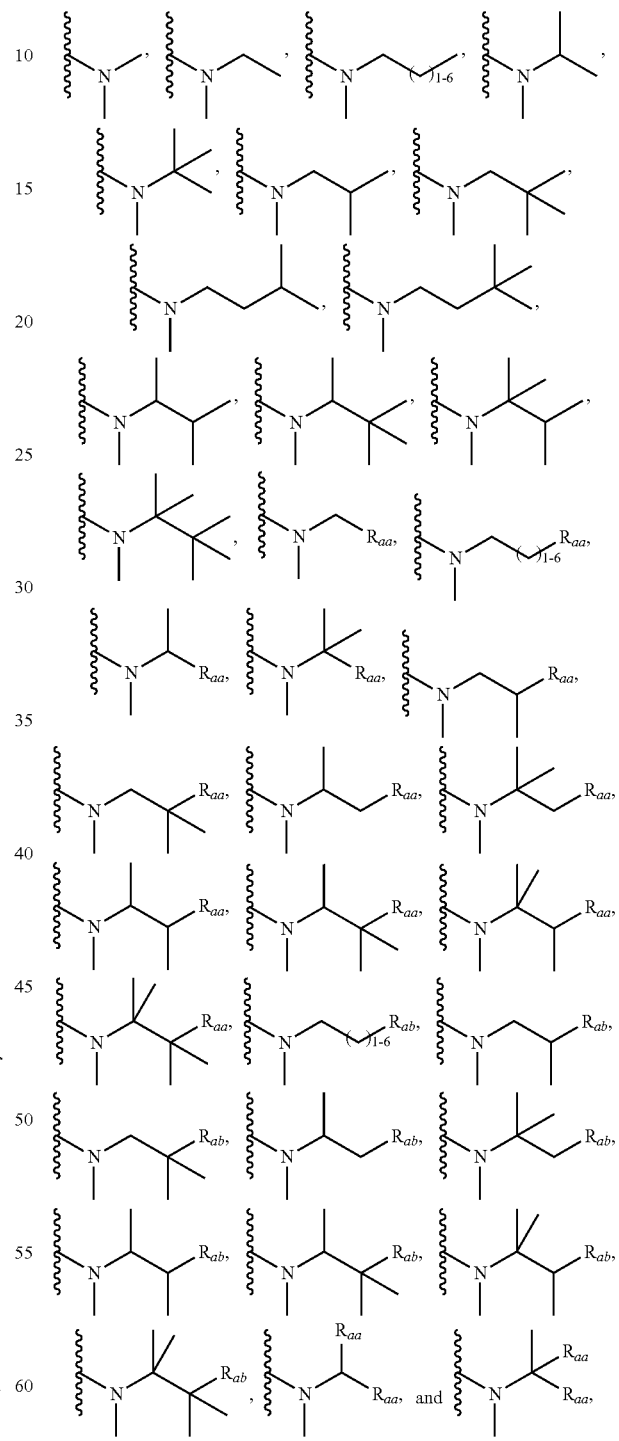

wherein the wavy line represents the point of attachment of $R^1$ to the rest of the molecule, and wherein each of $R_a$, $R_b$, $R_e$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and wherein each $R_{ad}$ and each $R_{ae}$ is independently selected from alkyl and haloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —NR$^{14}$R$^{15}$. Non-limiting examples of $R^1$ when $R^1$ is —NR$^{14}$R$^{15}$ include:

wherein the wavy line represents the point of attachment of $R^1$ to the rest of the molecule, and wherein each $R_{aa}$ is independently selected from haloalkyl (non-limiting examples of which include —CH$_2$F, —CHF$_2$, —CF$_3$, etc.), $R_{ab}$ is selected from OH, OAc, and —O-alkyl (non-limiting examples of which include —O-Me, —O-Et, —O-n-Pr, —O-i-Pr, —O-n-Bu, —O-i-Bu, and —O-t-Bu), —O-haloalkyl (non-limiting examples of which include —O—CH$_2$F, —O—CHF$_2$, and —O—CF$_3$), —NH$_2$, —NHalkyl, and —N(alkyl)$_2$.

Additional non-limiting examples of $R^1$ when $R^1$ is —NR$^{14}$R$^{15}$ include:

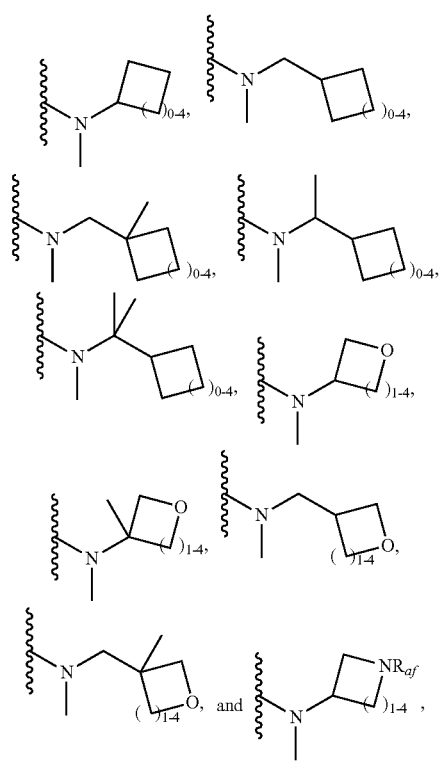

wherein the wavy line represents the point of attachment of $R^1$ to the rest of the molecule, and wherein $R_{af}$ is selected from H and acetyl. It shall be understood that positional isomers of the heteroatoms shown in the moieties above are also contemplated. Such positional isomers include symmetric positional isomers such as

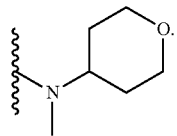

Additional non-limiting examples of $R^1$ when $R^1$ is —NR$^{14}$R$^{15}$ include:

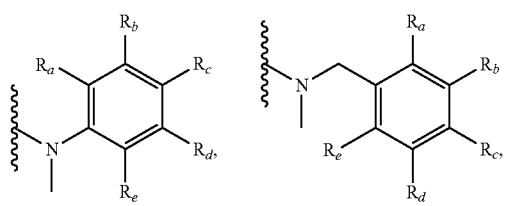

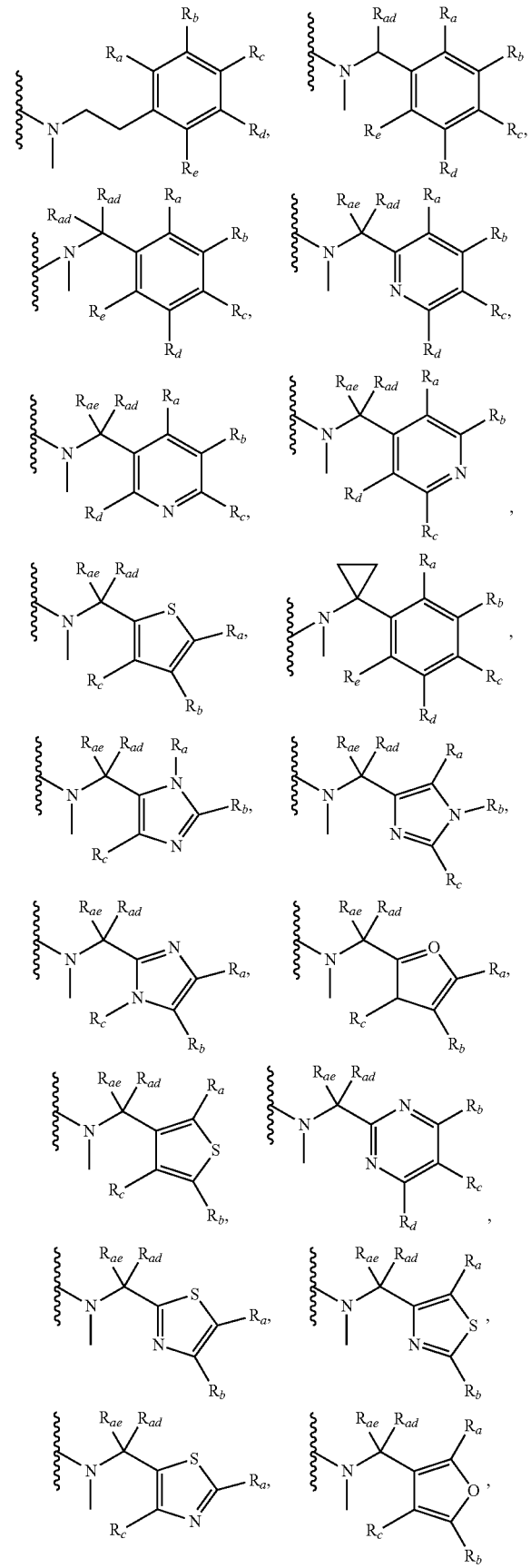

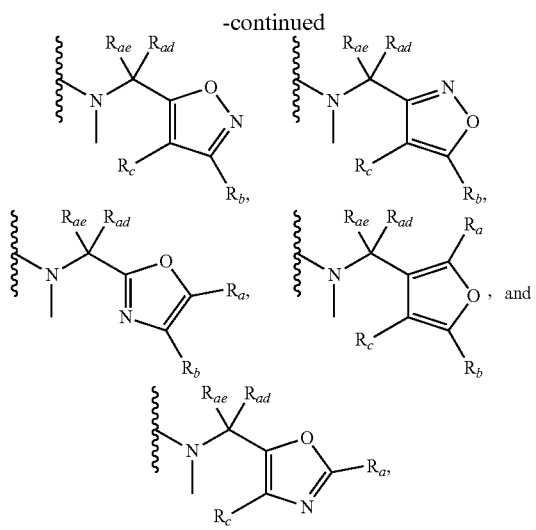

wherein the wavy line represents the point of attachment of R¹ to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, -alkyl, and —C(O)Oalkyl, and wherein each $R_{ad}$ and each $R_{ae}$ is independently selected from alkyl and haloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R¹ is —NR$^{14}$R$^{15}$, wherein R$^{14}$ and R$^{15}$ are linked together with the nitrogen to which they are attached to form an unsubstituted or substituted 4- to 6-membered heterocycloalkyl. Non-limiting examples of R¹ when R¹ is —NR$^{14}$R$^{15}$ and R$^{14}$ and R$^{15}$ are so linked include:

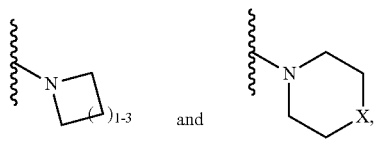

wherein X is selected from O, NH, and NMe.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1):

R is selected from aryl, heteroaryl, benzo-fused heteroaryl, cycloalkyl, cycloalkenyl, benzo-fused cycloalkyl, benzo-fused cycloalkenyl, heterocycloalkyl, and benzo-fused heterocycloalkyl, wherein each of said alkyl, said aryl, said heteroaryl, said benzo-fused heteroaryl, said cycloalkyl, said cycloalkenyl, said heterocycloalkyl, said heterocycloaklenyl, and said benzo-fused heterocycloalkyl is unsubstituted or optionally independently substituted with from one to three substituents, which are the same or different, each substituent being independently selected from halo, —OH, —CN, alkyl, cycloalkyl, alkenyl, alkynyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

R¹ is selected from —NH$_2$, —NHR$^{14}$, and —NR$^{14}$R$^{15}$; and

Z is selected from H, halo, alkyl, —OH, haloalkyl, and cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1):

R is

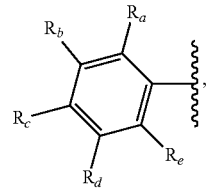

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

R¹ is selected from —NH$_2$, —NHR$^{14}$, and —NR$^{14}$R$^{15}$; and

Z is selected from H, halo, alkyl, —OH, haloalkyl, and cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is halo; $R^1$ is selected from —$NH_2$, —$NHR^{14}$, and —$NR^{14}R^{15}$; and R is as defined in claim 1.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is heteroaryl; $R^1$ is selected from —$NH_2$, —$NHR^{14}$, and —$NR^{14}R^{15}$; and R is as defined in claim 1.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is H; $R^1$ is selected from —$NH_2$, —$NHR^{14}$, and —$NR^{14}R^{15}$; and R is as defined in claim 1.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is alkyl; $R^1$ is selected from —$NH_2$, —$NHR^{14}$, and —$NR^{14}R^{15}$; and R is as defined in claim 1.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is halo; $R^1$ is selected from —$NH_2$, —$NHR^{14}$, and —$NR^{14}R^{15}$; and R is heteroaryl.

In other embodiments, in each of Formulas (I), (I.A), (I.a), (I.a.1), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is heteroaryl; $R^1$ is selected from —$NH_2$, —$NHR^{14}$, and —$NR^{14}R^{15}$; and R is heteroaryl.

In other embodiments, in each of Formulas (I), (I.A), (I.a), (I.a.1), (I.a.1.i), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is H; $R^1$ is selected from —$NH_2$, —$NHR^{14}$, and —$NR^{14}R^{15}$; and R is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is alkyl; $R^1$ is selected from —$NH_2$, —$NHR^{14}$, and —$NR^{14}R^{15}$; and R is heteroaryl.

In other embodiments, in each of Formulas (I), (I.A), (I.a), (I.ai), (I.a.1.i), (I.a.2), (I.a.2.i), (I.a.3), (I.a.3.i), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.2), (I.c.2.i), (I.D), (I.d), (I.d.1), (I.d.1.i), (I.E), (II), (II.A), and (II.A.1), X and Y are each N; R is selected from unsubstituted aryl, substituted aryl, unsubstituted heteroaryl, and substituted heteroaryl, wherein said substituents, when present, are defined in Formula (I); Z is selected from halo, —OH, —SH, alkyl, —$NH_2$, —$NHR^{12}$, and —$NR^{12}R^{13}$; $R^1$ is selected from —$NH_2$, —$NHR^{14}$, and —$NR^{14}R^{15}$; and $R^2$ is selected from H and alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.1.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1):

X is N;

Y is N;

R is selected from the group consisting of:

(a) an unsubstituted or substituted monocyclic aryl moiety or an unsubstituted or substituted heteroaryl moiety selected from the group consisting of:

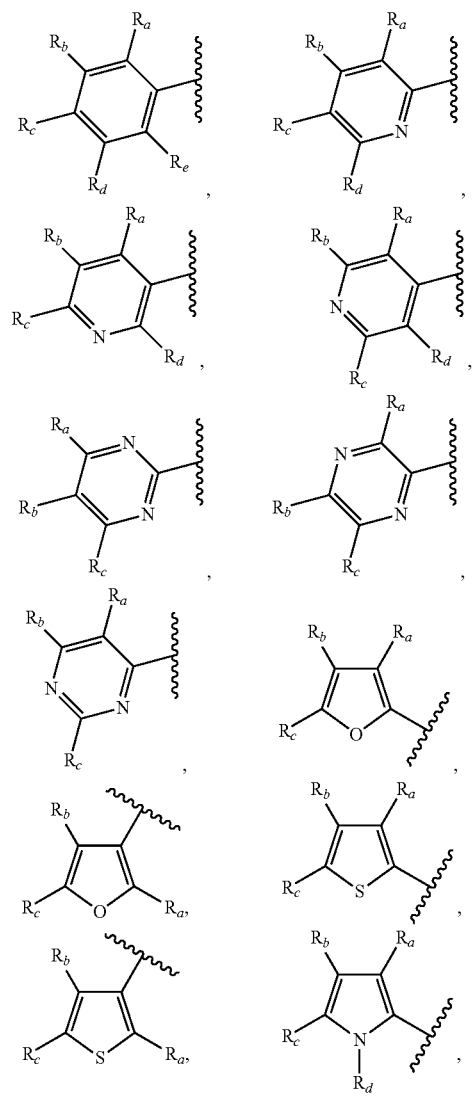

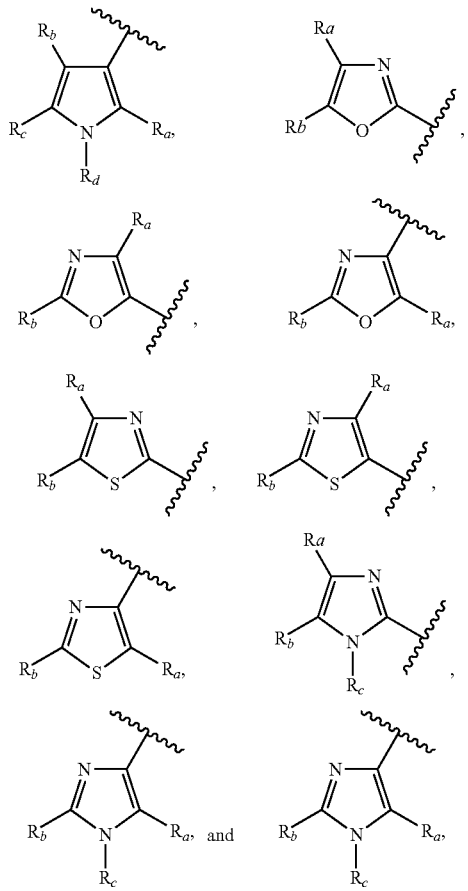

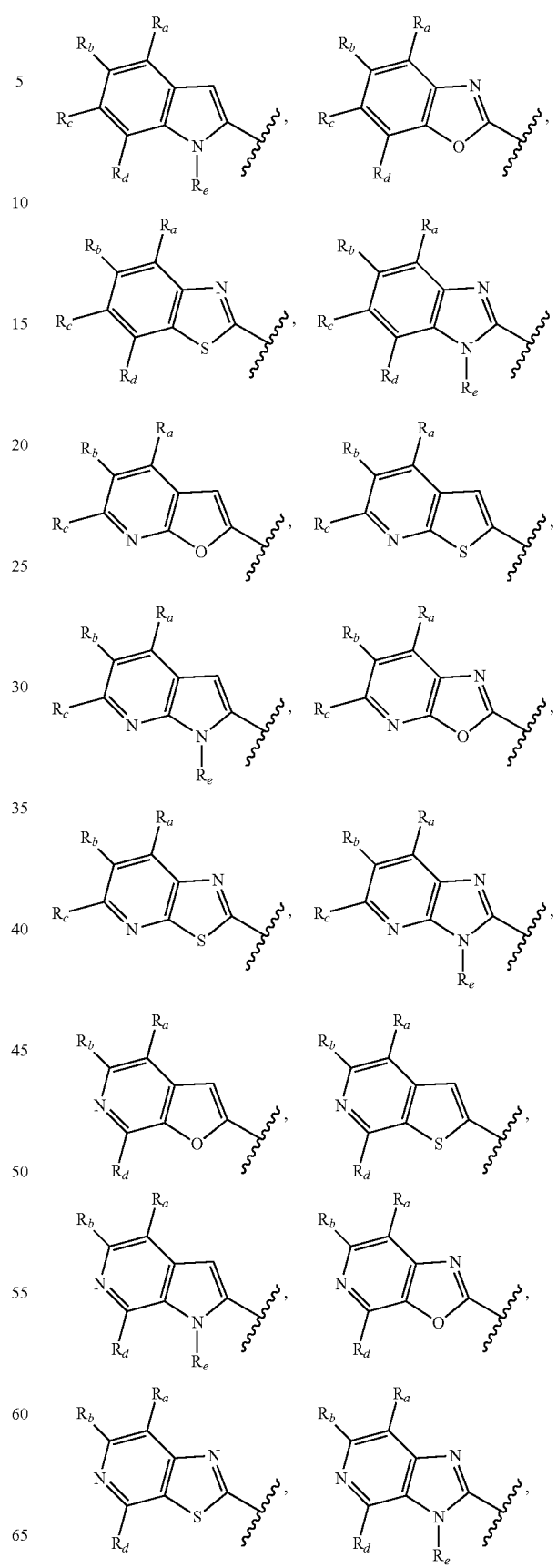

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and (b) an unsubstituted or an substituted bicyclic heteroaryl moiety selected from the group consisting of:

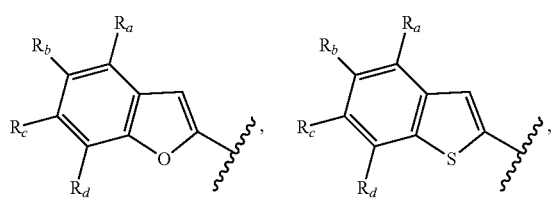

-continued

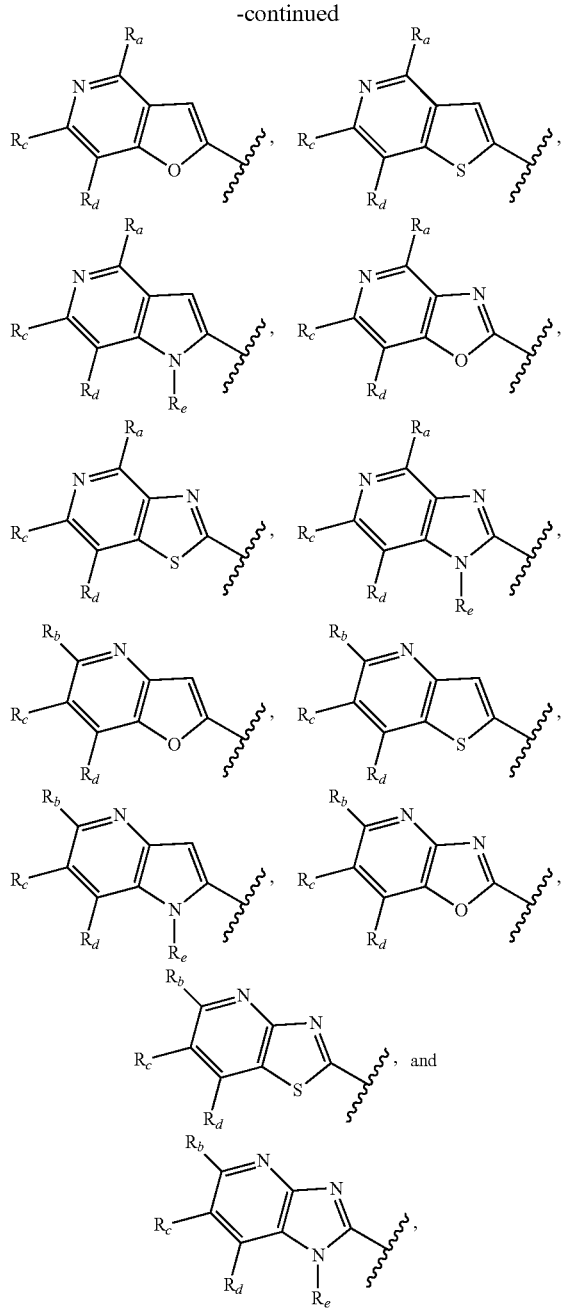

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

R$^1$ is selected from the group consisting of:

(a) —NH$_2$, (b)

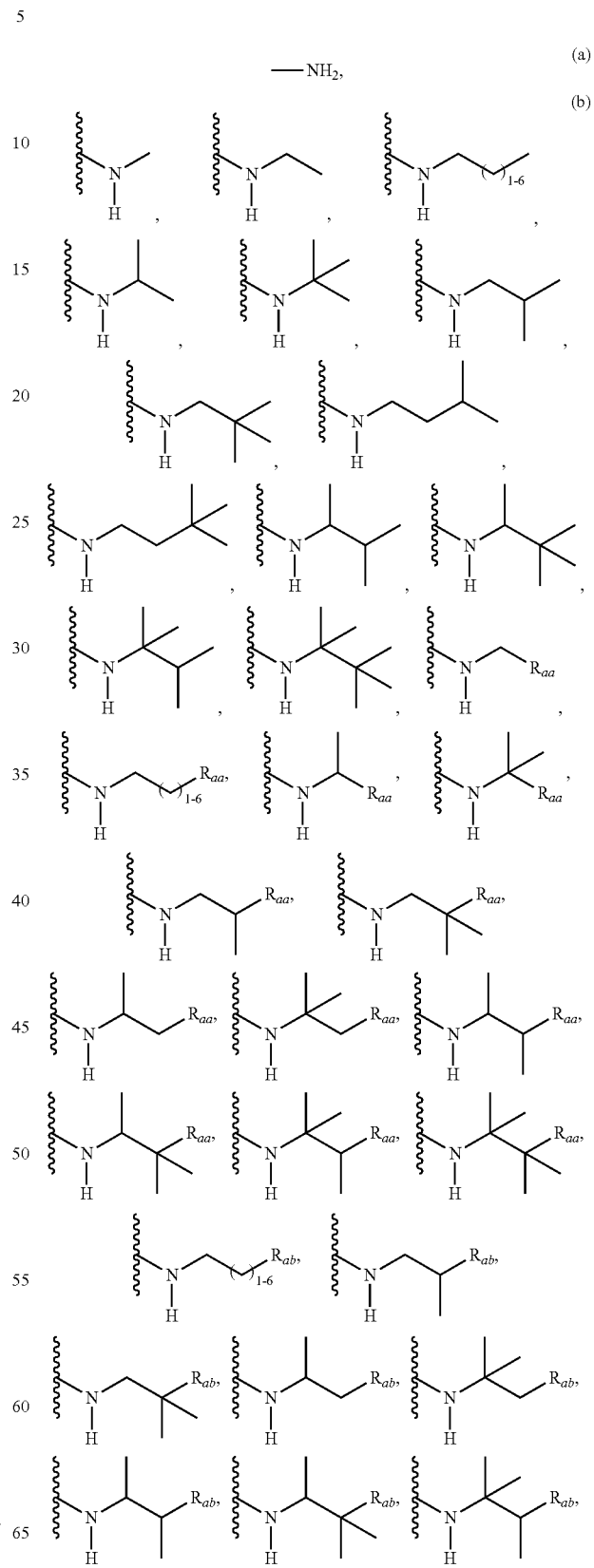

-continued

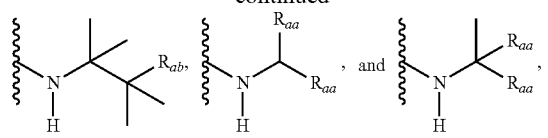

wherein the wavy line represents the point of attachment of $R^1$ to the rest of the molecule, and wherein each $R_{ad}$ is independently selected from haloalkyl (non-limiting examples of which include —CH₇F, —CHF₂, —CF₃, etc.), $R_{ab}$ is selected from OH, OAc, and —O-alkyl (non-limiting examples of which include —O-Me, —O-Et, —O-n-Pr, —O-i-Pr, —O-n-Bu, —O-1-Bu, and —O-t-Bu), —O-haloalkyl (non-limiting examples of which include —O—CH₂F, —O—CHF₂, and —O—CF₃), —NH₂, —NHalkyl, and —N(alkyl)₂, (c)

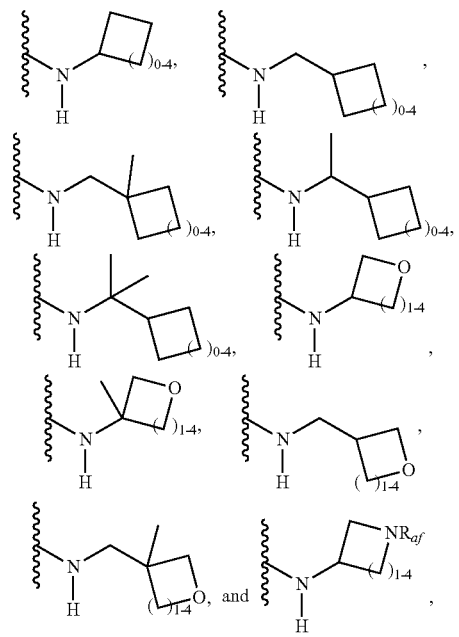

wherein the wavy line represents the point of attachment of $R^1$ to the rest of the molecule, and wherein $R_{af}$ is selected from H and acetyl, (d)

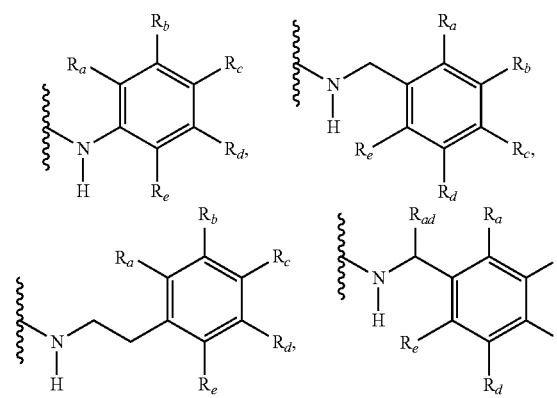

-continued

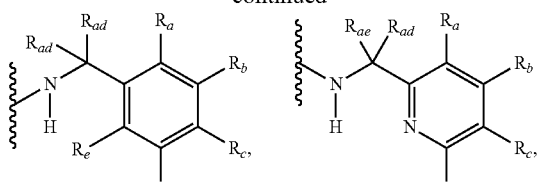

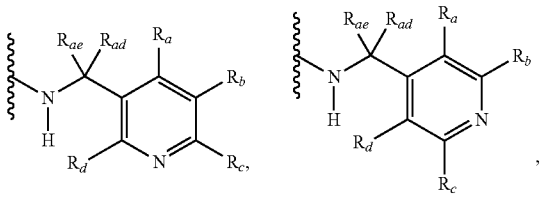

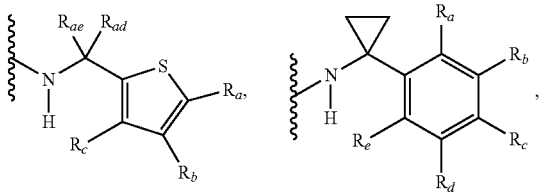

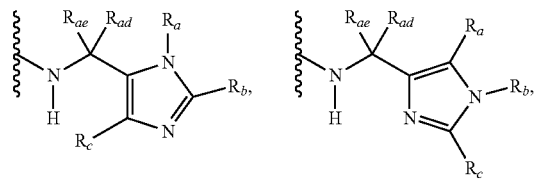

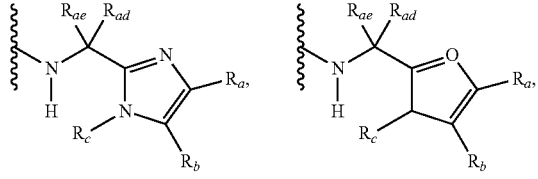

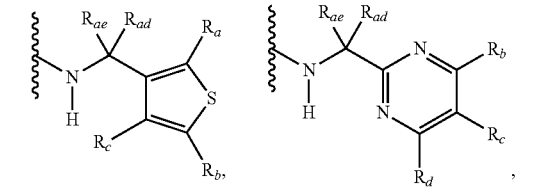

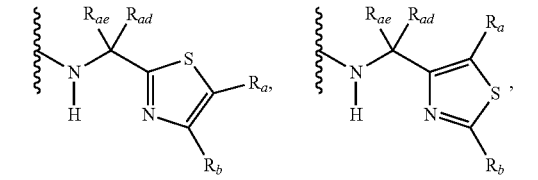

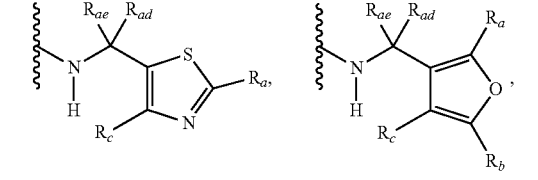

-continued

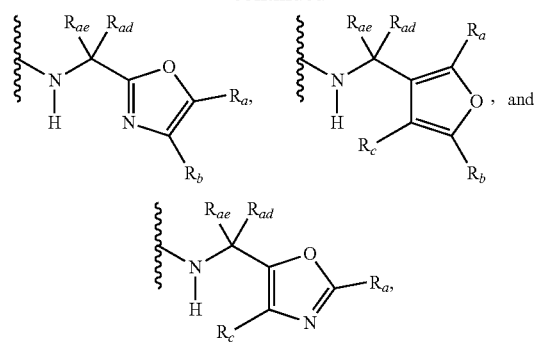

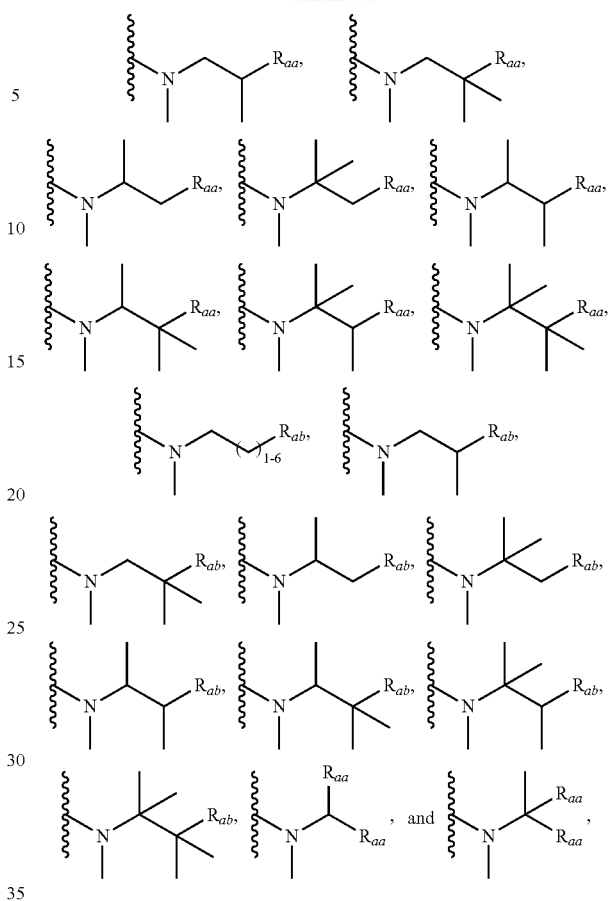

wherein the wavy line represents the point of attachment of $R^1$ to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and wherein each $R_{ad}$ and each $R_{ae}$ is independently selected from alkyl and haloalkyl, (e)

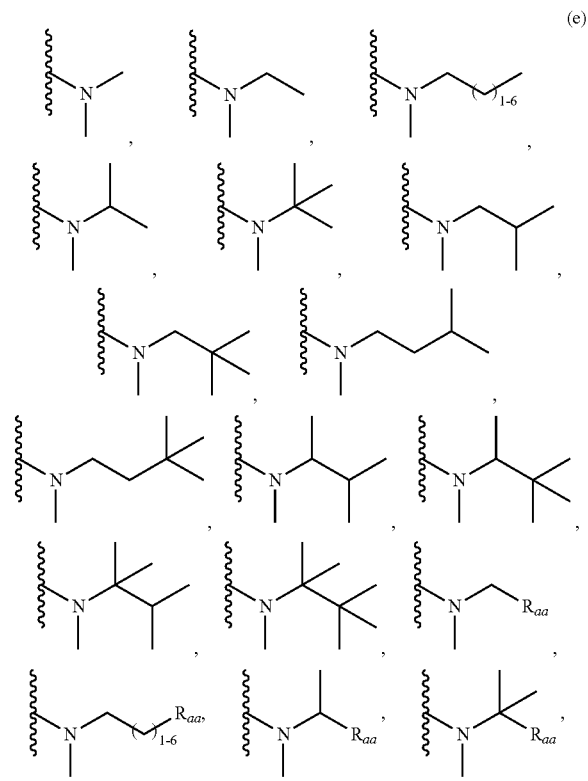

wherein the wavy line represents the point of attachment of $R^1$ to the rest of the molecule, and wherein each $R_{aa}$ is independently selected from haloalkyl (non-limiting examples of which include —CH$_2$F, —CHF$_2$, —CF$_3$, etc.), $R_{ab}$ is selected from OH, OAc, and —O-alkyl (non-limiting examples of which include —O-Me, —O-Et, —O-n-Pr, —O-i-Pr, —O-n-Bu, —O-i-Bu, and —O-t-Bu), —O-haloalkyl (non-limiting examples of which include —O—CH$_2$F, —O—CHF$_2$, and —O—CF$_3$), —NH$_2$, —NHalkyl, and —N(alkyl)$_2$, (f)

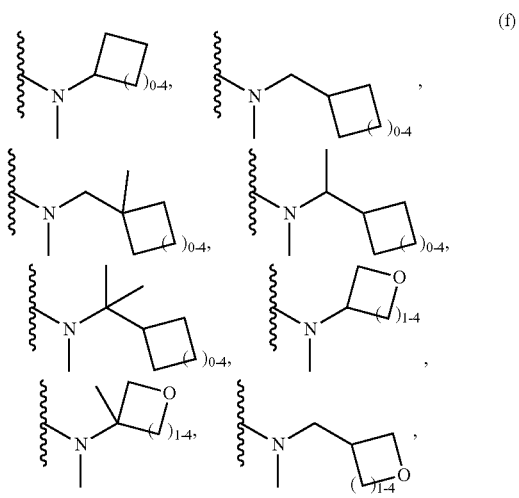

-continued

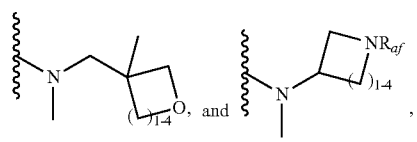

wherein the wavy line represents the point of attachment of R¹ to the rest of the molecule, and wherein $R_{af}$ is selected from H and acetyl, (g)

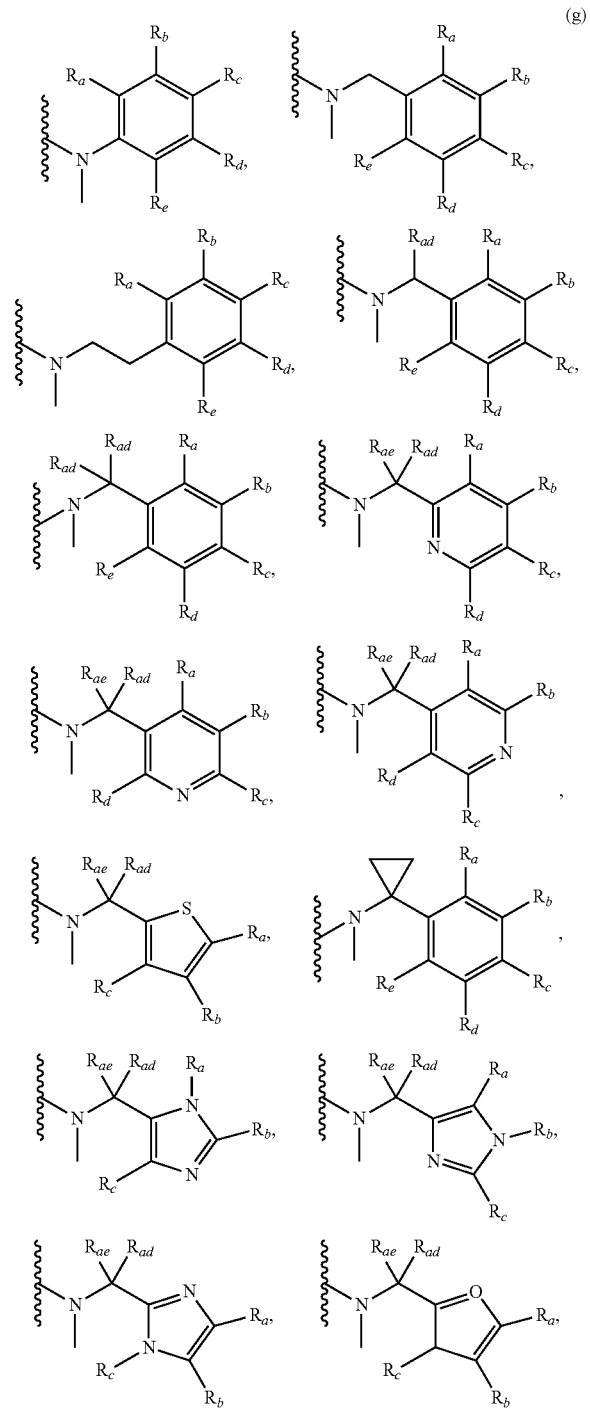

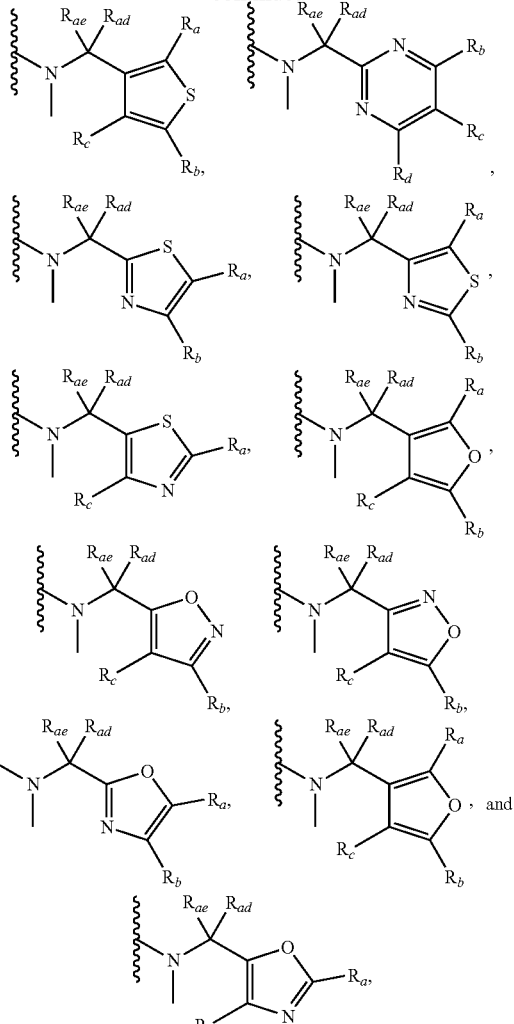

wherein the wavy line represents the point of attachment of R¹ to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH₂, —C(O)NHR¹⁰, —C(O)NR¹⁰R¹¹, —C(O)ONH₂, —C(O)ONHR¹⁰, —C(O)ONR¹⁰R¹¹, —NH₂, —NHR¹⁰, —NR¹⁰R¹¹, —NO₂, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and wherein each $R_{ad}$ and each $R_{ae}$ is independently selected from alkyl and haloalkyl, and (h)

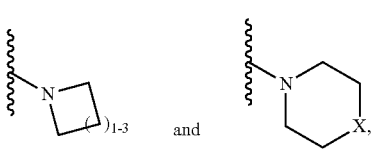

wherein X is selected from O, NH, and NMe; and

Z is selected from the group consisting of H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$, —NHR$^{12}$, and —NR$^{12}$R$^{13}$.

In other embodiments, the compounds of the invention have a structural formula as depicted in Table I below and include tautomers, and pharmaceutically acceptable salts, esters, prodrugs, isomers, and solvates of such compounds and such tautomers.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", arylalkyl-, alkylaryl-, "alkoxy" etc.

"At least one" means one or more than one, for example, 1, 2, or 3, or in another example, 1 or 2, or in another example 1.

"One or more" means one or more than one, for example, 1, 2, or 3, or in another example, 1 or 2, or in another example 1.

"Patient" includes both human and non-human animals. Non-human animals include research animals, farm animals, and companion animals such as mice, primates, monkeys, great apes, cows, sheep, horse, canine (e.g., dogs), and feline (e.g., house cats), etc.

"Composition" includes "pharmaceutical composition" and other compositions not suitable for pharmaceutical use but which may be suitable for other uses such as research or other uses.

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Aminoalkyl" means an alkyl which has been substituted at one or more available carbon atoms by one or more amino group(s). Non-limiting examples of such amino groups include those described herein, such as —NH$_2$, —NHR$^{12}$, —NR$^{12}$R$^{13}$, —NHR$^{14}$, and —NHR$^{15}$.

"Heteroalkyl" means an alkyl moiety as defined above, having one or more carbon atoms, for example one, two or three carbon atoms, including a terminal carbon atom, replaced with one or more heteroatoms, which may be the same or different, where the point of attachment to the remainder of the molecule is through a carbon atom of the heteroalkyl radical. Suitable such heteroatoms include O, S, S(O), S(O)$_2$, —NH—, —N(alkyl)-, and —N(alkyl)$_2$. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like. Additional non-limiting examples include -alkyl-NHalkyl and -alkyl-N(alkyl)$_2$. A non-limiting example of heteroalkyl wherein a terminal carbon atom is replaced with a heteroatom includes -alkyl-NH$_2$.

"Heterohaloalkyl" means an haloalkyl moiety as defined above, having one or more, for example one, two, or three carbon atoms, including a terminal carbon atom, replaced with one or more heteroatoms, which may be the same or different, where the point of attachment to the remainder of the molecule is through a carbon atom of the heterohaloalkyl radical.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

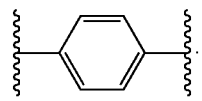 [SMILES: *c1ccc(*)cc1]

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b[thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

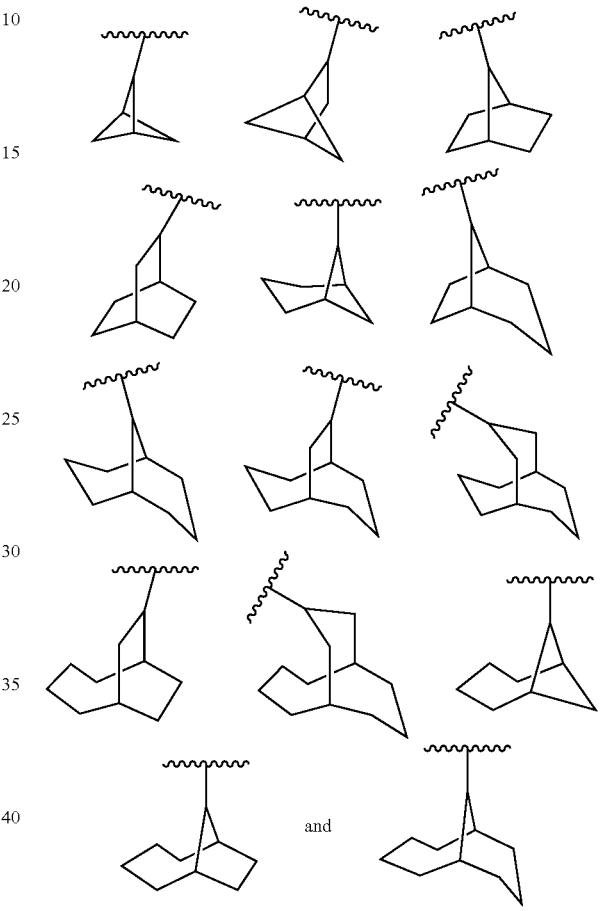

and

"Spirocycloalkyl" means a cycloalkyl moiety in which two available hydrogen atoms attached to the same carbon atom are replacted to form a cycloalkyl group.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an -N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

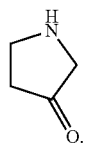

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

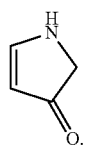

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

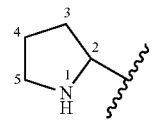

there is no —OH attached directly to carbons marked 2 and 5.

It should also be noted that tautomeric forms of the compounds of the invention are also contemplated as being within the scope of the invention.

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

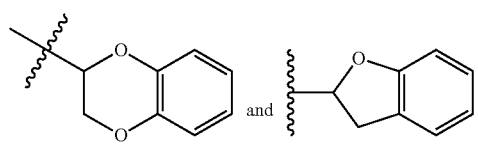 [SMILES: *C1COc2ccccc2O1 ; *C1Cc2ccccc2O1]

The bond to the parent moiety is through a non-aromatic carbon atom.

It is also understood that the terms "arylfused aryl", "arylfused cycloalkyl", "arylfused cycloalkenyl", "arylfused heterocycloalkyl", arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl, "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Heteroaroyl" means an heteroaryl-C(O)— group in which the heteroaryl group is as previously described. The bond to the parent moiety is through the carbonyl. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-O— group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Spirocycloalkyl" means a cycloalkyl group attached to a parent moiety at a single carbon atom. Non-limiting examples of spirocycloalkyl wherein the parent moiety is a cycloalkyl include Spiro[2.5] octane, Spiro[2.4] heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^8$ in —N($R^8$)$_2$, or a variable appears more than once in a structure presented herein such as Foiniula (I), the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of the invention, e.g., of Formula (I)," one to three compounds of the invention, e.g., of Formula (I) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —C(CH$_3$)$_2$— and the like which form moieties such as, for example:

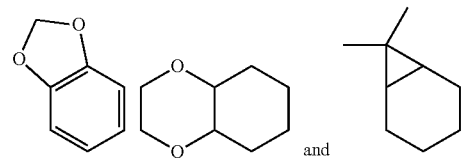

As used herein, the term "composition" is intended to encompass a product comprising the specified ingredients in the specified amounts, as well as any product which results, directly or indirectly, from combination of the specified ingredients in the specified amounts.

The line -----, as a bond generally indicates a mixture of, or either of, the possible isomers, e.g., containing (R)- and (S)-stereochemistry. For example:

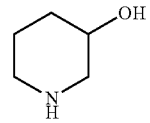

means containing both

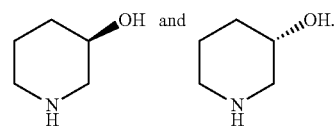

The wavy line ∼∼∼, as used herein, indicates a point of attachment to the rest of the compound. For example, each wavy line in the following structure:

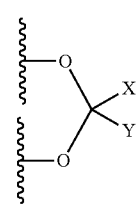

2 indicates a point of attachment to the core structure, as described herein.

Lines drawn into the ring systems, such as, for example:

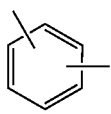

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

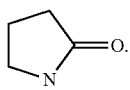

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

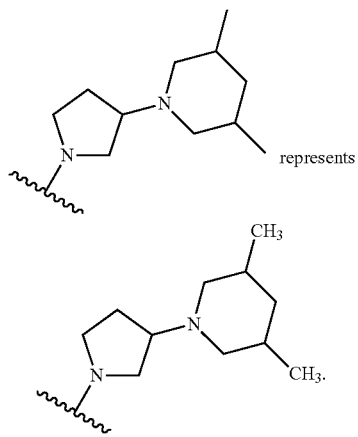

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon (or other atom or heteroatom) with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_2)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-(($C_1-C_6$) alkanoyloxy)ethyl, 1-methyl-14$(C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(0($C_1-C_6$)alkyl)$_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pynolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is WO.

One or more compounds of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to faun crystals which are then isolated by standard methods. Analytical techniques such as, for example IR spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, "P, $^{35}S$, $^{18}F$, and $^{36}Cl$, respectively.

Certain isotopically-labelled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as detel mined by those skilled in the art or patient preference.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration. Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

In one embodiment, the compound is administered orally.

In some embodiments, it may be advantageous for the pharmaceutical preparation compring one or more compounds of the invention be prepared in a unit dosage form. In such forms, the preparation is subdivided into suitably sized unit doses containing appropriate quantities of the active component, e.g., an effective amount to achieve the desired purpose.

PREPARATIVE EXAMPLES

Compounds of the invention can be made using procedures known in the art. The following reaction schemes show typical procedures, but those skilled in the art will recognize that other procedures can also be suitable.

Techniques, solvents and reagents may be referred to by their following abbreviations:
Thin layer chromatography: TLC
High performance liquid chromatography: HPLC
ethyl acetate: AcOEt or EtOAc
methanol: MeOH
ether: $Et_2O$
tetrahydrofuran: THF
Acetonitrile: MeCN
1,2-dimethoxyethane: DME
Trifluoroacetic acid: TFA
Dimethylacetamide: DMA
Dimethylformamide: DMF
Dimethylsulfoxide: DMSO
triethylamine: $Et_3N$ or TEA
tert-Butoxycarbonyl: t-Boc or Boc
2-(Trimethylsilyl)ethoxycarbonyl: Teoc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
centimeters: cm
room temperature (ambient, about 25° C.): rt
Retention time: tR
N-bromosuccinimide: NBS
N-chlorosuccinimide: NCS
Methyl magnesium bromide: MeMgBr
iron(III) acetylacetonate: $Fe(acac)_3$
Diphenylphosphoryl azide: DPPA
1-(3-Dime(hylaminopropyl)-3-ethylcarbodiinnide hydrochloride: EDCI
Diisopropylethylamine: DIEA or i-$Pr_2$NEt or DIPEA
Diisopropylamine: i-$Pr_2$NH
2-(Trimethylsilyl)ethanol: TMSethanol
3-Chloroperoxybenzoic acid: mCPBA
n-Butyllithium: nBuLi
lithium diisopropylamide: LDA
[1,1'-Bis(diphenylphosphino)ferrocene]dichloropalladium (II): $PdCl_2$dppf
Palladium(II) acetate: $Pd(OAc)_2$
Methanesulfonyl chloride: $MeSO_2Cl$
Triphenyl phosphine: TPP or $Ph_3P$
General Method I

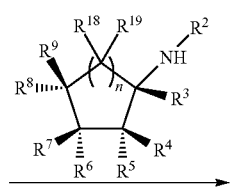

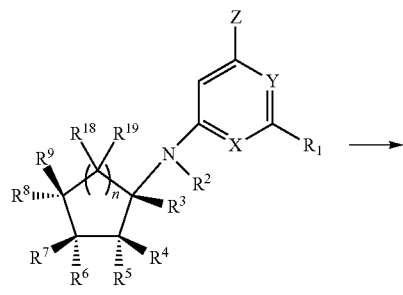

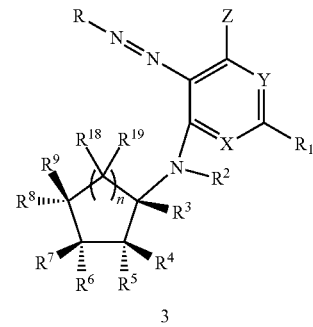

wherein X, Y, Z, R, $R^1$, $R^2$, $R^3$ to $R^9$, $R^{18}$, $R^{19}$, and n are as defined herein.

A mixture of (1S,2R,3S,4S)-2,3-dihydroxy-4-(hydroxymethyl)-1-aminocyclopentane hydrochloride (500 mg, 2.72 mmol) and 2-amino-4,6-dichloropyrimidine (469 mg, 2.86 mmol) in EtOH (20 ml) containing $Et_3N$ (0.80 ml, 5.72 mmol) was refluxed for 72 hrs. After concentrating, the residue was purified by silica gel chromatography, eluting with a gradient of chloroform/methanol (95/5→85/15). Compound 2 (X,Y=N, Z=Cl, $R^1$=$NH_2$, $R^2$,$R^3$,$R^5$, $R^6$, $R^8$=H, $R^4$,$R^7$=OH, $R^8$=$CH_2OH$) was isolated as a white solid (560 mg, 74.9% yield).

MS /viz $(M+H)^+$275.13 (Cl pattern);
$^1$H NMR (DMSO-d6) δ 1.12-0.91 (br s, 1H), 1.93-1.81 (m, 1H), 2.11 (ddd, 1H, J=8.2, 8.5, 13.0 Hz), 3.43-3.30 (m, 2H, coincidental with $H_2O$), 3.58 (dd, 1H, J=5.4, 12.0 Hz), 4.2-

4.1 (br s, 1H), 3.64 (dd, 1H, J=4.7, 9.6 Hz), 4.38 (d, 1H, J=3.6 Hz, D$_2$O exchangeable), 4.57 (dd, 1H, J=5.0, 5.0 Hz, D$_2$O exchangeable), 5.74 (s, 1H), 4.62 (d, 1H, J=5.0 H$_z$, D$_2$O exchangeable), 6.38 (br s, 2H, D$_2$O exchangeable), 7.16 (br s, 1H, D$_2$O exchangeable).

Compound 11: (1S,2R,3S,5S)-3-[[2-amino-6-chloro-5-[(4-chlorophenyl)azo]-4-pyrimidinyl]amino]-5-(hydroxymethyl)-1,2-cyclopentanediol To a stirred solution of 4-chloroaniline (273 mg, 2.14 mmol) in aqueous hydrochloric acid
(0.61 ml conc. HCl in 2.5 ml water) at 0° C. was added dropwise a solution of sodium nitrite (164 mg, 2.38 mmol) in water (2 ml). Stirring was continued for 45 min, and then, this reaction mixture was cannulated dropwise over 30 min. to 2 (535 mg, 1.95 mmol) in a solution containing sodium acetate trihydrate (4.0 g, 29.4 mmol), glacial acetic acid (10 ml) and water (10 ml). After 18 h, the resulting mixture was filtered, and the collected solids were washed with water. After drying for 18 h under vacuum at 78° C., target compound 3 (Compound 11, Ar=4-chlorophenyl, X,Y=N, Z=Cl, R$^1$=NH$_2$, R$^2$, R$^3$, R$^5$, R$^6$, R$^8$=H, R$^4$, R$^7$=OH, R$^8$=CH$_2$OH) was recovered as a yellow solid (480 mg, 59.6% yield).

Mp 238-241° C. (dec)

Analysis calculated for C$_{16}$H$_{18}$Cl$_2$N$_6$O$_3$: C, 46.50; H, 4.39; N, 20.34. Found: C, 46.25; H, 4.26; N, 20.09

Compound 1, (1S,2R,3S,5S)-3-[[2-amino-6-chloro-5-phenylazo]-4-pyrimidinyl]amino]-5-(hydroxymethyl)-1,2-cyclopentanediol was prepared by the same method used for Compound 11, using a stoichiometric amount of aniline instead of 4-chloroaniline.

Compound 9, (1S,2R,3S,5S)-3-[[2-amino-6-chloro-5-[(2-chlorophenyl)azo]-4-pyrimidinyl]amino]-5-(hydroxymethyl)-1,2-cyclopentanediol was prepared by the same method used for Compound 11, using a stoichiometric amount of 2-chloroaniline instead of 4-chloroaniline.

Compound 8, Cyclopentanemethanol, 4-[[2-amino-6-chloro-5-[(4-chlorophenyl)azo]-4-pyrimidinyl]amino]-2-hydroxy-, cis, trans—(+−)—, was prepared by the same method used for Compound 11, using a stoichiometric amount of the required 2'-deoxycarbocyclic nucleoside precursor prepared from 4-amino-2-hydroxycyclopentanemethanol and 2-amino-4,6-dichloropyrimidine instead of the nucleoside precursor used for 21174 prepared from (1S,2R,3S,4S)-2,3-dihydroxy-4-(hydroxymethyl)-1-aminocyclopentane and 2-amino-4,6-dichloropyrimidine.

In other embodiments, the compounds of the invention have a structural formula as depicted in Table I below and include tautomers, and pharmaceutically acceptable salts, esters, prodrugs, isomers, and solvates of such compounds and such tautomers.

TABLE I

| Compd # | Structure | EC90 (uM) | 1H NMR data | MS |
|---|---|---|---|---|
| 1 | 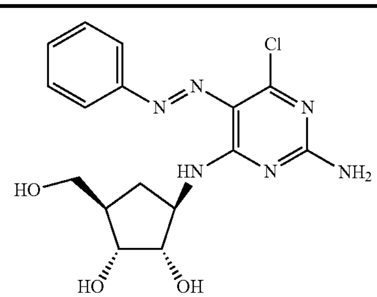 | C | (DMSO-d6) δ 1.16 (dt, 1H, J = 7.7 Hz), 2.08-1.98 (m, 1H), 2.42-2.31 (m, 1H), 3.41 (br s, 1 H), 3.43 (br s, 1H), 3.77-3.72 (m, 2H), 4.35 (m, 1H), 4.95-4.3 (m, 3H, 3H D$_2$O exch., 7.41 (m, 1H), 7.52 (m, 2H), 7.76 (m, 2H), 10.46 (d, 1H, J = 7.5 Hz) | 379.2 (Cl pattern) |
| 2 | 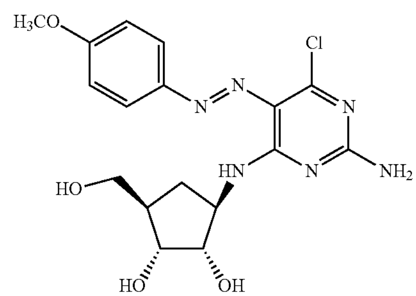 [SMILES: COc1ccc(/N=N/c2c(Cl)nc(N)nc2N[C@@H]2C[C@H](CO)[C@@H](O)[C@H]2O)cc1] | A | NMR Data Not Available; | 409.2 (Cl pattern) |
| 3 | 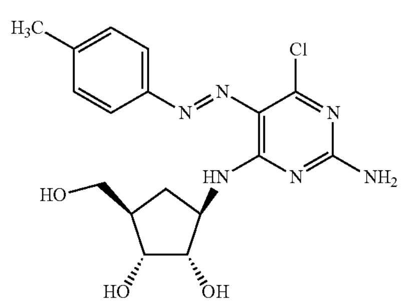 [SMILES: Cc1ccc(/N=N/c2c(Cl)nc(N)nc2N[C@@H]2C[C@H](CO)[C@@H](O)[C@H]2O)cc1] | A | (DMSO-d6) δ 1.15 (dt, 1H, J = 7.9, 13.5 Hz), 1.89-2.02 (m, 1H), 2.26-2.40 (m, 1H), 2.37 (s., 1H), 2.38-2.48 (m, 2H), 2.72-2.79 (m, 2H), 4.30-4.44 (m, 1H), 4.45-4.55 (br s, 1H, D$_2$O exch.), 4.63-4.73 (br s, 1H, D$_2$O exch.), 4.74-4.85 (br s, 1H, D$_2$O exch.), 7.73-7.36 (m, 2H, Ar), 7.40-7.53 (br s, 2H, NH$_2$, D$_2$O exch.), 7.65-7.70 (m, 2H, Ar), 10.43 (d, 1H, J = 7.3 Hz, NH). | 393.2 (Cl pattern) |

TABLE I-continued

| Compd # | Structure | EC90 (uM) | 1H NMR data | MS |
|---|---|---|---|---|
| 4 | 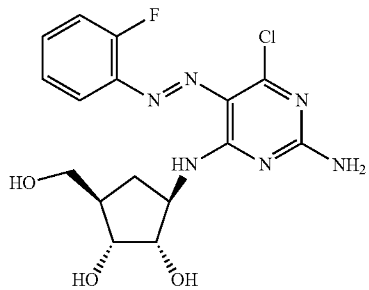 [SMILES: Nc1nc(Cl)c(/N=N/c2ccccc2F)c(N[C@@H]2C[C@H](CO)[C@@H](O)[C@H]2O)n1] | A | (DMSO-d₆): δ 1.01-1.13 (m, 1H), 1.89-2.02 (m 1H), 2.31 (dt, 1H, J = 8.6, 13.4 Hz), 1.33-1.46 (m, 2H), 3.62-3.77 (m, 2H), 4.41 (quint, 1H, J = 7.7 Hz), 4.53 (d, 1H, J = 4.1 Hz, D₂O exch.), 4.59 (app t, 1H, J = 5.0 Hz, D₂O exch.), 4.77 (d, 1H, J = 5.5 Hz, D₂O exch.), 7.28-7.38 (m, 2H), 7.39-7.50 (m, 2H), 7.58-7.78 (m, 2H), 10.6 (d, 1H, J = 7.5 Hz). | 397.2 |
| 5 | 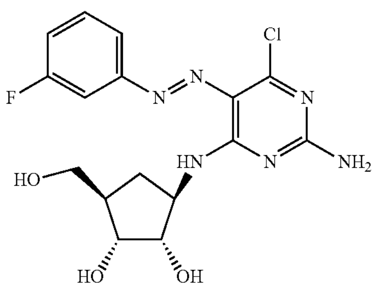 [SMILES: Nc1nc(Cl)c(/N=N/c2cccc(F)c2)c(N[C@@H]2C[C@H](CO)[C@@H](O)[C@H]2O)n1] | A | (DMSO-d₆): δ 1.17 (dt, 1H, J = 7.7, 13.4 Hz), 1.89-2.01 (m 1H), 2.25-2.37 (m, 1H), 3.38-3.48 (m, 2H), 3.72-3.82 (br s, 2H), 4.39 (app quint, 1H, J = 7.4 Hz), 4.52 (br s, 1H, D₂O exch.), 4.67-4.74 (m, 1H, D₂O exch.), 4.78-4.86 (br s, 1H, D₂O exch.), 7.20-7.28 (m, 1H), 7.48-7.70 (m, 5H), 10.6 (d, 1H, J = 7.5 Hz). | 397.2 |
| 6 | 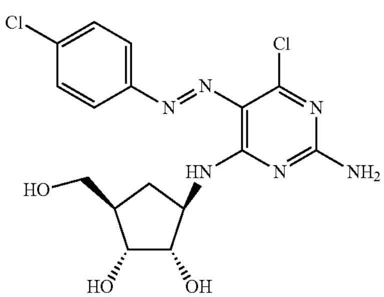 [SMILES: Nc1nc(Cl)c(/N=N/c2ccc(Cl)cc2)c(N[C@@H]2C[C@H](CO)[C@@H](O)[C@H]2O)n1] | B | (DMSO-d₆): δ 1.10-1.23 (m, 1H), 1.89-2.01 (m, 1H), 2.25-2.41 (m, 1H), 3.42 (d, 2H, J = 5.2 Hz), 3.71-3.80 (m, 2H), 3.75-4.20 (m, 2H, OHs & H₂O, D₂O exch.), 4.32-4.45 (m, 1H), 4.59 (d, 1H, J = 5.3 Hz), 7.39-7.90 (br s, 2H, NH, D₂O exch.), 7.49-65 (app d, 2H, J = 8.7 Hz, Ar), 7.70-7-80 (app d, 2H, J = 8.7 Hz, Ar), 10.38 (d, 1H, J = 7.4 Hz). | 413.1 (2 Cl pattern) |
| 7 | 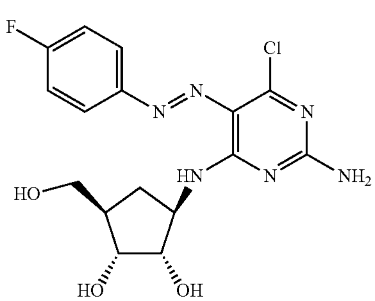 [SMILES: Nc1nc(Cl)c(/N=N/c2ccc(F)cc2)c(N[C@@H]2C[C@H](CO)[C@@H](O)[C@H]2O)n1] | B | (DMSO-d6) δ 1.11-1.22 (m, 1H), 1.89-2.01 (m, 1H), 2.26-2.38 (m, 2H), 3.38-3.50 (m, 2H), 4.31-4.43 (m, 1H), 4.48-4.55 (br s, 1H, D₂O exch.), 4.66-4.74 (br s, 1H, D₂O exch.), 4.76- 4.86 (br s, 1H, D₂O exch.), 7.36 (t, 2H, J = 8.8 Hz, Ar), 7.46-7.62 (m, 2H, NH, D₂O exch.), 7.77-7.85 (m, 2H, Ar), 10.33 (d, 1H, J = 7.5 Hz). | 397.2 |

TABLE I-continued

| Compd # | Structure | EC90 (uM) | 1H NMR data | MS |
|---|---|---|---|---|
| 8 | 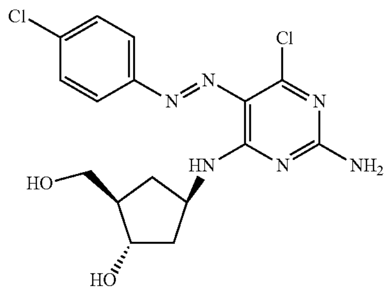 [SMILES: Nc1nc(Cl)c(/N=N/c2ccc(Cl)cc2)c(N[C@@H]2C[C@H](CO)[C@@H](O)C2)n1] | B | (DMSO-d6) δ 1.29 (dt, 1H, J = 7.8, 13.0 Hz), 1.71-1.83 (m, 1H), 1.83-2.00 (m, 2H), 2.31 (dt, 1H, J = 7.9, 12.8 Hz), 3.38-3.52 (m, 2H), 3.94-4.02 (br s, 1H), 4.58-4.73 (m, 2H), 7.52-7.62 (m, 2H, Ar), 7.58-7.69 (br s, 2H, NH₂, D₂O exch.), 7.71-7.79 (m, 2H, Ar), 10.34 (d, 1H, J = 7.5 Hz). | 397.0 (2 Cl pattern) |
| 9 | 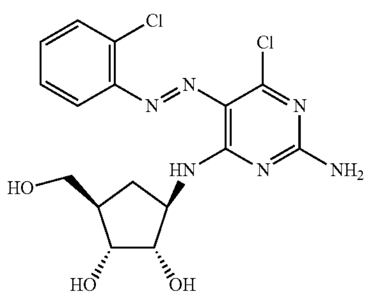 [SMILES: Nc1nc(Cl)c(/N=N/c2ccccc2Cl)c(N[C@@H]2C[C@H](CO)[C@@H](O)[C@H]2O)n1] | B | (DMSO-d6) δ 1.11 (dt, 1H, J = 9.1, 13.2 Hz), 2.0-1.89 (m, 1H), 2.27 (dt, 1H, J = 8.6, 13.1 Hz), 3.31-3.41 (m, 1H), 3.69-3.77 (m, 2H), 4.48-4.62 (m, 1H), 4.30-5.00 (br m, 3H, D₂O exch.), 7.39-7.51 (m, 2H), 7.66 (dd, 1H, J = 1.4, 7.6 Hz), 7.63-7.75 (m, 2H, D₂O exch.), 7.75 (dd, 1H, J = 1.9 Hz, 12.1 Hz), 10.65 (d, 1H, J = 7.9 Hz). | 413.1 (2 Cl pattern) |
| 10 | 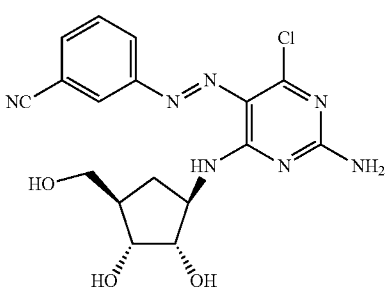 [SMILES: N#Cc1cccc(/N=N/c2c(Cl)nc(N)nc2N[C@@H]2C[C@H](CO)[C@@H](O)[C@H]2O)c1] | B | (DMSO-d₆):δ 1.17 (dt, 1H, J = 7.9, 13.6 Hz), 1.89-2.01 (m 1H), 2.25-2.38 (m, 1H), 3.39-3.49 (m, 2H), 3.74-3.85 (m, 2H), 4.40 (app quint, 1H, J = 7.2 Hz), 4.47-4.56 (br s, 1H, D₂O exch.), 4.68-4.77 (br s, 1H, D₂O exch.), 4.77-4.90 (br s, 1H, D₂O exch.), 7.66-7.81 (m, 2H, D₂O exch.), 7.58-7.99 (m, 2H), 8.15-8.18 (m, 1H), 10.36 (d, 1H, J = 7.4 Hz). | 404.2 (Cl pattern) |
| 11 | 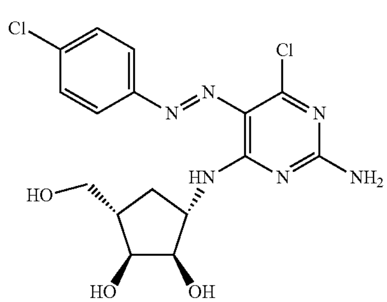 [SMILES: Nc1nc(Cl)c(/N=N/c2ccc(Cl)cc2)c(N[C@H]2C[C@@H](CO)[C@H](O)[C@@H]2O)n1] | B | (DMSO-d6) δ 1.12-1.23 (m, 1H), 1.90-2.01 (m, 1H), 2.26-2.36 (m, 1H), 3.42 (dd, 2H, J = 5.1, 5.1 Hz), 3.72-3.81 (m, 2H), 4.35-4.45 (m, 1H), 4.50 (d, 1H, J = 3.4 Hz, D₂O exch.), 4.69 (dd, 1H, J = 5.1 Hz, D₂O exch.), 4.80 (d, 1H, J = 4.7 Hz, D₂O exch.), 7.55-7.62 (m, 4H), 7.74-7.79 (m, 2H), 10.4 (d, 1H, J = 7.5 Hz). | 413.1 (2 Cl pattern) |

TABLE I-continued

| Compd # | Structure | EC90 (uM) | 1H NMR data | MS |
|---|---|---|---|---|
| 12 | (structure: 3-nitrophenyl-azo-chloropyrimidine with aminocyclopentane triol substituent) | B | DMSO-$d_6$: δ 1.20 (dt, 1H, J = 7.7, 13.5 Hz), 1.90-2.01 (m 1H), 2.26-2.38 (m, 1H), 3.44 (app t, 2H, J = 5.2 Hz), 3.74-3.86 (m, 2H), 4.41 (app quint, 1H, J = 7.3 Hz), 4.51 (d, 1H, J = 4.2 Hz, $D_2O$ exch.), 4.71 (app t, 1H, J = 5.1 Hz, $D_2O$ exch.), 4.82 (d, 1H, J = 5.4 Hz, $D_2O$ exch.), 7.69-7.77 (br s, 2H, $D_2O$ exch.), 7.81 (t, 1H, J = 8.1 Hz), 8.17-8.27 (m, 2H), 8.17-8.27 (m, 2H), 8.48 (t, 1H, J = 2.0 Hz), 10.38(d, 1H, J = 7.5 Hz). | 424.2 (Cl pattern) |

Assays

Cell-based HCV Replicon Assay

To measure cell-based anti-HCV activity of the compounds of the present invention, replicon cells were seeded at 5000 cells/well in 96-well collagen I-coated Nunc plates in the presence of the compound of the invention. Various concentrations of a compound of the invention, typically in 10 serial 2-fold dilutions, were added to the assay mixture, the starting concentration of the compound ranging from 25 µM to 1 µM. The final concentration of DMSO was 0.5%, fetal bovine serum was 10%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA; 5B.2R, TTGATGGGCAGCTTGGTTTC; the probe sequence was FAM-labeled CACGCCATGCGCTGCGG. GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ΔCT values ($CT_{5B}$-$CT_{GAPDH}$) were plotted against the concentration of test compound and fitted to the sigmoid dose-response model using GraphPad PRISM software. $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for compounds of the invention that were tested was obtained using the above method. Calculated $EC_{90}$ values are reported for each compound in Table I as falling within the following ranges:

"A"—less than or equal to about 5 µM
"B"—greater than about 5 µM
"**" indicates that the value was not available for the compound Methods of Use The compounds of the invention are useful in human and veterinary medicine for treating or preventing a viral infection or a virus-related disorder in a patient. In accordance with the invention, the compounds of the invention can be administered to a patient in need of treatment or prevention of a viral infection or a virus-related disorder.

Accordingly, in one embodiment, the invention provides methods for treating a viral infection in a patient comprising administering to the patient an effective amount of at least one compounds of the invention or a pharmaceutically acceptable salt, ester, prodrug, isomer, tautomer, or solvate thereof. In another embodiment, the invention provides methods for treating a virus-related disorder in a patient comprising administering to the patient an effective amount of at least one compounds of the invention or a phainiaceutically acceptable salt, ester, prodrug, isomer, tautomer, or solvate thereof.

Treatment or Prevention of a Viral Infection

The compounds of the invention can be used to treat or prevent a viral infection. In one embodiment, the compounds of the invention can be used to inhibit viral replication. In a specific embodiment, the compounds of the invention can be inhibitors of HCV replication. Accordingly, the compounds of the invention are useful for treating viral diseases and disorders related to the activity of a virus, such as HCV polymerase.

Such uses as are described herein may be performed in a patient in need thereof, although in vitro and ex vivo uses, such as in diagnostic and research contexts, are also contemplated. References made herein to the use of compounds of the invention also refers to uses of compositions comprising compounds of the invention.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol,* 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol,* 78(Ptl):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol,* 75(Pt 5):1053-1061 (1994)).

Treatment or Prevention of a Virus-Related Disorder

The compounds of the invention can be used to treat or prevent a virus-related disorder. Accordingly, the compounds of the invention are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The compounds of the invention are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one compounds of the invention or a pharmaceutically acceptable salt, solvate, ester or prodrug thereof.

Treatment or Prevention of a Disorder Related to HCV Infection

The compounds of the invention can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one compound of the invention, or a pharmaceutically acceptable salt, solvate, ester or prodrug thereof.

Combination Therapy

In another embodiment, the present methods for treating or preventing a viral infection can further comprise the administration of one or more additional therapeutic agents. In one embodiment, such one or more additional therapeutic agent may be one or more additional compounds of the invention. In another embodiment, such one or more additional therapeutic agent is an agent other than a compound of the invention.

In one embodiment, the additional therapeutic agent is an antiviral agent. Non-limiting examples of antiviral agents are as described herein and include, e.g., interferon.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one compound of the invention, or a pharmaceutically acceptable salt, solvate, ester or prodrug thereof, and (ii) at least one antiviral agent other than a compound of the invention, wherein the amounts administered are together effective to treat or prevent a viral infection.

When administering such a combination to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of the invention and an additional therapeutic agent may be present in fixed amounts (dosage amounts) in a single dosage unit (e.g., a capsule, a tablet and the like). (A commercial example of such single dosage unit containing fixed amounts of two different active compounds is VYTORIN® (available from Merck Schering-Plough Pharmaceuticals, Kenilworth, New Jersey)).

In one embodiment, the at least one compound of the invention is administered at time when the additional antiviral agent(s) exert their prophylactic or therapeutic effect, or vice versa.

In another embodiment, the at least one compound of the invention and the additional antiviral agent(s) are administered in doses commonly employed when such agents are used as monotherapy for treating a viral infection.

In another embodiment, the at least one compound of the invention and the additional antiviral agent(s) are administered in doses lower than the doses commonly employed when such agents are used as monotherapy for treating a viral infection.

In another embodiment, the at least one compound of the invention and the additional antiviral agent(s) act synergistically and are administered in doses lower than the doses commonly employed when such agents are used as monotherapy for treating a viral infection.

In one embodiment, the at least one compound of the invention and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one compound of the invention and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one compound of the invention and the additional antiviral agent(s) may inhibit the resistance of a viral infection to these agents. Non-limiting examples of other therapeutic agents useful in the present compositions and methods include an an viral (e.g., HCV) polymerase inhibitor, a viral (e.g., HCV) protease inhibitor, an interferon, a viral replication inhibitor, an antisense agent, a therapeutic vaccine, a viral protease inhibitor, a virion production inhibitor, an immunosuppressive agent, an antiviral antibody, a CYP-450 inhibitor, an antiviral booster, and an antiviral sensitizer, and any agent useful for treating an RNA-dependent polymerase-related disorder.

In one embodiment, the at least one additional antiviral agent is a viral polymerase inhibitor.

In another embodiment, the at least one additional antiviral agent is an HCV polymerase inhibitor.

In one embodiment, the at least one additional antiviral agent is a viral protease inhibitor.

In another embodiment, the at least one additional antiviral agent is an HCV protease inhibitor.

In another embodiment, the at least one additional antiviral agent is an interferon.

In still another embodiment, the at least one additional antiviral agent is a viral replication inhibitor.

In another embodiment, the at least one additional antiviral agent is an antisense agent.

In another embodiment, the at least one additional antiviral agent is a therapeutic vaccine.

In a further embodiment, the at least one additional antiviral agent is an virion production inhibitor.

In another embodiment, the at least one additional antiviral agent is an antibody.

In another embodiment, the at least one additional antiviral agents comprise a protease inhibitor and a polymerase inhibitor.

In still another embodiment, the at least one additional antiviral agents comprise a protease inhibitor and an immunosuppressive agent.

In yet another embodiment, the at least one additional antiviral agents comprise a polymerase inhibitor and an immunosuppressive agent.

In a further embodiment, the at least one additional antiviral agents comprise a protease inhibitor, a polymerase inhibitor and an immunosuppressive agent.

In another embodiment the at least one additional agent is ribavirin, Levovirin, or Viramidine.

In other embodiments, pharmaceutical compositions according to the invention comprise at least one compound of the invention and a CYP-450 inhibitor. Non-limiting examples of suitable CYP-450 inhibitors include ritonavir.

In other embodiments, pharmaceutical compositions according to the invention comprise at least one compound of the invention and an interferon. Non-limiting examples of such interferon are as described herein and include alpha interferon, pegylated interferon and conjugates thereof. Additional non-limiting examples of interferon include PEG-intron™ brand pegylated interferon, Pegasys™ brand pegylated interferon, Infergen™ brand interferon, and Alferon™ brand pegylated interferon.

In other embodiments, pharmaceutical compositions according to the invention comprise at least one compound of the invention and an interferon. Further comprising ribavirin, Levovirin, or Viramidine.

In other embodiments, pharmaceutical compositions according to the invention comprise at least one compound of the invention and a protease inhibitor.

In other embodiments, pharmaceutical compositions according to the invention comprise at least one compound of the invention, a protease inhibitor, and an interferon.

In other embodiments, pharmaceutical compositions according to the invention comprise at least one compound of the invention, a protease inhibitor, an interferon, and ribavirin.

In other embodiments, pharmaceutical compositions according to the invention comprise at least one compound of the invention, a polymerase inhibitor, and an interferon.

In other embodiments, pharmaceutical compositions according to the invention comprise at least one compound of the invention, a polymerase inhibitor, an interferon, and ribavirin.

In other embodiments, pharmaceutical compositions according to the invention comprise at least one compound of the invention, a protease inhibitor, polymerase inhibitor, and an interferon.

In other embodiments, pharmaceutical compositions according to the invention comprise at least one compound of the invention, a protease inhibitor, a polymerase inhibitor, an interferon, and ribavirin.

HCV polymerase inhibitors useful in the present methods and compositions include, but are not limited to VP-19744 (WyethlViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Additional non-limiting examples of HCV polymerase inhibitors useful in the present methods and compositions include: MK00608, NM283, HCV796, R1626, A848837, GSK71185, R7128, VCH$_{759}$, GS9190, VP19744, and XTL2125.

Additional non-limiting examples of HCV polymerase inhibitors and HCV protease inhibitors useful in the present methods and compositions include: ANA598 (Anadys Pharmaceuticals), ABT-333, (Abbott), VCH-916, (Virochem), MK7009, (Merck), PF-00868554, (Pfizer) VX-500, (Vertex) GS9190, (Gilead) GSK625433, (GlazoSmithKline) ITMN-191 (R-7227), (Intermune), R7128, (Pharmasset/Roche), VCH-759 (Virochem), R1626, (Roche), TMC435350, (Medivir/Tibotec), SCH 503034 (Boceprevir, Schering), SCH900518 (Schering), and VX 950 (telaprevir) (Vertex). Additional non-limiting examples of HCV polymerase inhibitors include MK-3281 (Merck), PSI-7851 (Pharmasset), IDX184 (Indenix), ANA598 (Anadys), ABT-333 (Abbott), VCH-916 (Vertex), PF-0086554 (Pfizer), R7128 (Pharmasset/Roche), GS 9190 (Gilead), and VCH-759 (Vertex).

Additional non-limiting examples of agents useful in the present methods and compositions include: SPC3649 (LNA-antimiRTM-122), microRNA, Santaris Pharma, CF102, (A3AR AGONISTS) (CAN-FITE), IMO-2125, TLR9 agonist, (Idera Pharmaceuticals), PYN 17, Botanical, (Phynova), Bavituximab (formerly Tarvacin), Anti-Phospholipid Therapy, (Peregrine), A-831 and/or A-832 (each of which are listed as NS5A Inhibitors from ArrowTherapeutics Ltd.), BMS-790052 (NS5A inhibitors from BMS), NOV-205, Immunomodulator, (Novelos Therapeutics), CTS-1027, Anti-inflammatory, (Conatus), Oglufanide disodium, Immunomodulator, (Implicit Bioscience), Alinia (nitazoxanide), Thiazolides, (Romark Laboratories), SCV-07, Broad spectrum immune stimulator, (SciClone), MitoQ (mitoquinone), Inflammation/Fibrosis Inhibitor, (Antipodean Pharmaceuticals), DEBIO-025, Cyclophilin inhibitor, (Debio Pharm Group), SCY-635, cyclophilin inhibitor (SCYNEXIS), PF-03491390 (Formerly IDN-6556), Pancaspase Inhibitor, (Pfizer Pharmaceuticals), Civacir, HCV Immune Globulin, NABI, MX-3253 (celgosivir), Glucosidase I Inhibitor, (MIGENIX), VGX-410C (Mifepristone), IRES Inhibitor, (VGX Pharmaceuticals), Viramidine (Taribavirin), Nucleoside Analogue, (Valeant Pharmaceuticals), and ZADAXIN® (thymalfasin or thymosin alpha 1), Immunomodulator, (SciClone/Sigma-Tau).

Additional non-limiting examples of agents useful in the present methods and compositions include: TLR agonists (e.g., ANA773, Anadys Pharmaceuticals), immunomodulators (e.g., CYT107, Cytheris; oglufanide disodium, Implicit Bioscience), microRNA (e.g., SPC3649 (LNA-antimiR™-122, Santaris Pharma), A3AR agonists (e.g., CF102, CAN-FITE), TLR9 agonists (e.g., Idera Pharmaceuticals), anti-phospholipid therapeutics (e.g., bavituximab (formerly Tarvacin), Peregrine), immunomodulators (e.g., NOV-205, Novelos Therapeutics), caspase inhibitors (e.g., GS-9450, Gilead), anti-inflammatories (e.g., CTS-1027, Conatus), thiazolides (e.g., alinia (nitazoxanide), Romark Laboratories), broad spectrum immune stimulators (e.g., SCV-07, Sci-Clone), inflammation/fibrosis inhibitors (e.g., MitoQ (mitoquinone), Antipodean Pharmaceuticals, cyclophilin inhibitors (e.g., DEBIO-025, Debio Pharm Group), pancaspase inhibitors (e.g., PF-03491390 (formerly IDN-6556, Pfizer Pharmaceuticals), and nucleoside analogues (e.g., Viramidine (Taribavirin), Valeant Pharmaceuticals).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron P), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, California).

Additional examples of Interferons useful in the present methods and compositions include, but are not limited to: IL-29 (PEG-Interferon Lambda), Long acting Interferon, ZymoGenetics, Oral Interferon alpha, Oral Interferon, (Amarillo Biosciences), Belerofon (oral), Oral interferon , (Nautilus Biotech), BLX-883 (Locteron), Long Acting Interferon, (Biolex Therapeutics/OctoPlus), Omega Interferon, Interferon, (Intarcia Therapeutics), Albuferon, Long Acting Interferon (injections every two weeks), (Human Genome Sciences), Consensus interferon (Infergen), and Interferon, (Three Rivers Pharma).

Antiviral antibodies (antibody therapy agents) useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but are not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), and HIV protease inhibitors (e.g., amprenavir, atazanavir, fosemprenavir, indinavir, lopinavir, ritonavir, nelfinavir, saquinavir, tipranavir and TMC 114).

Viral replication inhibitors useful in the present methods and compositions include, but are not limited to, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of NS-3 serine protease inhibitors include, but are not limited to, SCH 503034 (Boceprevir, Schering), SCH900518 (Schering), Telaprevir (VX950), ITMN-191, TMC435350, GS9132, MK7009, and BILN2061. Examples of HCV protease inhibitors useful in the present methods include, but are not limited to, those disclosed in Landro et al., *Biochemistry*, 36(31):9340-9348 (1997); Ingallinella et al., *Biochemistry*, 37(25):8906-8914 (1998); Llinas-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); and International Publication Nos. WO 98/14181; WO 98/17679, WO 98/17679, WO 98/22496 and WO 99/07734. Additional non-limiting examples of protease inhibitors include ACH-1625 (Achillion), ABT-450 (Abbott/Enanta), BI201335 (Boehringer Ingelheim Pharma), VX-813 (Vertex), PHX1766 (Phenomix), VX-500 (Vertex), ITMN-191 (R-7227) (InterMune), MK7009 (Merck), BI 207127 (Boerhinger Ingelheim), SCH900518 (Schering/Merck), TMC435 (Medivir/Tibotec), SCH 503034 (Boceprevir, Schering), SCH900518 (Schering), Telaprevir (VX950) and (Vertex), XTL-2125 (XTL Biopharmaceuticals).

Additional examples of other therapeutic agents useful in the present methods and compositions include vaccines. Non-limiting examples of antiviral vaccines include: ChronVac-C, DNA-based Therapeutic Vaccine, (Inovio/Tripep), TG4040, Therapeutic Vaccine, (Transgene), PeviPROTM, Therapeutic vaccine, (Pevion Biotect), HCV/MF59, Vaccine(s), (Chiron/Novartis), GI-5005, Therapeutic Vaccine, (Globe Immune), IC41, Therapeutic Vaccine, (Intercell), HCV/MF59 (Chiron/Novartis), GI-5005 (Globe Immune), and Civacir (NABI).

Additional examples of other therapeutic agents useful in the present methods and compositions include anti-cancer agents. Non-limiting examples of antiviral anti-cancer agents include: ZIO-101, Anti-Liver Cancer (Arsenic), (Ziopharm Oncology), GV1001 (Heptovax), Anti-Liver Cancer, (Pharmexa), PI-88, Anti-liver cancer, (Progen Industries), Nexavar (sorafenib), Anti-liver cancer, (Onyx Pharmaceuticals), and ThermoDox (doxorubicin), Anti-liver cancer, (Celsion). Additional non-limiting examples of viral anticancer agents include CF102 (Can-Fite BioPharma), ZIO-101 (Ziopharm Oncology), GV1001 (Heptovax) (Pharmexa), PI-88 (Progen Industries), ThermoDox (doxorubicin) (Celsion), and Nexavar (sorafenib) (Onyx Pharmaceuticals).

Additional examples of other therapeutic agents useful in the present compositions and methods include, but are not limited to, Levovirin™ (ICN Pharmaceuticals, Costa Mesa, California), VP50406™ (Viropharma, Incorporated, Exton, Pennsylvania), ISIS14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, California), Maxamine™ (Maxim Pharmaceuticals, San Diego, Calif.), NKB-122 (JenKen Bioscience Inc., North Carolina), mycophenolate mofetil (Hoffman-LaRoche, Nutley, N.J.). Additional examples of other therapeutic agents useful in the present methods and compositions include adjunct therapeutics such as thrombopoeitin receiptor antagonists (e.g., LGD-4665, Ligand Pharmaceuticals Inc., and eltromobopag (Promacta), GlaxoSmithKline).

Additional examples of other therapeutic agents useful in the present compositions and methods include, but are not limited to: HCV/MF59, Oral Interferon alpha, Viramidine, Infergenl, Consensus, JBK-122, Bavituximab (Tarvacin), Civacir, Albuferon, IL-29 (PEG-Interferon lambda), Omega Interferon, ZADAXIN® (thymalfasin or thymosin alpha 1), NOV-205, PF-03491390 (formerly IDN-6556), Nexavar, ITMN-191, IC41, VX 950 (telaprevir), R1656, MX-3253 (Celgosivir), SCH 503034 (Boceprevir, Schering), SCH900518 (Schering), Belerofon (oral), VGX-410C, ThermoDox (doxorubicin), R7128, R1626, A-831, DEBIO-025, PeviPROTM, GV 1001, PYN17, PI-88, TG4040, BLX-883 (Locteron), ChronVac-R, MitoQ, GSK625433, SOV-07, IMO-2125, Alinia (nitazoxanide), LGD-4665, Z10-101, $CF_{102}$, VCH-759, VCH-916, Oglufanide disodium, VX-500, TMC435350, PF-00868554, GGI-5005 (Tarmogen), SPC3649 (LNA-antimiR™-122), CTS-1027, ABT-333, Eltrombopag, and ANA598.

Additional examples of other therapeutic agents useful in the present compositions and methods include, but are not limited to adjunct therapeutics. Non-limiting examples include: LGD-4665, Thrombopoeitin Receptor Agonist, (Ligand Pharmaceuticals Inc.), and Eltrombopag (Promacta), Thrombopoeitin Receptor Agonist, (GlaxcoSmithKline).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the compound(s) of the invention and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one compound of the invention and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU(12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A inteferon alpha 2a (commercially available from Hoffmann-La Roche), this agent is administered by subcutaneous or intramuscular injection at 3MIU(11.1 mcg/mL)/TIW for at least 48 to 52 weeks, or alternatively 6MIU/TIW for 12 weeks followed by 3MIU/TIW for 36 weeks.

In another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In another embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

The compounds of the invention may be used as the neat chemical or as part of a composition, such as a pharmaceutical composition. For example, when administered to a patient, the compounds of the invention can be administered as a component of a composition that comprises a pharmaceutically acceptable carrier or vehicle. The present invention provides pharmaceutical compositions comprising an effective amount of at least one compound of the invention and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection. Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more compounds of the invention are in a form suitable for oral administration.

In another embodiment, the one or more compounds of the invention are in a form suitable for intravenous administration.

In another embodiment, the one or more compounds of the invention are in a form suitable for topical administration.

In another embodiment, the one or more compounds of the invention are in a form suitable for sublingual administration.

In one embodiment, a pharmaceutical preparation comprising at least one compound of the invention is formulated in a unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the compound(s) of the invention by weight or volume. In various embodiments, the present compositions can contain, in one embodiment, from about 1% to about 70% or from about 5% to about 60% of the compound(s) of the invention by weight or volume.

The quantity of compound(s) of the invention in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the compound(s) of the invention will be determined according to the judgment of the attending clinician considering such factors as age, condition and size of the patient as well as severity of the symptoms being treated. Generally, a total daily dosage of the compound(s) of the invention range from about 0.1 to about 2000 mg per day, although variations will necessarily occur depending on the target of the therapy, the patient and the route of administration. In one embodiment, the dosage is from about) to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those described above. Accordingly, in one embodiment, the present invention provides compositions comprising: (i) at least one compound of the invention or a pharmaceutically acceptable salt, solvate, ester or prodrug thereof; (ii) one or more additional therapeutic agents that are not a compound of the invention; and (iii) a pharmaceutically acceptable carrier, wherein the amounts in the composition are together effective to treat a viral infection or a virus-related disorder.

Kits

In another embodiment, the present invention provides a kit comprising a therapeutically effective amount of at least one compound of the invention, or a pharmaceutically acceptable salt, solvate, ester, isomer, tautomer, or prodrug of said compound and a pharmaceutically acceptable carrier, vehicle or diluent.

In another aspect the present invention provides a kit comprising an amount of at least one compound of the invention, or a pharmaceutically acceptable salt, solvate, ester, isomer, tautomer, or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparant to those skilled in the art and are intended to fall within the scope of the appended claims.

A number of references have been cited herein. The entire disclosures of such references are incorporated herein by reference.

Therefore, we claim:

1. A pharmaceutical composition comprising a pharmaceutically acceptable carrier and a therapeutically effective amount of at least one compound of the structure shown in Formula (I.a):

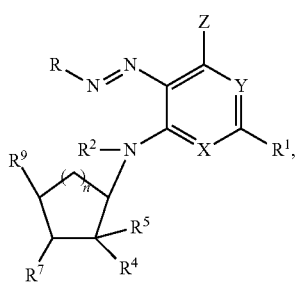

(I.a)

or a pharmaceutically acceptable salt thereof, wherein each of R, $R^1$, X, Y, Z, $R^2$, $R^4$, $R^5$, $R^7$, $R^9$ and n is selected independently and wherein:

n is 1;

R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkynyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)$NH_2$, —C(O)$NHR^{10}$, —C(O)$NR^{10}R^{11}$, —OC(O)$NH_2$, —CO(O)$NHR^{10}$, —CO(O)$NR^{10}R^{11}$, —$NH_2$, —$NHR^{10}$, —$NR^{10}R^{11}$, —$NO_2$, —S(O)$NHR^{10}$, —S(O)$NR^{10}R^{11}$, —S(O)$R^{10}$, —S(O)$_2$$NH_2$, —S(O)$_2$$NHR^{10}$, —S(O)$_2$$NR^{10}R^{11}$, —S(O)$_2$$R^{10}$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —$NH_2$, —$NHR^{12}$, and —$NR^{12}R^{13}$;

$R^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —$NH_2$, —$NHR^{14}$, —$NR^{14}R^{15}$, —$NO_2$, —S(O)$NHR^{10}$, —S(O)$NR^{10}R^{11}$, —S(O)$R^{10}$, —S(O)$_2$$NHR^{10}$, —S(O)$_2$$NR^{10}R^{11}$, and —S(O)$_2$$R^{10}$;

$R^2$ is H;

$R^4$ and $R^7$ are each independently selected from H and OH;

$R^5$ is selected from H, halo, and alkyl;

$R^9$ is alkyl, wherein said alkyl is unsubstituted or substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —OC(O)-alkyl, —OC(O)-alkenyl, —OC(O)-haloalkyl, —OC(O)-haloalkenyl, —O(C)O—$NHR^{10}$, —O(C)O—$N(R^{10})R^{11}$, —C(O)O-alkyl, —C(O)O-alkenyl, —C(O)O-haloalkyl, —C(O)O-haloalkenyl, —S(O)$_2$$R^{10}$, —$SR^{10}$, —S(O)$_2$$NHR^{10}$, —S(O)$_2$$NR^{10}R^{11}$, —CN, —$NH_2$, —$NHR^{16}$, and —$NR^{16}R^{17}$, —NHS(O)$_2$$R^{10}$,—N($R^{10}$)S(O)$_2$$R^{10}$, aryl, heteroaryl, cycloalkyl, cycloalkenyl, heterocycloalkyl, and heterocycloalkenyl;

each $R^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{10}$ and $R^{11}$ are linked together with the nitrogen to which they are attached to form an unsubstituted or substituted 4- or 6-membered heterocycloalkyl;

each $R^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{12}$ and $R^{13}$ are linked together with the nitrogen to which they are attached to form an unsubstituted or substituted 4- to 6-membered heterocycloalkyl;

each $R^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl,-alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, R$^{14}$ and R$^{15}$ are linked together with the nitrogen to which they are attached to form an unsubstituted or substituted 4- to 6-membered heterocycloalkyl;

each R$^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl; and each R$^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{16}$ and R$^{17}$ are linked together with the nitrogen to which they are attached to form an unsubstituted or substituted 4- or 6-membered heterocycloalkyl.

2. A pharmaceutical composition comprising a pharmaceutically acceptable carrier and a therapeutically effective amount of at least one compound of the structure shown in Formula (I.a):

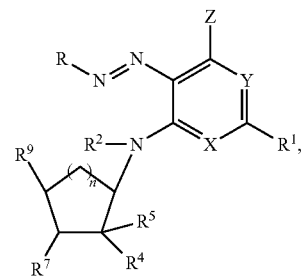

(I.a)

or a pharmaceutically acceptable salt thereof, wherein each of R, R$^1$, X, Y, Z, R$^2$, R$^4$, R$^5$, R$^7$, R$^9$ and n is selected independently and wherein:

n is 1;

R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkenyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)NH$_2$, —C(O)NHR$^{10}$, —C(O)NR$^{10}$R$^{11}$, —OC(O)NH$_2$, —CO(O)NHR$^{10}$, —CO(O)NR$^{10}$R$^{11}$, —NH$_2$, —NHR$^{10}$, —NR$^{10}$R$^{11}$, —NO$_2$, —S(O)NHR —S(O)NR$^{10}$R$^{11}$, —S(O)R$^{10}$, —S(O)$_2$NH$_2$, —S(O),NHR$^{10}$, —S(O)$_2$NR$^{10}$R$^{11}$, —S(O)$_2$R$^{10}$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$—NHR$^{12}$, and —NR$^{12}$R$^{13}$;

R$^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

R$^2$ is H;

R$^4$ is OH;

R$^7$ is OH;

R$^5$ is H;

R$^9$ is alkyl, wherein said alkyl is unsubstituted or substituted with from one to five groups independently selected from —OH, halo, —CN, —NH$_2$, —NHR$^{16}$, —NR$^{16}$R$^{17}$, —NHS(O)$_2$R$^{10}$, —N(R$^{10}$)S(O)$_2$R$^{10}$, —Oalkyl, —Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$;

each R$^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{10}$ and R$^{11}$ are linked together with the nitrogen to which they are attached to form an unsubstituted or substituted 4- or 6-membered heterocycloalkyl;

each R$^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{12}$ and R$^{13}$ are linked together with the nitrogen to which they are attached to form an unsubstituted or substituted 4- to 6-membered heterocycloalkyl;

each R$^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substituent being independently selected from —OH, halo, —NH$_2$. —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substituent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, R$^{14}$ and R$^{15}$ are linked together with the nitrogen to which they are attached to form an unsubstituted or substituted 4- to 6-membered heterocycloalkyl;

each R$^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl; and each R$^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{16}$ and R$^{17}$ are linked together with the nitrogen to which they are attached to form an unsubstituted or substituted 4- or 6-membered heterocycloalkyl.

3. A pharmaceutical composition comprising a pharmaceutically acceptable carrier and a therapeutically effective amount of at least one compound of the structure shown in Formula (I.a):

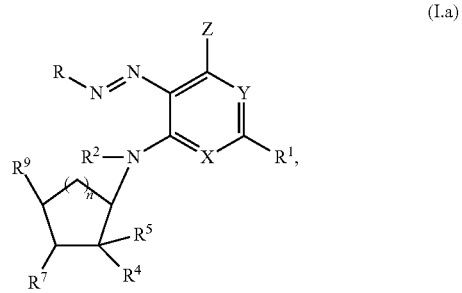

(I.a)

or a pharmaceutically acceptable salt thereof, wherein each of R, $R^1$, X, Y, Z, $R^2$, $R^4$, $R^5$, $R^7$, $R^9$ and n is selected independently and wherein:

n is 1,

R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkenyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)NH$_2$, —C(O)NHR$^{10}$, —C(O)NR$^{10}$R$^{11}$, —OC(O)NH$_2$, —CO(O)NHR$^{10}$, —CO(O)NR$^{10}$R$^{11}$, —NH$_2$, —NHR$^{10}$, —NR$^{10}$R$^{11}$, —NO$_2$, —S(O)NHR$^{10}$, —S(O)NR$^{10}$R$^{11}$, —S(O)R$^{10}$, —S(O)$_2$NH$_2$, —S(O),NHR$^{10}$, —S(O)$_2$NR$^{10}$R$^{11}$, —S(O)$_2$R$^{10}$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$, —NHR$^{12}$, and —NR$^{12}$R$^{13}$;

$R^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

$R^2$ is H, $R^4$ is OH;

$R^7$ is OH;

$R^5$ is —CH$_3$, $R^9$ is methyl, wherein said methyl is unsubstituted or substituted with from one to three groups independently selected from —OH, halo, alkyl, —CN, —NH$_2$, —NHR$^{16}$, —NR$^{16}$R$^{17}$, —NHS(O)$_2$R$^{10}$,)—N(R$^{10}$)S(O)$_2$R$^{10}$, —Oalkyl, —O-cycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$;

each $R^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{10}$ and $R^{11}$ are linked together with the nitrogen to which they are attached to form an unsubstituted or substituted 4- or 6-membered heterocycloalkyl;

each $R^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{12}$ and $R^{13}$ are linked together with the nitrogen to which they are attached to form an unsubstituted or substituted 4- to 6-membered heterocycloalkyl;

each $R^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each $R^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substituent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, R$^{14}$ and R$^{15}$ are linked together with the nitrogen to which they are attached to form an unsubstituted or substituted 4- to 6-membered heterocycloalkyl;

each R$^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl; and each R$^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{16}$ and R$^{17}$ are linked together with the nitrogen to which they are attached to form an unsubstituted or substituted 4- or 6-membered heterocycloalkyl.

4. A pharmaceutical composition comprising a pharmaceutically acceptable carrier and a therapeutically effective amount of at least one compound of the structure shown in Formula (I.a.10.j):

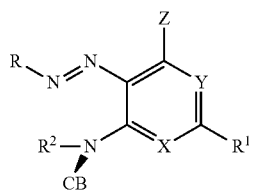

(I.a.10.j), or a pharmaceutically acceptable salt thereof, wherein each of R, R$^1$, X, Y, Z, R$^2$ and CB is selected independently and wherein R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkenyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)NH$_2$, —C(O)NHR$^{10}$, —C(O)NR$^{10}$R$^{11}$, —OC(O)NH$_2$, —CO(O)NHR$^{10}$, —CO(O)NR$^{10}$R$^{11}$, —NH$_2$, —NHR$^{10}$, —NR$^{10}$R$^{11}$, —NO$_2$, —S(O)NHR$^{10}$, —S(O)NR$^{10}$R$^{11}$, —S(O)R$^{10}$, —S(O)$_2$NH$_2$, —S(O)$_2$NHR$^{10}$, —S(O)$_2$NR$^{10}$R$^{11}$, —S(O)$_2$R$^{10}$ substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$, —NHR$^{12}$, and —NR$^{12}$R$^{13}$;

R$^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

R$^2$ is selected from H and alkyl;

CB is a moiety selected from the group consisting of:

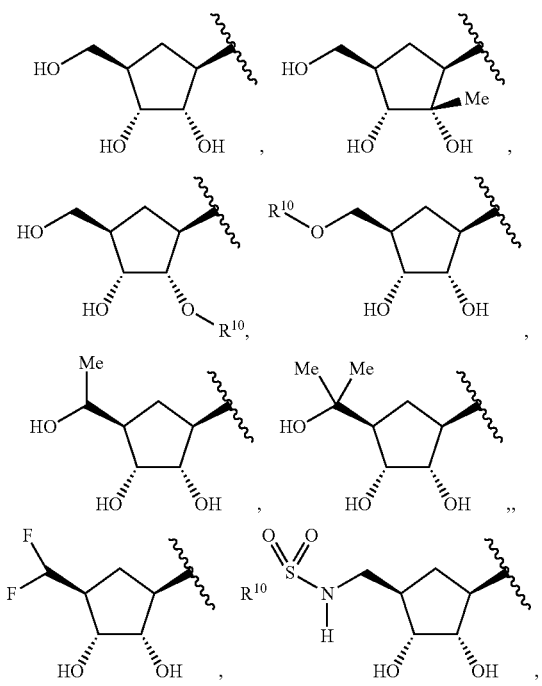

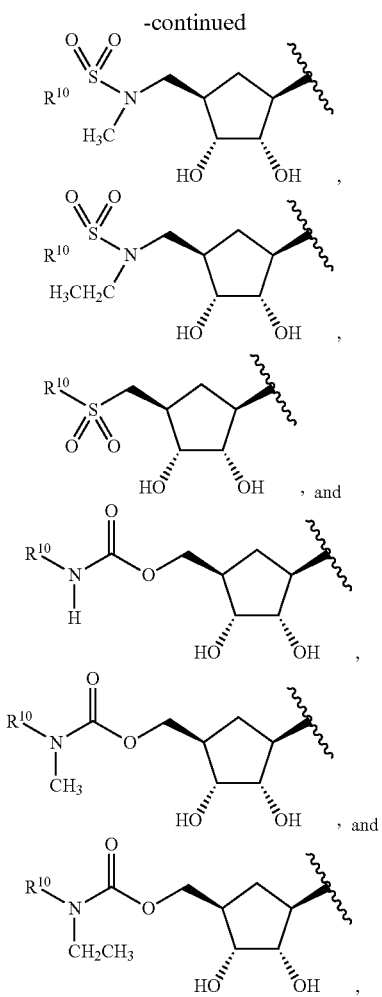

wherein each R[10] depicted under CB above is independently selected from the group consisting of methyl, ethyl, and cyclopropyl;
  each R[10] otherwise is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;
  each R[11] is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;
  or, alternatively, R[10] and R[11] are linked together with the nitrogen to which they are attached to form an unsubstituted or substituted 4- or 6-membered heterocycloalkyl;
  each R[12] is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;
  each R[13] is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;
  or, alternatively, R[12] and R[13] are linked together with the nitrogen to which they are attached to form an unsubstituted or substituted 4- to 6-membered heterocycloalkyl;
  each R[14] is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-,
  wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR[10], —NR[10]R[11], —C(O)OH, —C(O)OR[10], —C(O)NH$_2$, —C(O)NHR[10], —C(O)NR[10]R[11], —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl; and
  each R[15] is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl -, heteroaryl, and heteroaryl-alkyl-,
  wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR[10], —NR[10]R[11],—C(O)OH, —C(O)OR[10], —C(O)NH$_2$, —C(O)NHR[10], —C(O)NR[10]R[11], —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;
  or, alternatively, R[14] and R[15] are linked together with the nitrogen to which they are attached to form an unsubstituted or substituted 4- to 6-membered heterocycloalkyl.

5. A pharmaceutical composition according to claim 4, wherein in the compound of Formula (I.a.10.j), or pharmaceutically acceptable salt thereof:
  X is N;
  Y is N;
  R[2] is H; and
  Z is selected from the group consisting of H, methyl, and chloro;

R is unsubstituted phenyl or phenyl substituted with from 1 to 4 substituents independently selected from the group consisting of alkyl, alkoxy, cycloalkyl, halo, —CN, —NH$_2$, and —NO$_2$; and $R^1$ is selected from the group consisting of —NH$_2$, —NHR$^{14}$, and —NR$^{14}$R$^{15}$.

6. A pharmaceutical composition according to claim 5, wherein in the compound of Formula (I.a.10.j), or pharmaceutically acceptable salt thereof:

$R^1$ is —NH$_2$;

Z is selected from the group consisting of H, methyl, and chloro;

R is unsubstituted phenyl or phenyl substituted with from 1 to 4 substituents independently selected from the group consisting of alkyl, alkoxy, cycloalkyl, halo, —CN, —NH$_2$, and —NO$_2$;

$R^1$ is —NH$_2$; and

CB is a moiety having a formula:

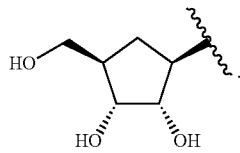

7. A pharmaceutical composition comprising a pharmaceutically acceptable carrier and a therapeutically effective amount of at least one compound of the structure shown in Formula (I.C):

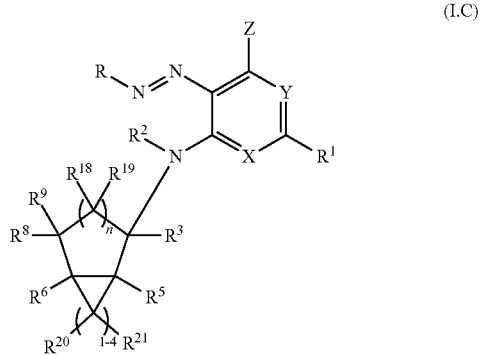

(I.C)

or a pharmaceutically acceptable salt thereof, wherein each of R, $R^1$, X, Y, Z, $R^2$, $R^3$, $R^5$, $R^6$, $R^8$, $R^9$, $R^{18}$, $R^{19}$, $R^{20}$, $R^{21}$, and n is selected independently and wherein R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkenyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)NH$_2$, —C(O)NHR$^{10}$, —C(O)NR$^{10}$R$^{11}$, —OC(O)NH$_2$, —CO(O)NHR$^{10}$, —CO(O)NR$^{10}$R$^{11}$, —NH$_2$, —NHR$^{10}$, —NR$^{10}$R$^{11}$, —NO$_2$, —S(O)NHR$^{10}$, —S(O)NR$^{10}$R$^{11}$, —S(O)R$^{10}$, —S(O)$_2$NH$_2$, —S(O)$_2$NHR$^{10}$, —S(O)$_2$NR$^{10}$R$^{11}$, —S(O)$_2$R$^{10}$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$, —NHR$^{12}$, and —NR$^{12}$R$^{13}$;

$R^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

$R^2$ is selected from H and alkyl;

n=0, 1, or 2;

$R^3$ is selected from H, -alkyl, -alkenyl, alkynyl, aryl, heteroaryl, and cycloalkyl, wherein each of said -alkyl, said -alkenyl, said alkynyl, said aryl, said heteroaryl, and said cycloalkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)Oalkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^5$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^6$ is selected from H, —OH, halo, -alkyl, -alkenyl, alkynyl, azido, aryl, heteroaryl, —O-alkyl,—O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^8$ is selected from H, —OH, halo, -alkyl, -alkenyl, alkynyl, azido, aryl, heteroaryl, —O-alkyl,—O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^1$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

$R^9$ is selected from H, —OH, halo, -alkyl, -alkenyl, alkynyl, azido, aryl, heteroaryl, —O-alkyl,—O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —S(O)$_2$NHR$^{10}$, —S(O)$_2$NR$^1$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

or, alternatively, $R^8$ and $R^9$ are taken together with the carbon atom to which they are shown attached to form a 3- to 7-membered, saturated or partially unsaturated, spirocycloalkyl ring containing from 0 to 3 spiro ring heteroatoms selected from O, N, and S;

each $R^{18}$ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$,—NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each $R^{19}$ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl,said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, n is 1 and $R^{18}$ and $R^{19}$ are taken together with the carbon atom to which they are attached to form a 3- to 7-membered, saturated or partially unsaturated, spirocycloalkyl ring containing from 0 to 3 spiro ring heteroatoms selected from O, N, and S;

$R^{20}$ and $R^{21}$ are each independently selected from H, alkyl, and heteroalkyl;

each $R^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{10}$ and $R^{11}$ are linked together with the nitrogen to which they are attached to form an unsubstituted or substituted 4- or 6-membered heterocycloalkyl;

each $R^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{12}$ and $R^{13}$ are linked together with the nitrogen to which they are attached to form an unsubstituted or substituted 4- to 6-membered heterocycloalkyl;

each $R^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each $R^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocy-cloalkyl-alkyl-, each said heterocycloalkenyl, each said heterocycloalkenyl-alkyl-, each said aryl, each said arylalkyl-, each said heteroaryl, and each said heteroarylalkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, $R^{14}$ and $R^{15}$ are linked together with the nitrogen to which they are attached to form an unsubstituted or substituted 4- to 6-membered heterocycloalkyl;

each $R^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl; and each $R^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{16}$ and $R^{17}$ are linked together with the nitrogen to which they are attached to form an unsubstituted or substituted 4- or 6-membered heterocycloalkyl.

8. A pharmaceutical composition comprising a pharmaceutically acceptable carrier and a therapeutically effective amount of at least one compound of the structure shown in Formula (I.D):

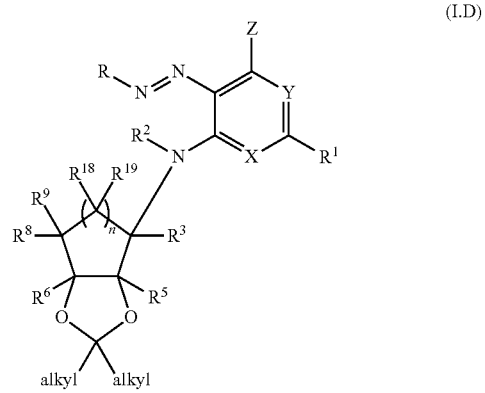

(I.D)

or a pharmaceutically acceptable salt thereof, wherein each of R, $R^1$, X, Y, Z, $R^2$, $R^3$, $R^5$, $R^6$, $R^8$, $R^9$, $R^{18}$, and $R^{19}$, and n is selected independently and wherein R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkenyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)NH$_2$, —C(O)NHR$^{10}$, —C(O)NR$^{10}$R$^{11}$, —OC(O)NH$_2$, —CO(O)NHR$^{10}$, —CO(O)NR$^{10}$R$^{11}$, —NH$_2$, —NHR$^{10}$, —NR$^{10}$R$^{11}$, —NO$_2$, —S(O)NHR$^{10}$, —S(O)NR$^{10}$R$^{11}$, —S(O)R$^{10}$, —S(O)$_2$NH$_2$, —S(O)$_2$NHR$^{10}$, —S(O)$_2$NR$^{10}$R$^{11}$, —S(O)$_2$R$^{10}$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NHR$^{12}$, and —NR$^{12}$R$^{13}$;

R$^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

R$^2$ is selected from H and alkyl;

n=0, 1, or 2;

R$^3$ is selected from H, -alkyl, -alkenyl, alkynyl, aryl, heteroaryl, and cycloalkyl, wherein each of said -alkyl, said -alkenyl, said alkynyl, said aryl, said heteroaryl, and said cycloalkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

R$^5$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, R$^4$ and R$^5$ are taken together with the carbon atom to which they are shown attached to form a 3- to 7-membered, saturated or partially unsaturated, spirocycloalkyl ring containing from 0 to 3 spiro ring heteroatoms selected from O, N, and S;

R$^6$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, R$^5$ and R$^6$ are taken together to form a double bond;

R$^8$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl,)—O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

R$^9$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$ —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

or, alternatively, R$^8$ and R$^9$ are taken together with the carbon atom to which they are shown attached to form a 3- to 7-membered, saturated or partially unsaturated, spirocycloalkyl ring containing from 0 to 3 spiro ring heteroatoms selected from O, N, and S;

each R$^{18}$ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each R$^{19}$ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, n is 1 and R$^{18}$ and R$^{19}$ are taken together with the carbon atom to which they are attached to form a 3- to 7-membered, saturated or partially unsaturated, spirocycloalkyl ring containing from 0 to 3 spiro ring heteroatoms selected from O, N, and S;

each R$^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{10}$ and R$^{11}$ are linked together with the nitrogen to which they are attached to form an unsubstituted or substituted 4- or 6-membered heterocycloalkyl;

each R$^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{12}$ and R$^{13}$ are linked together with the nitrogen to which they are attached to form an unsubstituted or substituted 4- to 6-membered heterocycloalkyl;

each R$^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substituent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substituent being independently selected from —OH, halo, —NH$_2$, —NHR$^{10}$, —NR¹⁰R¹¹, —C(O)OH, —C(O)OR¹⁰, —C(O)NH₂, —C(O)NHR¹⁰, —C(O)NR¹⁰R¹¹, —S(O)₂alkyl, —S(O)₂aryl, alkyl, alkoxy, haloalkyl, haloalkoxy, heteroaryl, heteroalkyl, heterohaloalkyl, aryl, cycloalkyl, and heterocycloalkyl;

or, alternatively, R¹⁴ and R¹⁵ are linked together with the nitrogen to which they are attached to form an unsubstituted or substituted 4- to 6-membered heterocycloalkyl;

each R¹⁶ is independently selected from alkyl, alkenyl, haloalkyl, heteroalkyl, heterohaloalkyl, —S(O)₂-alkyl, -alkyl-OH, —C(O)Oalkyl, —C(O)alkyl, —C(O)NHalkyl, —C(O)N(alkyl)₂, cycloalkyl, heterocycloalkyl, heterocycloalkenyl, aryl, and heteroaryl; and each R¹⁷ is independently selected from alkyl, alkenyl, haloalkyl, heteroalkyl, heterohaloalkyl, —S(O)₂-alkyl, -alkyl-OH, —C(O)Oalkyl, —C(O)alkyl, —C(O)NHalkyl, —C(O)N(alkyl)₂, cycloalkyl, heterocycloalkyl, heterocycloalkenyl, aryl, and heteroaryl;

or, alternatively, R¹⁶ and R¹⁷ are linked together with the nitrogen to which they are attached to form an unsubstituted or substituted 4- or 6-membered heterocycloalkyl.

9. A compound according of the structure shown in Formula (I.E):

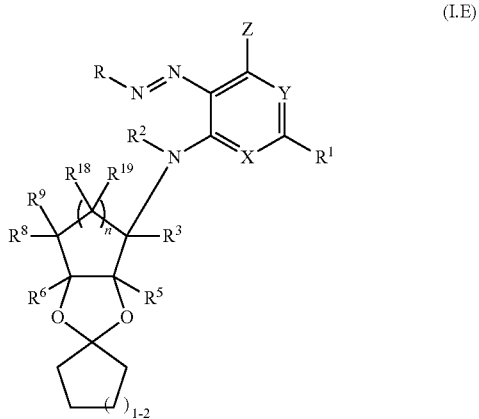

(I.E)

or a pharmaceutically acceptable salt thereof, wherein each of R, R¹, X, Y, Z, R², R³, R⁵, R⁶, R⁸, R⁹, R¹⁸, and R¹⁹, and n is selected independently and wherein R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkynyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroarylalkyl, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocloalkyl, —C(O)NH₂, —C(O)NHR¹⁰, —C(O)NR¹⁰R¹¹, —OC(O)NH₂, —CO(O)NHR¹⁰, —CO(O)NR¹⁰R¹¹, —NH₂, —NHR¹⁰, —NR¹⁰R¹¹, —NO₂, —S(O)NHR¹⁰, —S(O)NR¹⁰R¹¹, —S(O)R¹⁰, —S(O)₂NH₂, —S(O)₂NH₂, —S(O)₂NHR¹⁰, —S(O)₂NR¹⁰R¹¹, —S(O)₂R¹⁰, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH₂, —NHR¹², and —NR¹²R¹³;

R¹ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH₂, —NHR¹⁴, —NR¹⁴R¹⁵, —NO₂, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰;

R² is selected from H and alkyl;

n=0, 1, or 2;

R³ is selected from H, -alkyl, -alkenyl, alkynyl, aryl, heteroaryl, and cycloalkyl, wherein each of said -alkyl, said -alkenyl, said alkynyl, said aryl, said heteroaryl, and said cycloalkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

R⁵ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, R⁴ and R⁵ are taken together with the carbon atom to which they are shown attached to form a 3- to 7-membered, saturated or partially unsaturated, spirocycloalkyl ring containing from 0 to 3 spiro ring heteroatoms selected from O, N, and S;

$R^6$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$ wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, $R^5$ and $R^6$ are taken together to form a double bond;

$R^8$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl,)—O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

$R^9$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —N(R$^{10}$)S(O)$_2$R$^{10}$, —NHS(O)$_2$R$^{10}$, aryl, heteroaryl, cycloalkyl, cycloalkenyl, heterocycloalkyl, and heterocycloalkenyl;

or, alternatively, $R^8$ and $R^9$ are taken together with the carbon atom to which they are shown attached to form a 3- to 7-membered, saturated or partially unsaturated, spirocycloalkyl ring containing from 0 to 3 spiro ring heteroatoms selected from Ol N, and S;

each $R^{18}$ (when present) is selected from H, —OH, halo, -alkyl, -alkenyl, alkynyl, azido, aryl, heteroaryl, —O-alkyl,-O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each $R^{19}$ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, n is 1 and $R^{18}$ and $R^{19}$ are taken together with the carbon atom to which they are attached to form a 3- to 7-membered, saturated or partially unsaturated, spirocycloalkyl ring containing from 0 to 3 spiro ring heteroatoms selected from O, N, and S;

each $R^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{10}$ and $R^{11}$ are linked together with the nitrogen to which they are attached to form an unsubstituted or substituted 4- or 6-membered heterocycloalkyl;

each $R^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each $R^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{12}$ and $R^{13}$ are linked together with the nitrogen to which they are attached to form an unsubstituted or substituted 4- to 6-membered heterocycloalkyl;

each $R^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each $R^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, aryl-alkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituents, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, $R^{14}$ and $R^{15}$ are linked together with the nitrogen to which they are attached to form an unsubstituted or substituted 4- to 6-membered heterocycloalkyl;

each $R^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl; and each $R^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, $R^{16}$ and $R^{17}$ are linked together with the nitrogen to which they are attached to form an unsubstituted or substituted 4- or 6-membered heterocycloalkyl.

10. A pharmaceutical composition comprising a pharmaceutically acceptable carrier and a therapeutically effective amount of at least one compound selected from the group consisting of:

| Compd # | Structure |
|---|---|
| 1 | (structure) |
| 2 | (structure) |
| 3 | (structure) | or a pharmaceutically acceptable salt thereof.

11. A pharmaceutical composition comprising a therapeutically effective amount of at least one compound according to claim 9 or a pharmaceutically acceptable salt thereof, and a pharmaceutically acceptable carrier.

12. A method of treating a viral infection comprising administering to a patient in need of such treatment a therapeutically effective amount of at least one compound according to claim 9, or a pharmaceutically acceptable salt thereof.

13. A method of treating a viral infection comprising administering to a patient in need of such treatment a pharmaceutical compositon according to claim 1.

14. A method of treating a viral infection comprising administering to a patient in need of such treatment a pharmaceutical compositon according to claim 2.

15. A method of treating a viral infection comprising administering to a patient in need of such treatment a pharmaceutical compositon according to claim 3.

16. A method of treating a viral infection comprising administering to a patient in need of such treatment a pharmaceutical compositon according to claim 7.

17. A method of treating a viral infection comprising administering to a patient in need of such treatment a pharmaceutical compositon according to claim 8.

* * * * *